(12) United States Patent
Bare et al.

(10) Patent No.: US 6,214,826 B1
(45) Date of Patent: Apr. 10, 2001

(54) PYRIDAZINO QUINOLINE COMPOUNDS

(75) Inventors: Thomas Michael Bare, West Chester, PA (US); Marc Jerome Chapdelaine; Timothy Wayne Davenport, both of Wilmington, DE (US); James Roy Empfield, Bear, DE (US); Laura Enid Garcia-Davenport, Wilmington, DE (US); Paul Francis Jackson, Bel Air, MD (US); Jeffrey Alan McKinney, Palo Alto, CA (US); Charles David McLaren, Landenberg; Richard Bruce Sparks, Boothwyn, both of PA (US)

(73) Assignee: Zeneca Limited (GB)

( * ) Notice: Subject to any disclaimer, the term of this patent is extended or adjusted under 35 U.S.C. 154(b) by 0 days.

(21) Appl. No.: 09/365,562

(22) Filed: Aug. 2, 1999

Related U.S. Application Data

(63) Continuation of application No. 09/128,038, filed on Aug. 3, 1998, now abandoned, which is a continuation of application No. 08/836,082, filed on May 2, 1997, now abandoned.

(30) Foreign Application Priority Data

Nov. 12, 1994 (GB) .................................................. 9422894

(51) Int. Cl.$^7$ ..................... A61K 31/5025; C07D 471/04
(52) U.S. Cl. ........................................... 514/248; 544/234
(58) Field of Search ............................. 544/234; 514/248

(56) References Cited

U.S. PATENT DOCUMENTS

| | | | |
|---|---|---|---|
| 5,599,814 | 2/1997 | Bare et al. | 544/234 |
| 5,604,227 | 2/1997 | Bare et al. | 544/234 |
| 5,652,239 | 7/1997 | Bare et al. | 544/234 |
| 5,733,910 | 3/1998 | Bare et al. | 544/234 |
| 5,744,471 | 4/1998 | Bare et al. | 544/234 |
| 5,837,705 | * 11/1998 | Bare et al. | 514/248 |

FOREIGN PATENT DOCUMENTS

| | | |
|---|---|---|
| 512817 | 11/1992 | (EP) . |
| 516297 | 12/1992 | (EP) . |
| 95/11244 | 4/1995 | (WO) . |

OTHER PUBLICATIONS

Bare et al. *Chem Abstr.*, vol. 123, Abstract No. 313994 and lists of registry number therein, abstracting v00951 11244 (1995).

Kurasawa et al., *Heterocycles*, 14(3), 267–270 (1980).

Luo et al., *J. Heterocyclic Chem.*, 28, 205–208, (1991).

Kurasawa et al., *Chem. Pharm. Bull.*, 28(12) 3457–3465 (1980).

Godard et al., *Bull. Soc. Chim. Fr.*, 1588–1592 (1972).

Ried et al., *Chem. Ber.*, 85, 204–216 (1952).

Tominaga et al., *J. Heterocyclic Chem.*, 30, 267–273 (1993).

Louvel et al., *Tips*, 8, p. 196–203 (1997).

Purdon et al., *J. Psychiatr. Neurosc.*, 19, p. 359–367 (1994).

Lipton, *Molecular Neurobiology*, 8, p. 181–196 (1994).

* cited by examiner

*Primary Examiner*—Emily Bernhardt
(74) *Attorney, Agent, or Firm*—Kenneth F. Mitchell

(57) ABSTRACT

The invention relates to pyridazinoquinoline compounds of the formulas B and B'

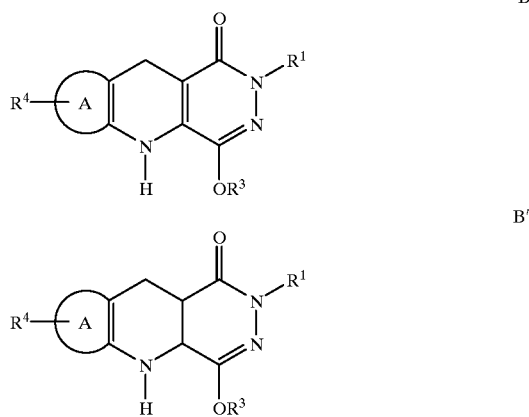

wherein Ring A is selected from an ortho fused aromatic or heteroaromatic five- or six-membered ring and $R^1$, $R^3$ and $R^4$ are substituents selected from halo, OH, $OCF_3$, $NO_2$, CN, NR'R'', $SO_2NR'R''$, $SO_mR'$alkyl, and a variety of alkyl, aryl, heterocyclic and heteroaryl groups, to pharmaceutical compositions containing them and to methods utilizing them for the treatment of neurological disorders.

8 Claims, No Drawings

PYRIDAZINO QUINOLINE COMPOUNDS

This is a continuation of U.S. patent application Ser. No. 09/128,038, filed Aug. 3, 1998, abandoned, which is a continuation of U.S. patent application Ser. No. 08/836,082, filed May 2, 1997, abandoned, which is a § 371 of PCT Application PCT/GB95/02613, filed Nov. 8, 1995.

This invention relates to pyridazineone compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, psychosis, Huntington's chorea, amyotrophic lateral sclerosis, Alzheimer's disease, Parkinson's disease, Olivo-pontocerebellar atrophy, viral-induced neurodegeneration such as in acquired immunodeficiency syndrome and its associated dementia, anoxia such as from drowning, spinal cord and brain trauma, and chronic pain, for the prevention of drug and alcohol withdrawal symptoms, and for the inhibition of tolerance and dependence to opiate analgesics. The invention particularly relates to novel pyridazineone compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

The compounds provided by this invention may be useful in a variety of neurodegenerative disorders because they function as excitatory amino acid antagonists. They may do so indirectly, via allosteric modulation of the glutamate binding site, specifically by acting as antagonists of the strychnine-insensitive glycine receptor on the NMDA receptor complex. They may also do so directly, by binding to the glutamate site itself on the NMDA receptor complex.

The present invention relates to a compound of formula B or B'

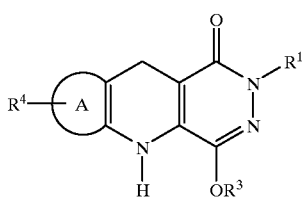

B

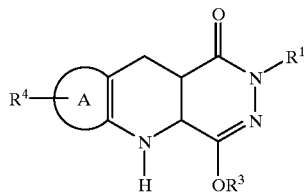

B' or pharmaceutically acceptable salts thereof: wherein:

Ring A is chosen from an ortho fused aromatic or heteroaromatic five- or six-membered ring selected from phenyl, pyridyl, furyl, pyrrolyl or thienyl either unsubstituted or multi-substituted at a ring carbon atom with $R^4$ wherein $R^4$ at each occurrence is independently selected from halo, $(C_1-C_4)$alkyl, $NO_2$, CN, perfluoro $(C_1-C_4)$alkyl, OH, $OCF_3$, $(C_2-C_4)$alkenyl, $(C_2-C_4)$alkynyl, $O(C_1-C_4)$alkyl, NR'R'', $SO_2$NR'R'', $SO_m$R' where m is 0, 1 or 2, a heterocyclic group, NR'COR'', COR'', NR'CO$_2$R'', CO$_2$R' and CONR'R'';

$R^1$ is selected from H, $(C_1-C_6)$alkyl and $-(CH_2)_nL$ where n is selected from 0, 1, 2, 3, 4, 5 or 6, and L is selected from $-OH$, $-O(C_1-C_4)$alkyl, $CF_3$, $-O(C_1-C_4)$alkylaryl, $(C_1-C_4)$alkylCOOR', OCOR', $SO_m$R', NR'R'' with the proviso that NR'R'' is not equal to $NH_2$, NR'COR'', NR'CO$_2$R'', NRCONR'R'', $CO_2$R', CONRR', M and W, wherein:

M is phenyl, or a benz derivative thereof, substituted with 0, 1, 2, 3 or 4 groups chosen from: $-O-(C_1-C_4)$alkyl, $-O-(C_2-C_4)$alkenyl, $-O-(C_2-C_4)$alkynyl, $-O(C_0-C_6)$alkylphenyl, $-OH$, -halo, $-NO_2$, $-CN$, $-CF_3$, $-(C_1-C_4)$alkylCF$_3$, $-NH(CO)R'$, $-(C_1-C_4)$alkyl, $-NR'R''$, $-CO_2R'$, $-CONR'R''$, $-SO_mR'$, $-SO_2NR'R''$, $(C_1-C_6)$alkyloxy$(C_1-C_6)$alkyloxy-, hydroxy$(C_1-C_6)$alkyloxy-, oxy$(C_1-C_6)$alkyloxy which may form a cyclic ring attached to the phenyl ring in an ortho manner, aryloxy$(C_1-C_4)$alkyloxy$(C_1-C_4)$alkyl, $(C_1-C_6)$alkyloxy$(C_1-C_6)$alkyloxy$(C_1-C_6)$alkyloxy-, hydroxy$(C_1-C_6)$alkyloxy$(C_1-C_6)$alkyloxy-, $-O(C_1-C_6)$alkylNR'R'', $-NR'(C_1-C_6)$alkylNR'R'', $-(C_1-C_6)$alkylNR'R'', $-O$-perfluoro$(C_1-C_4)$alkyl, -perfluoro$(C_1-C_4)$alkyl, $-NR'(C_1-C_6)$alkyloxy), $-NR'(C_1-C_6)$alkylhydroxy, $-(C_1-C_4)$alkyl)oxy$(C_1-C_4)$alkyl, $-O(C_1-C_4)$alkylCOOR', $-(C_1-C_4)$alkylNR'R'', $-(C_1-C_4)$alkylOR', $-NR'(CH_2)_q$COOR' where q is 1, 2, 3 or 4, $-SO_m(C_1-C_4)$alkyloxy$(C_1-C_4)$alkyl, $-SO_m(C_1-C_4)$alkyloxy$(C_1-C_4)$alkyloxy$(C_1-C_4)$alkyl, $-NR'(C_1-C_4)$alkyloxy$(C_1-C_4)$alkyl, $-NR'(C_1-C_4)$alkyloxy$(C_1-C_4)$alkyloxy$(C_1-C_4)$alkyl; or M is heterocycle selected from a five-, six- or seven-membered heterocyclic rings containing 1, 2, or 3 heteroatoms chosen from O, N, or S, or aryl or heteroaryl benz derivatives thereof wherein: the N on the heterocycle is optionally substituted with R'; a carbon or nitrogen atom on the heterocycle may be substituted with R or R'; a carbon atom may be disubstituted to form a $C_5-C_7$ spiral group; a carbon atom or sulfur atom may be substituted with O to form a carbonyl group or the group $SO_m$, with the proviso that a heterocyclic nitrogen may not be attached to a nitrogen or the tricyclic ring system of a compound of formula B; or M is heteroaryl selected from unsubstituted or substituted aromatic species and benz derivatives thereof including pyridyl, thienyl, and furanyl; those groups containing two heteroatoms selected from N, O or S such as pyrazole, imidazole, isoxazole, oxazole, thiazole or isothiazole (and oxidized versions thereof selected from $SO_m$), pyridazine, pyrimidine, pyrazine; those groups containing three heteroatoms chosen from N, O or S such as triazole or oxadiazole or triazine, and those groups containing four heteroatoms such as tetrazole; wherein: the N on the heteroaryl group is optionally substituted with R and the substituted aromatic substituents include typical aromatic substituents selected from hydroxy, alkoxy, halo or cyano and the heteroaryl group is attached to —$(CH_2)_n$ via a carbon atom or a heteroatom on the heteroaryl group;

W is selected from OH, OR', OCOR', $SO_mR'$, $SO_mNR'R''$, halo, $CF_3$, NR'R" with the proviso that NR'R" is not equal to $NH_2$; or W is COR', NR'COR", NR'CO$_2$R", $(C_3-C_6)$cycloalkyl, NRCONR'R", CO$_2$R', or CONRR' with the proviso that for any foregoing W moiety n is greater than zero;

$R^3$ is selected from H or —$C(O)R^6$ wherein $R^6$ is selected from $(C_1-C_{12})$alkyl, $(C_2-C_{12})$alkenyl and $(C_2-C_{12})$alkynyl;

R is selected from H or $(C_1-C_4)$alkyl, and

R' and R" at each occurrence are independently selected from H, $(C_1-C_4)$alkyl, $(C_2-C_4)$alkenyl, $(C_2-C_4)$alkynyl, $(C_3-C_6)$cycloalkyl, phenyl$(C_0-C_4)$alkyl-, heterocycle$(C_0-C_4)$alkyl- and heteroaryl$(C_0-C_4)$alkyl- wherein phenyl, heterocycle and heteroaryl moieties are as defined above and any R' or R" moiety is optionally substituted at one or more carbon atoms with halo, H, $(C_1-C_4)$alkyl, $(C_3-C_6)$cycloalkyl, phenyl, $NO_2$, CN, $CF_3$, OH and O-$(C_1-C_4)$alkyl.

Aromatic, heterocycle or heteroaryl M-moieties of compounds of the present invention can be substituted at 1, 2, 3 or 4 positions with moieties selected from —OH, -halo, $NH_2$, $NO_2$, —CN, —$CF_3$, $(C_1-C_4)$alkyl, —O-$(C_1-C_4)$alkyl, —O-phenyl, or O-$(C_1-C_6)$alkyl-phenyl.

In addition, the invention relates to a compound of formula B or a pharmaceutically acceptable salt thereof wherein:

Ring A is chosen from an ortho fused aromatic or heteroaromatic five- or six-membered ring selected from phenyl, pyridyl, pyrrolyl or thienyl either unsubstituted or substituted at one or more ring carbon atoms with $R^4$ wherein $R^4$ is independently selected from the group consisting of hydrogen, halo, $(C_1-C_4)$alkyl, $NO_2$, CN, perfluoro$(C_1-C_3)$alkyl, OH, $OCF_3$, $(C_2-C_4)$alkenyl, $(C_2-C_4)$alkynyl, O-$(C_1-C_4)$alkyl, NR'R", $SO_2NR'R"$, or $SO_mR'$;

$R^1$ is —$(CH_2)_nL$ wherein:

L is selected from —OH, —O$(C_1-C_4)$alkyl, $CF_3$, —O$(C_1-C_4)$alkylaryl, $(C_1-C_4)$alkylCOOR', OCOR', $SO_mR'$, NR'R" with the proviso that NR'R" is not equal to $NH_2$, NR'COR", NR'CO$_2$R", NRCONR'R", CO$_2$R' and CONRR'; or L is selected from phenyl or benz derivatives thereof and is either unsubstituted or substituted with 1, 2, 3 or 4 groups selected from: —O-$(C_1-C_4)$alkyl, —O-$(C_2-C_4)$alkenyl, —O-$(C_2-C_4)$alkynyl, —O$(C_0-C_6)$alkylphenyl, —OH, -halo, —$NO_2$, —CN, —$CF_3$, —$(C_1-C_4)$alkylCF$_3$, —NH(CO)R', —$(C_1-C_4)$alkyl, —NR'R", —CO$_2$R', —CONR'R", —$SO_mR'$, —$SO_2NR'R"$, $(C_1-C_6)$alkyloxy$(C_1-C_6)$alkyloxy-, hydroxy$(C_1-C_6)$alkyloxy-, oxy$(C_1-C_6)$alkyloxy which may form a cyclic ring attached to the phenyl ring in an ortho manner, aryloxy$(C_1-C_4)$alkyloxy $(C_1-C_4)$alkyl, $(C_1-C_6)$alkyloxy$(C_1-C_6)$alkyloxy $(C_1-C_6)$alkyloxy-, hydroxy$(C_1-C_6)$alkyloxy$(C_1-C_6)$alkyloxy-, —O$(C_1-C_6)$alkylNR'R", —NR'$(C_1-C_6)$alkylNR'R",-$(C_1-C_6)$alkylNR'R", —O-perfluoro$(C_1-C_4)$alkyl, -perfluoro$(C_1-C_4)$alkyl, —NR'$(C_1-C_6)$alkyloxy, —NR'$(C_1-C_6)$alkylhydroxy, —$(C_1-C_4)$alkyloxy$(C_1-C_4)$alkyl, —O$(C_1-C_4)$alkylCOOR', —$(C_1-C_4)$alkylNR'R", —$(C_1-C_4)$alkylOR', —NR'$(CH2)_q$COOR', —$SO_m(C_1-C_4)$alkyl)oxy$(C_1-C_4)$alkyl, —$SO_m(C_1-C_4)$alkyloxy$(C_1-C_4)$alkyloxy$(C_1-C_4)$alkyl, —NR'$(C_1-C_4)$alkyloxy$(C_1-C_4)$alkyl, —NR'$(C_1-C_4)$alkyloxy$(C_1-C_4)$alkyloxy$(C_1-C_4)$alkyl; or L is selected from heterocycle wherein heterocycle is selected from a five- and/or six- and/or seven-membered heterocyclic ring containing 1, 2, or 3 heteroatoms chosen from O, N, or S wherein the N on the heterocycle is optionally substituted with R' and a carbon or nitrogen atom on the heterocycle may be substituted with R or R' or a carbon atom may be disubstituted to form a $C_5$-$C_7$ spiral group or a carbon atom or sulfur atom may be substituted with O to form a carbonyl group or sulfonyl group $SO_m$; wherein the heterocyclic groups may be selected from, for example, 2-pyrrolidinone, piperazine, oxazolidone, 2,5-oxazolidinedione, 2,4-imidazolidinedione, 2,4-thiazolidinedione or succinimide; aryl or benz or heteroarylbenz derivatives thereof (3,4-pyridinedicarboximide, -1-phthalimido, isatoic anhydride, orthobenzoicsulfimide) either unsubstituted or mono, bi or tri-substituted with alkyl or aromatic substituents including -halo, —$(C_1-C_6)$alkyl, —OH, $(C_1-C_6)$alkoxy, phenyl, $OCF_3$, $CF_3$, $NO_2$, CN, $NH_2$, $SO_mR'$, $NH(C_1-C_4)$alkyl, or $N((C_1-C_4)alkyl)_2$; or L is selected from heteroaryl wherein heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole, isothiazole, or those groups containing three heteroatoms chosen from N, O or S such as triazole or oxadiazole or those groups containing 4 heteroatoms such as tetrazole wherein the N on the heteroaryl group is optionally substituted with R and the substituted aromatic substituents include typical aromatic substituents selected from hydroxy, alkoxy, halo or cyano and the heteroaryl group is attached to —$(CH_2)_n$ via a carbon atom or a heteroatom on the heteroaryl group;

n is selected from 1, 2, 3 and 4, and

R, $R^3$, $R^6$, R', R" and m are as previously defined.

The present invention also relates to a compound of formula T' wherein Ring A, $R^4$, $R^1$ and $R^3$ are as defined for those variables in formulae A or B and pharmaceutical compositions and methods of use thereof as recited for compositions and compounds of formula A.

The present invention further relates to a compound of formula U wherein A, $R^4$, $R^1$ and $R^3$ are as defined for those variables in formula A or B and further wherein R' or R" are selected independently from H or $(C_1-C_6)$alkyl or $(C_1-C_6)$alkylaryl.

The present invention also relates to pharmaceutical compositions of formula U and methods of use as recited herein for compounds or compositions of formulae A or B.

The present invention also relates to an intermediate compound of formula D or D1 wherein: Ring A is chosen from an ortho fused aromatic or heteroaromatic five- or six-membered ring selected from phenyl, pyridyl, pyrrolyl or thienyl either unsubstituted or substituted at one or more ring carbon atoms with $R^4$ wherein $R^4$ is independently selected from the group consisting of hydrogen, halo, $(C_1-C_4)$alkyl, $NO_2$, CN, perfluoro$(C_1-C_3)$alkyl, OH, $OCF_3$, $(C_2-C_4)$alkenyl, $(C_2-C_4)$alkynyl, $O(C_1-C_4)$alkyl, NR'R", $SO_2NR'R"$, or $SO_mR'$, a heterocyclic group, NR'COR", COR", $NR'CO_2R"$, $CO_2R'$ and CONR'R"; X is halogen; n is 1–4; and $R^3$, R, R', R" and m are as previously defined.

Particular compounds of formula B are those wherein:
Ring A is chosen from phenyl, or pyridyl either unsubstituted or substituted at a ring carbon atom with $R^4$ wherein $R^4$ is independently selected from the group consisting of halo, $(C_1-C_4)$alkyl, $NO_2$, CN, perfluoro$(C_1-C_3)$alkyl, OH, $OCF_3$, $(C_2-C_4)$alkenyl, $(C_2-C_4)$alkynyl and $O-(C_1-C_4)$alkyl;
$R^1$ is selected from H, $(C_1-C_6)$alkyl, $—(CH_2)_nM$ and $—(CH_2)_nW$, wherein;
n is selected from 0, 1, 2, 3, 4, 5 and 6;
M is phenyl which is either unsubstituted of substituted with 1, 2, 3 or 4 groups chosen independently from $—O-(C_1-C_4)$alkyl, $—O-(C_2-C_4)$alkenyl, $—O-(C_2-C_4)$alkynyl, $—O-(C_0-C_6)$phenyl, —OH, -halo, $—NO_2$, —CN, $—CF_3$, $—(C_1-C_4)$alkyl; or
M is heteroaryl wherein heteroaryl is selected from unsubstituted or substituted aromatic species (a) chosen from pyridyl, thienyl, or furanyl, or (b) those groups containing two heteroatoms selected from N, O, or S which are chosen from pyrazole, imidazole, isoxazole, oxazole, thiazole, isothiazole, pyridazine, pyrimidine or pyrazine, wherein the substituted aromatic substituents are selected from hydroxy, alkoxy, halo or cyano and wherein the heteroaryl group is attached to $—(CH_2)_n$ via a carbon atom;
W is selected from OH, OR', $SO_mR'$ where m is 0, 1 or 2, $SO_mNR'R"$, halo, $CF_3$ or NR'R" with the proviso that n is greater than 0;
$R^3$ is selected from H, or $—(CO)R^6$ wherein $R^6$ is selected from $(C_1-C_{12})$alkyl which may bear a group selected from CN, $OR^e$, and $CO_2R^e$, wherein $R^e$ is selected from hydrogen, $(C_1-C_4)$alkyl, and phenyl; phenyl and phenyl$(C_1-C_4)$alkyl, and
R' and R" are independently selected from H, $(C_1-C_4)$ alkyl, and phenyl$(C_0-C_4)$alkyl- wherein phenyl is optionally substituted at one or more carbon atoms with halo, $(C_1-C_4)$alkyl, $NO_2$, CN, $CF_3$, OH, or $O-(C_1-C_4)$ alkyl.

Preferred compounds of the formula B above are those wherein:
Ring A is phenyl either unsubstituted or substituted at a ring carbon atom with $R^4$ wherein $R^4$ is independently selected from the group consisting of halo, $(C_1-C_4)$alkyl and $O-(C_1-C_4)$alkyl;
$R^1$ is selected from H, $(C_1-C_6)$alkyl, $—(CH_2)_nM$ and $—(CH_2)_nW$, wherein;
n is selected from 0, 1, 2, 3, 4, 5 and 6;
M is phenyl which is either unsubstituted or substituted with 1, 2, 3 or 4 groups chosen independently from $—O-(C_1-C_4)$alkyl, $—O-(C_0-C_6)$alkylphenyl, —OH, -halo, —CN, $—CF_3$ or $-(C_1-C_4)$alkyl; or
M is heteroaryl wherein heteroaryl is selected from unsubstituted or substituted aromatic species chosen from pyridyl, thienyl or furanyl, wherein the substituted aromatic substituents are selected from hydroxy, or alkoxy;
W is selected from OH, OR', SOR', or NR'R" with the proviso that n is greater than 0;
$R^3$ is selected from H, or $—(CO)R^6$ wherein $R^6$ is selected from $(C_1-C_4)$alkyl which may bear a group selected from $CO_2R^e$ wherein $R^e$ is $(C_1-C_4)$alkyl and phenyl, and
R' and R" are independently selected from H, $(C_1-C_4)$ alkyl and phenyl$(C_0-C_4)$alkyl- wherein phenyl is optionally substituted at one carbon atom with halo, OH, or $O-(C_1-C_4)$alkyl.

Particularly preferred compounds of the formula B above are those wherein:
$R^3$ and m are as defined directly above;
Ring A is phenyl either unsubstituted or substituted at one to two ring carbon atoms with $R^4$ wherein $R^4$ is halo;
R' is selected from H, $(C_1-C_6)$alkyl, $—(CH_2)_nM$ and $—(CH_2)_nW$, wherein;
n is selected from 0, 1 and 2;
M is phenyl which is either unsubstituted or substituted with 1 or 2 groups chosen independently from $—O-(C_1-C_4)$alkyl, $—O-(C_0-C_6)$alkylphenyl, —OH, -halo, —CN, $—CF_3$, or $-(C_1-C_4)$alkyl; or
M is heteroaryl wherein heteroaryl is pyridyl or pyridyl substituted by one alkoxy group;
W is selected from OH, $SO_mR'$, or NR'R" with the proviso that n is 1 or 2, and
R' and R" are independently selected from H, $(C_1-C_4)$ alkyl, and phenyl$(C_0-C_4)$alkyl- wherein phenyl is optionally substituted at one carbon atom with $O-(C_1-C_4)$alkyl.

More particularly preferred compounds of the formula B above are those wherein:
W, n and m are as defined directly above;
Ring A is phenyl substituted at one to two ring carbon atoms with $R^4$ wherein $R^4$ is chloro;
$R^1$ is selected from H, butyl, 1-methylbutyl, hexyl and $—(CH_2)_nM$, wherein;
M is phenyl which is either unsubstituted or substituted with 1 or 2 groups chosen independently from methoxy, phenoxy, —OH, fluoro, bromo, chloro, —CN, $—CF_3$, or methyl; or
M is heteroaryl wherein heteroaryl is pyridyl substituted by one methoxy group;
$R^3$ is selected from H, or $—(CO)R^6$ wherein $R^6$ is selected from methyl, ethyl, methoxycarbonylethyl, and phenyl; and
R' and R" are independently selected from H, methyl, ethyl and phenyl substituted at one carbon atom with methoxy.

Preferred species of compounds of formula B are selected from the following and from those which are described hereinafter on pages 23–24.
7-chloro-4-hydroxy-2-(4'-methoxy-2'-methylphenyl)-5,10-dihydro-2H-pyridazino[4,5-b]quinoline-1-one;
7-chloro-4-hydroxy-2-(3',5'-difluoromethyl)-5,10-dihydro-2 H-pyridazino[4,5-b]quinoline-1-one;
7-chloro-4-hydroxy-2-(hexyl)-5,10-dihydro-2H-pyridazino [4,5-b]quinoline-1-one;
7-chloro-4-hydroxy-2-(2-(methylthio)ethyl)-5,10-dihydro-2H-pyridazino[4,5-b]quinoline-1-one;
7-chloro-4-hydroxy-2-(2'-methylphenyl)-5,10-dihydro-2H-pyridazino[4,5-b]quinoline-1-one;
7-chloro-4-hydroxy-2-(3'-methoxyphenyl)-5,10-dihydro-2H-pyridazino[4,5-b]quinoline-1-one;

7-chloro-4-hydroxy-2-(butyl)-5,10-dihydro-2H-pyridazino[4,5-b]quinoline-1-one;

7-chloro-4-hydroxy-2-(2'-methoxybenzyl)-5,10-dihydro-2H-pyridazino[4,5-b]quinoline-1-one;

7-chloro-4-hydroxy-2-(1-methylbutyl)-5,10-dihydro-2H-pyridazino[4,5-b]quinoline-1-one;

7-chloro-4-phenylcarbonyloxy-2-(4'-methylphenyl), 5,10-dihydro-2H-pyridazino[4,5-b]quinoline-1-one;

7-chloro-4-ethylcarbonyloxy-2-(4'-methylphenyl)-5,10-dihydro-2H-pyridazino[4,5-b]quinoline-1-one;

7-chloro-4-methylcarboxyloxy-2-(4'-methylphenyl)-5,10-dihydro-2H-pyridazino[4,5-b]quinoline-1-one;

7-chloro-4-methoxycarbonylethylcarbonyloxy-2-(4'-methylphenyl)-5,10-dihydro-2H-pyridazino[4,5-b]quinoline-1-one, and 7-chloro-4-hydroxy-2-(4'-hydroxyphenyl)-5,10-dihydro-2H-pyridazino[4,5-b]quinoline-1-one.

The present invention may also relate to intermediate compounds of formula E or F wherein F is defined as E except $R^1$ is linked to N in place of M,

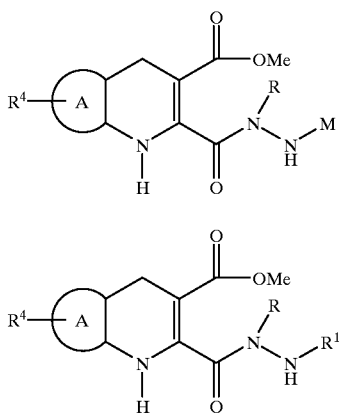

wherein:
Ring A, $R^4$, $R^1$ and M are as heretofore defined.
R is selected from H or ($C_1$–$C_4$)alkyl or benzyl;

The present invention may also relate to a compound of formula G or H:

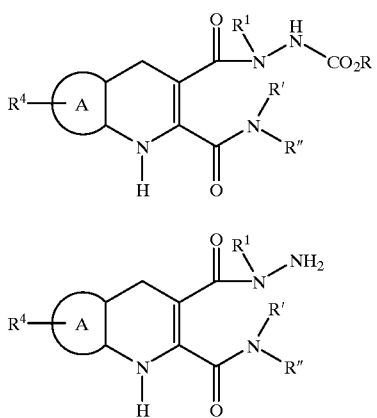

wherein:
Ring A, $R^4$, $R^1$, R, R', R" and M are as heretofore defined.

The present invention also relates to a pharmaceutical composition comprising a compound of formula A and a pharmaceutically acceptable excipient or diluent.

It further relates to a pharmaceutical composition comprising a compound of formula B and a pharmaceutically acceptable excipient or diluent and to a pharmaceutical composition comprising a compound according to formula A', B', C or C' and a pharmaceutically acceptable excipient or diluent.

The invention further relates to a method for the treatment of neurological disorders comprising administering to a mammal in need of such treatment an effective amount of a compound of the formula A, A' or B.

The invention further relates to the use of a compound of the formula A, A' or B for the preparation of a medicament for the treatment of neurological disorders.

The present invention also relates to a method of treating or preventing ischemic damage in a patient in need of such treatment comprising administering a pharmaceutically effective amount of a compound of formula B to said patient.

The invention further relates to a method of treating or preventing neurological damage associated with excitatory amino acids in a patient in need of such treatment comprising administering a pharmaceutically effective amount of a compound of formula B to said patient.

The invention also relates to a method of treating stroke or epileptic convulsions or diseases or disorders associated with excessive calcium influx in the brain caused by excitatory amino acids comprising administering to a patient in need of treatment thereof a pharmaceutically effective amount of a compound of formula B.

The invention further relates to a process for producing a compound of formula B or B', comprising:

treating any of the compounds produced in steps (a)–(i) with a reducing agent under suitable conditions to form a compound of formula B and further treating a compound of formula B with a reducing agent under the appropriate conditions to form a compound of formula B' or treating a compound produced in steps (a)–(i) with a reducing agent under the appropriate conditions to form a compound of formula B' wherein steps (a)–(i) comprise:

(a) treating a compound of formula V or XIV with an acid selected from a lower ($C_1$–$C_4$)alkyl sulfonic acid in a suitable organic solvent; or (b) treating a compound of formula IV' with an alkylaryl or alkylheteroarylhydrazine in a polar solvent and a mild acid; or (c) treating a compound of formula VI' wherein Y is selected from —OH, —SH or NHR wherein R is ($C_1$–$C_4$)alkyl with a reagent selected from (i) $R^2$NC(O)Cl; or (ii) RC(O)X; or (iii) ROC(O)Cl; or (iv) HBr/NaCN/$H_2O$ or ROH; or (v) RNCO or R'R'NC(O)Cl or other electrophilic group as recited herein to form, in particular, a ompound of formula XXI; or (d) treating a compound of formula XV wherein X is halogen with a nucleophilic reactant selected from heterocycle or benz or heteroarylbenz derivatives thereof; or (e) treating a compound of formula XXII with a substituted hydrazine to form a ompound of formula XVII in an organic solvent under the appropriate conditions; or (f) treating a compound of formula XVIII with a coupling reagent selected from a diimide with a disubstituted hydrazine of the formula $R^1$—NHNHC(O)Ot-butyl in an organic solvent in the presence of an appropriate acid or (g) further treating a compound of formula II as claimed in claim 2 wherein the compound contains a phenyl ring substituted with a methoxy group or groups with an acid to form a phenolic substituent or substituents or further treating a compound of formula II wherein the compound is a non-salt form with a pharmaceutically acceptable base to form a pharmaceutically acceptable salt or further treating a compound of formula II wherein the compound contains a phenyl ring substituted with a cyano group or groups with (i) a base to form a carboxlic acid substituent or substituents or (ii) an acid to form an amide substituent or (iii) an azide to form a tetrazole substituent wherein the carboxlic acid moiety may be further treated with a halogenating agent and a substituted amine of formula HNR'R" to form a substituted amide substituent or the carboxylic acid moiety may be further treated with an $(C_1-C_6)$ alcohol in the presence of an acid to form an $(C_1-C_6)$ substituted ester, or (h) further treating a compound of formula II wherein the compound contains an oxozolidinedione with a base in aqueous solution to form an amido alcohol substituent as W off the $(CH_2)_n$ carbon chain with n equal to 1–4; or (i) further treating a compound of formula II wherein the compound contains a sulfide moiety with an oxidizing agent under the appropriate conditions to form an SO or $SO_2$ moiety; or (j) treating a compound of formula i or J with an acid selected from a lower $(C_1-C_4)$alkyl sulfonic acid in a suitable organic solvent; or (k) treating a compound of formula K or K' with an alkylaryl or alkylheteroarylhydrazine in a polar solvent and a mild acid; or (l) treating a compound of formula L or L' wherein Y is selected from —OH, —SH or NHR wherein R is $(C_1-C_4)$alkyl with a reagent selected from (i) $R^2NC(O)Cl$; or (ii) RC(O)X; or (iii) ROC(O)Cl; or (iv) HBr/NaCN/$H_2O$ or ROH; or (v) RNCO or R'R'NC(O)Cl or other electrophilic group as recited herein to form, in particular, a compound of formula M or M'; or (m) treating a compound of formula D wherein X is halogen with a nucleophilic reactant selected from heterocycle or benz or heteroarylbenz derivatives thereof; or (n) treating a compound of formula N or N' with a substituted hydrazine to form a compound of formula O or O' in an organic solvent under the appropriate conditions; or (o) treating a compound of formula P or P' with a coupling reagent selected from a diimide and with a disubstituted hydrazine of the formula $R^1$—NHNHC(O)Ot-butyl in an organic solvent in the presence of an appropriate acid or (p) further treating a compound of formula B wherein the compound contains a phenyl ring substituted with a methoxy group or groups with an acid to form a phenolic substituent or substituents or further treating a compound of formula B wherein the compound is a non-salt form with a pharmaceutically acceptable base to form a pharmaceutically acceptable salt or further treating a compound of formula B wherein the compound contains a phenyl ring substituted with a cyano group or groups with (i) a base to form a carboxlic acid substituent or substituents or (ii) an acid to form an amide substituent or (iii) an azide to form a tetrazole substituent wherein the carboxlic acid moiety may be further treated with a halogenating agent and a substituted amine of formula HNR'R" to form a substituted amide substituent or the carboxylic acid moiety may be further treated with a $(C_1-C_6)$alcohol in the presence of an acid to form an substituted $(C_1-C_6)$ester, or (q) further treating a compound of formula B wherein the compound contains an oxozolidine dione with a base in aqueous solution to form an amido alcohol substituent as W off the $(CH_2)_n$ carbon chain with n equal to 1–4; or (r) further treating a compound of formula B wherein the compound contains a sulfide moiety with an oxidizing agent under the appropriate conditions to form an SO or $SO_2$ moiety.

The invention further relates to a process for producing a compound of formula B according to certain steps recited above as shown in the examples wherein the compounds are selected from:

7-chloro-4-hydroxy-5,10-dihydro-2-(4'-methylphenyl) pyridazino[4,5-b]quinoline-1-one;

7,9-dichloro-2,3,5,10-tetrahydropyridazino[4,5-b] quinoline-1,4-dione;

7-chloro-4-hydroxy-2-phenyl-5,10-dihydro-2H-pyridazino [4,5-b]quinoline-1-one;

7-chloro-4-hydroxy-2-(4'-methoxyphenyl)-5,10-dihydro-2H-pyridazino[4,5-b]quinoline-1-ne;

7-chloro-2,3,5,10-tetrahydropyridazino[4,5-b]quinoline-1,4-dione;

7,9-dichloro-4-hydroxy-2-(4'-methylphenyl)-5,10-dihydro-2H-pyridazino[4,5-b]quinoline-1-one;

7-chloro-4-hydroxy-2-hydroxyethyl-5,10-dihydro-2H-pyridazino[4,5-b]quinoline-1-one;

7-chloro-4-hydroxy-2-(N-ethyl-4'-methoxyaniline)-5,10-dihydro-2H-pyridazino[4,5-b]quinoline-1-one;

7-chloro-4-hydroxy-2-(4'-fluorophenyl)-5,10-dihydro-2H-pyridazino[4,5-b]quinoline-1-one;

7-chloro-4-hydroxy-2-(4'-methoxy-3-pyridyl)-5,10-dihydro-2H-pyridazino[4,5-b]quinoline-1-one;

7-chloro-4-hydroxy-2-(3',4'-dimethoxyphenyl)-5,10-dihydro-2H-pyridazino[4,5-b]quinoline-1-one;

7-chloro-4-hydroxy-2-(2',4'-dimethylphenyl)-5,10-dihydro-2H-pyridazino[4,5-b]quinoline-1-one;

7-chloro-4-hydroxy-2-(3'-methoxyphenyl)-5,10-dihydro-2H-pyridazino[4,5-b]quinoline-1-one;

7-chloro-4-hydroxy-2-(4'-bromo-2'-methoxyphenyl)-5,10-dihydro-2H-pyridazino[4,5-b]quinoline-1-one;

7-chloro-4-hydroxy-2-(ethylthioethyl)-5,10-dihydro-2H-pyridazino[4,5-b]quinoline-1-one;

7-chloro-4-hydroxy-2-(2',5'-dimethylphenyl)-5,10-dihydro-2H-pyridazino[4,5-b]quinoline-1-one;

7,9-dichloro-4-hydroxy-2-(4'-methoxyphenyl)-5,10-dihydro-2H-pyridazino[4,5-b]quinoline-1-one;

7-chloro-4-hydroxy-2-(4'-methylbenzyl)-5,10-dihydro-2H-pyridazino[4,5-b]quinoline-1-one;

7,9-dichloro-4-hydroxy-2-(2',4'-dimethylphenyl)-5,10-dihydro-2H-pyridazino[4,5-b]quinoline-1-one;

7-chloro-4-hydroxy-2-(4'-bromo-2'-methylphenyl)-5,10-dihydro-2H-pyridazino[4,5-b]quinoline-1-one;

7-chloro-4-hydroxy-2-(2'-fluorobenzyl)-5,10-dihydro-2H-pyridazino[4,5-b]quinoline-1-one;

7-chloro-4-hydroxy-2-(3'-chlorobenzyl)-5,10-dihydro-2H-pyridazino[4-5-b]quinoline-1-one;

7-chloro-4-hydroxy-2-(3'-phenoxyphenyl)-5,10-dihydro-2H-pyridazino[4,5-b]quinoline-1-one;

7-chloro-4-hydroxy-2-(2'-cyano benzyl)-5,10-dihydro-2H-pyridazino[4,5-b]quinoline-1-one; and 7-chloro-4-hydroxy-2-(3'-methylphenyl)-5,10-dihydro-2H-pyridazino [4,5-b]quinoline-1-one.

The invention also relates to the use of a compound of formula B or B' in medicine and to diseases or disorders associated with excitatory amino acids.

The invention also relates to the use of a compound of formula B or B' for the treatment of stroke or epileptic convulsions or disorders or conditions associated with excessive influx of calcium ions in the brain.

The present invention also relates to compounds which are useful as key intermediates in the production of glycine receptor antagonists as defined above wherein W is equal to halo species such as Cl, Br, F or I wherein n is greater than zero. In addition, compounds obtained through a novel process for the production of pyridazinoquinolinediones ("PQDs") as herein defined with $R^1$ selected from aryl or heteroaryl as defined above are key intermediates in the production of said compounds. These key intermediates are 3-carboalkoxy-quinoline-2-carboxylic acid N-2-aryl (or heteroaryl) hydrazides which are used to produce the above aryl or heteroaryl species wherein aryl and heteroaryl are as defined above. Other key intermediates include 3-carboxylic acid quinoline 2-pyrrolidineamide intermediates which are utilized to react with BOC-protected aryl, heteroaryl or substituted alkylhydrazines to form after coupling with dicyclohexyldiimide or diisopropyldiimide, in a polar solvent such as THF, methanol, diethylether, dioxane, $CH_2Cl_2$, $CH_3CN$ or DMF and an acid (e.g. $CH_3SO_3H$) another key intermediate—a 2-pyrrolidiiocarbamide 3 carboxylic acid-N-1 aryl, heteroaryl, substituted alkyl, aryl alkyl or heteroaryl alkyl hydrazide, which after deprotection or removal of the BOC or other bulk N-protection group, leads selectively to the N-2 substituted PQD. The pyrrolidine may be substituted with an equivalent amine which produces an amide with limited steric hindrance and which acts as an appropriate leaving group.

EPO publication number 0 516 297 A1 describes certain pyridazinediones. In addition, the compounds (1) thieno[2',3':5,6]pyrido[2,3-d]pyridazine-5,8,9(4H,6H,7H)-trione and (2) thieno[3',2':5,6]pyrido[2,3-d]pyridazine-4,5,8(6H,7H,9H)-trione are known, for example from J. Heterocyclic Chem., 28, 205, (1991).

Other pyridazinedione compounds are known from, for example, Beilstein's Handbuch der Organischen Chemie; Godard et. al., Bull. Soc. Chim. Fr., 1588, (1972); and Reid et. al., Chem. Ber., 85, 204, (1952). The compounds of the present invention, on the other hand, relate to novel 2- or 3-substituted pyridazinediones or tautomers thereof as shown above in formula A or A'.

Particular subgroups within the above broadly defined group of compounds include those compounds having the specific formulae B or C.

The present invention also relates to pharmaceutical compositions of a compound of formula B as defined above and a pharmaceutically acceptable excipient. In addition, the present invention relates to important intermediates which are useful in the synthesis of a compound of formula B wherein L in the above formula is chosen from halo (Br, Cl, F or I) and n is greater than zero. This intermediate is useful in the production of certain glycine receptor antagonists of formula B.

The present invention also relates to pharmaceutical compositions of a compound of formula C as defined above and a pharmaceutically acceptable excipient.

In addition, the present invention relates to important intermediates which are useful in the synthesis of a compound of formula C wherein L in the above formula is chosen from halo (Br, Cl, F or I). This intermediate is useful in the production of certain glycine receptor antagonists of formula C.

More particular subgroups include those compounds having the specific formulae B and C, wherein Ring A is chosen from phenyl or substituted phenyl wherein the phenyl ring is mono, di or tri-substituted with halo, nitro or simple $(C_1–C_4)$alkyl including methyl, ethyl or propyl.

Preferably, the present invention relates to compounds of formula B or pharmaceutically acceptable salts thereof wherein Ring A is chosen from an ortho fused phenyl, 7-chlorophenyl, 7,9-dichlorophenyl, 7-chloro-9-methylphenyl, 7-methyl-9-chlorophenyl, 7,9-dimethylphenyl, 7-chloro-8-nitrophenyl, 7,9-dichloro-8-nitrophenyl, 7-chloro-9-ethylphenyl wherein the numeric designations refer to the position on the final pyridazino quinoline ring system;

Advantageously, for the compounds of formula B, n is equal to zero, $R^3$ is H and L is selected from: phenyl, 4-methoxyphenyl, 4-hydroxyphenyl, 4-chlorophenyl, 4-methylphenyl, 4-isopropylphenyl, napthyl, 4-fluorophenyl, 4-bromophenyl, 2-methoxyphenyl, 2-hydroxyphenyl, 3-methoxyphenyl, 3-hydroxyphenyl, 4-trifluoromethoxyphenyl, 3-chloro-4-methoxyphenyl, 5-methoxy-3-pyridyl, 4-$SO_m$R'phenyl wherein m is 0, 1 or 2 and R' is methyl; 3-chlorophenyl, 3-chloro-4-hydroxyphenyl, 2-methyl-4-chlorophenyl, 3-methylphenyl, 2-methylphenyl, 3-fluorophenyl, 2,4-difluorophenyl, 3,5-trifluoromethylphenyl, 3-nitrophenyl, 2-fluorophenyl, 2,4-dimethylphenyl, 3-chloro-4-methylphenyl, 4-trifluoromethylphenyl, 4-iodophenyl, 3,4-dimethylphenyl, 3,4-dimethoxyphenyl, 2-methyl-4-methoxyphenyl, 2-methoxy-4-bromophenyl, 2-methyl-4-hydroxyphenyl, 4-ethylphenyl, 2,3-dimethylphenyl, 3,4-dihydroxyphenyl, 2,4-dimethoxyphenyl, 2,4-dichlorophenyl, 4-nitrophenyl, 2,5-dimethoxyphenyl, 2,5-dimethylphenyl, 4-oxybenzylphenyl, 2,5-dihydroxyphenyl, 4-vinylphenyl, 2,5-difluorophenyl, 2-methyl-4-fluorophenyl, 3,5-dimethoxyphenyl, 4-carboxyphenyl, 4-formamidophenyl, 4-(N,N-diethylformamido)phenyl, 4-cyanophenyl, or 4-tetrazolephenyl.

Advantageously, the present invention also relates to compounds of formula B wherein n is equal to 1, R3 is H and L is selected from any of the members identified above for n equal to zero and, more particularly to groups selected from 1-fluorophenyl, 4-cyanophenyl, 4-trifluoromethylphenyl, 4-methylphenyl, pentafluorophenyl or 3,5-ditrifluoromethylphenyl or to compounds of formula B wherein n is equal to three and L is selected from any group designated for n equal to zero or one, but more particularly to a group selected from phenyl or a phenyl substituted with a typical aromatic substituent.

The substituted alkyl($C_1–C_6$)aryls disclosed herein which are particularly useful are those containing phenyl substituents which increase lipophilicity to enhance red nucleus activity. For example, the fluorinated, alkylfluorinated, ($C_1–C_4$)alkyl or mono-halogenated benzyl compounds have enhanced activity. The ($C_1–C_6$)alkyl groups substituted with a terminal $CF_3$ group are particularly useful because of their unexpected solubility properties and are also useful because of their lipophilicity.

The pyridyl rings attached via a carbon atom on the pyridyl ring to the $(CH_2)_n$ group of a compound of formula B have glycine receptor antagonist activity.

The present invention also preferably relates to a compound of formula B wherein n is equal to two, $R^3$ is H and a heterocyclic moiety as described herein is bonded to the N-2-ethyl carbon and is selected from 1-phthalimido, 4-phenylpiperazine, succinimide, 3,3-dimethyl-2,5-oxazolidinedione, 1-methylpyrollidine, 3-methyl-3-phenyl-2,5-oxazolidinedione, 3-N-methyl-3,5-imidazolidinedione, 4,4-dimethyl-2,5-imidazolidinedione, 4,4-diphenyl-2,5-imidazolidinedione, 2,4-thiazolidinedione, 3,4-pyridinedicarboximide, orthobenzoicsulfimide (saccharine), 4-cyclohexylspiral-2,5-oxazolidinedione, isatoic anhydride, benzo[e][1,3]oxazine-2,4-dione, 4-phenyl-2,5-oxazolidinedione or 3-hydroxy-3-methyl-2-pyrrolidinone. The preferred compounds for which n is equal to one and L is heterocycle include groups selected from tetrahydrofuran, piperidine, N-methylpiperidine, tetrahydropyran, 1,3-dioxane, benzo-1,4-dioxane or orthobenzoicsulfimide.

The present invention also preferably relates to compounds of formula B wherein $R^1$ is equal to $(CH_2)_nL$ and wherein n is equal to one, $R^3$ is H and L is equal to a heteroaryl selected from thiophene or pyridyl or furan or substituted versions thereof wherein the substituents are selected from typical aromatic substituents (e.g. hydroxy, halo, $(C_1-C_6)$alkyl, phenyl or heteroaryl) or to those groups selected from imidazole, thiazole, thiadiazole, pyridopyridine, pyrimidine, pyrazine, pyridazine, benzothiophene, furan, benzofuran, indole, or triazole or substituted versions thereof. The preferred groups when n is equal to two and wherein the heteroaryl group is attached to the 2-ethyl carbon include members selected from imidazole, triazole, tetrazole or pyridine.

The present invention also relates advantageously to a compound of formula B wherein n is equal to two, $R^3$ is H and L is equal to W wherein W is selected from the group consisting of: hydroxy, acetoxy, benzoylamido, 2-hydroxy-2-methylpropamido, 4-methoxyaniline, 1-formamidocyclohexanol, 2-hydroxybenzamido, biphenylhydroxyacetamido, —S—$CH_3$, —$SO_2$—$CH_3$, —S-4-methoxyphenyl, S-cyclopentyl, —$SO_2$-ethyl, —S-ethyl, —S-butyl, —$SO_2$-butyl, or —S-propyl. In addition, these groups may be selected from —O-phenyl, halo, —$CH_2$—COOR', —$CH_2$CONR'R", —$OCH_3$, —$OCH_2CH_2OCH_3$, —$OCH_2CH_2OCH_2CH_3$, —O-2-methoxyphenyl, —$SO_2$Ph, —$SO_2$NR'R", —$CF(CF_3)_2$, —$CF_2CF_3$, —$CF_2CF_2CF_3$, —$OC_2H_5OC_2H_5$, —$CH_2$NR'R" and —$CH_2CH_2COCH_3$.

The present invention also relates to pharmaceutical compositions containing a preferred compound of formula B as shown above and a pharmaceutically acceptable carrier.

It will be appreciated that the formulae described herein can be drawn in various tautomeric and positional isomeric forms, as discussed below.

The present invention includes such alternate forms unless otherwise indicated, also includes salts thereof, especially the pharmaceutically acceptable addition salts.

Scheme 8 (in part) shows that some of the compounds disclosed herein can exist and be drawn in various true tautomeric forms (i.e., imine to enamine conversion in the B ring).

It will further be appreciated by those skilled in the art that certain compounds of formula B may contain an asymmetrically substituted carbon atom, and accordingly may exist in, and be isolated in, optically-active and racemic forms. In addition, it will be appreciated that certain compounds of formula B, for example, those containing a double bond, may exist in, and be isolated in, separate stereoisomeric forms ('E' and 'Z') about that group. Some compounds may exhibit polymorphism. It is to be understood that the present invention encompasses any racemic, optically-active, polymorphic or stereoisomeric form, or mixtures thereof, which form possesses properties useful in the treatment of neurodegenerative disorders, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine neuroprotective properties by the standard tests described hereinafter.

The invention further provides a method for the treatment of neurological disorders, comprising administering to a mammal in need of such treatment an effective amount of a compound according to the invention as defined above, or a pharmaceutically acceptable salt thereof, or a composition as defined above. The invention also encompasses a method of antagonizing an NMDA receptor in mammals comprising administering a pharmaceutically effective amount of the compound or its salt as claimed herein or a pharmaceutical composition as recited herein to a patient in need of treatment thereof. The preferred therapeutic treatment area is prevention and/or treatment of stroke. A pharmaceutically effective amount of a compound as claimed and disclosed in the present invention may be administered immediately after an ischemic event to prevent cell damage and/or cell death.

The present invention is also directed to a method of preventing and/or treating damage induced by the excitatory amino acids such as L-glutamate.

The invention also relates to a method of preventing the excessive influx of calcium ions in central neurons.

The invention relates to a method of preventing ischemic neuronal injury following transient global ischemia and a method of reducing infarct volume following focal ischemic insults by treating a patient in need of treatment thereof with a pharmaceutically effective amount of a compound of formula A or B wherein ring A and $R^1$ and $R^2$ are as defined herein.

In addition to being useful in the treatment of acute stroke patients, the compounds and compositions of the invention may be extremely beneficial in preventing neurological morbidity during cardiac resuscitation or administered as cerebral prophylatics during high-risk surgery.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

The term "heteroaryl" includes those heteroaromatic groups of benz derivatives thereof where are specifically or generally described or disclosed in this specification.

Particular values of $(C_1-C_4)$alkyl include methyl, ethyl, propyl, isopropyl, butyl, isobutyl, sec-butyl, and tert-butyl.

Particular values of $(C_2-C_4)$alkenyl or -alkynyl include vinyl, 2-propenyl (i.e. allyl), 2-propynyl, (i.e. propargyl), 2-butenyl, and 3-butenyl.

Particular values of $(C_1-C_4)$alkoxy include methoxy, ethoxy, propoxy, isopropoxy, butoxy, isobutoxy, and t-butoxy.

Particular values of $(C_1-C_{12})$alkyl include methyl, ethyl, propyl, isopropyl, butyl, isobutyl, sec-butyl, text-butyl, pentyl, isopentyl, neopentyl, hexyl, isohexyl, heptyl, isoheptyl, octyl, 2,2,4-trimethylpentyl, nonyl, isononyl, decyl, isodecyl, undecyl, isoundecyl, dodecyl and isododecyl.

Particular values of $(C_2-C_{12})$alkenyl or -alkynyl include vinyl, 2-propenyl (i.e. allyl), 2-propynyl (i.e. propargyl), but-2-enyl, 2-pentenyl, 3-pentenyl, 4-pentenyl, 4-pentynyl, 5-hexenyl, 5-hexynyl, 6-heptenyl, 6-heptynyl, 7-octenyl, 7-octynyl, 11-dodecenyl, and 11-dodeynyl.

Particular values of $(C_1-C_6)$alkyl include methyl, ethyl, propyl, isopropyl, butyl, isobutyl, sec-butyl, tert-butyl, 1-methylbutyl, pentyl, isopentyl, neopentyl, hexyl, isohexyl.

Particular values of $(C_2-C_6)$alkenyl or -alkynyl include vinyl, 2-propenyl (i.e. allyl), 2-propynyl (i.e. propargyl), but-2-enyl, 2-pentenyl, 3-pentenyl, 4-pentenyl, 4-pentynyl, 5-hexenyl, 5-hexynyl.

Particular values of phenyl substituted with from 0–4 substituents may include but are not limited to phenyl; 2-, 3-, and 4-halophenyl; 2-, 3-, and 4-aminophenyl; 2-, 3-, and 4-hydroxyphenyl; 2-, 3-, and 4-cyanophenyl; 2-, 3-, and 4-nitrophenyl; 2-, 3-, and 4-methylphenyl; 2-, 3-, and 4-ethylphenyl; 2-, 3-, and 4-propylphenyl; 2,3 or 4-isopropylphenyl; 2-, 3-, and 4-methoxyphenyl; 2-, 3-, and 4-ethoxyphenyl; 2-, 3-, and 4-propoxyphenyl; and 3,5-dihalophenyl, 3-halo-4-hydroxyphenyl, and 3,5-dihalo-4-hydroxyphenyl and phenyl substituted at 1, 2 or 3 carbon atoms with methoxyethyloxy, methoxyethyloxyethyloxy, N,N-dimethylethyloxy, and N,N-dimethylethylaminyl; 3,4-dimethoxy; 3,4-dihydroxy; 3,5-dimethoxy; 3,5-dihydroxy or 2,3,4-SMe or 2,3,4-SH and further includes groups selected from 4—$(SO_2CH_3)$phenyl, 2-methyl-4-chlorophenyl, 2,4-dihalophenyl, 4(tetrazole)phenyl, 3,5-trifluoromethylphenyl, 2,4-dimethylphenyl, 3-halo-4-methylphenyl, 4-trifluoromethylphenyl, 3,4-dimethylphenyl, 2-methyl-4-methoxyphenyl, 2-methoxy-4-halophenyl, 2-methyl-4-hydroxyphenyl, 2,3-dimethylphenyl, 2,4-dimethoxyphenyl, 2,5-dimethoxyphenyl, 2,5-dimethylphenyl, 4(benyloxy)phenyl, 4-(ethoxy)phenyl, 2,5-dihydroxyphenyl, 4-vinylphenyl, 2,5-dihalophenyl, 2-methyl-4-fluorophenyl, or 2-, 3- or 4-(CONR'R")phenyl.

Particular values of phenyl$(C_1-C_4)$alkyl substituted with from 0–4 substituents may include benzyl, phenylethyl, phenylpropyl, phenylbutyl; 2-, 3-4 and 5-halobenzyl; 2-, 3- and 4- $CF_3$-benzyl, 2-, 3- and 4-aminobenzyl; 2-,3- and 4-cyanobenzyl, 2-, 3- and 4-nitrobenzyl, 2-, 3- and 4-methylbenzyl; 2-, 3- and 4-ethylbenzyl; 2-, 3- and 4-propylbenzyl; 2-, 3- and 4-hydroxybenzyl; 2-, 3- and 4-methoxybenzyl; 2-, 3- and 4-ethoxybenzyl; 2-, 3- and 4-propoxybenzyl; and 3,5-dihalobenzyl, 3-halo-4-hydroxybenzyl, 3,5-di$CF_3$benzyl and 3,5-dihalo-4-hydroxybenzyl or 2,3,4,5,6-pentahalobenzyl; and phenyl $(C_1-C_4)$alkyl substituted with methoxyethyloxy, methoxyethyloxyethyloxy, N,N-dimethylethyloxy, and N,N-dimethylethylaminyl; 3,4-dimethoxy; 3,4-dihydroxy; 3,5-dimethoxy; 3,5-dihydroxy or 2,3,4-SMe or 2,3,4-SH.

Particular values of 4- to 7-membered rings containing nitrogen may include piperidino, pyrrolidinyl, and azetidinyl.

Particular values of heterocyclic species with 2 heteroatoms include piperazinyl, morpholinyl, oxazolinyl or thiazinyl. Particular values of heterocycles or substituted derivatives thereof include 2-pyrrolidone, succinimide, oxazolidone, 2,5-oxazolidinedione, 2,4-thiazolidinedione, 2,4-imidazolidinedione and various benz derivatives including phthalimido, isatoic anhydride, benzo[e][1,3]oxazine-2, 4-dione, 3,4-pyridinedicarboximide, or orthobenzoicsulfimide.

More particular values of halo include chloro and bromo.

More particular values of perfluoro$(C_1-C_3)$alkyl include trifluoromethyl and pentafluoroethyl.

More particular values of 4- to 7-membered rings containing nitrogen include piperidino, piperazinyl and pyrrolidinyl.

More particular values Of $(C_1-C_3)$alkyl substituted with a trifluoromethyl group include trifluoromethylmethyl and 2-trifluoromethylethyl.

More particular values of heteroaryl include tetrazole, furan, thiophene, diazole, imidazole, triazole, pyridine, pyrimidine, pyridazine and pyrazine.

More particular values of m include 0–2.

More particular values of n include 0–2.

More particular values of phenyl substituted with from 0–3 substituents may include phenyl; 2- and 4-halophenyl; 2- and 4-aminophenyl; 2-, 3- and 4-hydroxyphenyl; 2-, 3- and 4-methoxyphenyl; 2,4-dihalophenyl; 3,5-dihalophenyl; 2,6-dihalo-4-hydroxyphenyl, 2-halo-4-methylphenyl; 2-methoxy-4-methylphenyl; 2-methyl-4-methoxyphenyl; 3-hydroxy-4-methyl phenyl; 2-hydroxy-4-methyl phenyl, 2-methyl-4-chlorophenyl, 2,4-dimethylphenyl, 3,4-dimethoxyphenyl, 2-methyl-4-methoxyphenyl, 3,4-dihydroxyphenyl or 2,4-dimethylphenyl; and includes those values specifically exemplified in the examples.

More particular values of phenyl$(C_1-C_4)$alkyl substituted with 0–3 substituents may include benzyl; phenylethyl; 2- and 4-halobenzyl; 2- and 4-cyanobenzyl; 2- and 4-nitrobenzyl; 2- and 4-methoxybenzyl; 2,4-dihalobenzyl, 3,5-dihalobenzyl; and 2,6-dihalo-4-hydroxybenzyl. The corresponding phenethyl isomers may also be included.

Preferred values of $R^1$ include hydrogen, hydroxyethyl, (methoxyaniline)ethyl, phenoxyphenyl, alkoxyhalophenyl, dimethoxyphenyl, methoxypyridyl, dialkylphenyl, halomethylphenyl, halophenyl, (alkylthio)ethyl, phenyl, methoxyphenyl, halo, alkyl, trifluoromethyl or cyano substituted benzyl, fluorophenyl, methylphenyl, or $(C_1-C_4)$alkylphenyl.

More preferred values of $R^1$ include 2-hydroxyethyl, 2-(4'-methoxyaniline)ethyl, phenyl, 4-methoxyphenyl, 2-methyl-4-bromo-phenyl, benzyl, 4-fluorophenyl, 4-methylphenyl, 2-(4'-methoxyaniline)N-ethyl, 3,4-dimethoxyphenyl, 2-4'-methoxy-3-pyridyl, 2,4-dimethylphenyl, 3-methoxyphenyl, 2(ethylthio)ethyl, 2,5-dimethylphenyl, 2-fluorobenzyl, 4-methylbenzyl, 2-cyanobenzyl, 3-chlorobenzyl, 2-methyl-4-methoxyphenyl, 3-phenoxyphenyl, 3,5-ditrifluoromethylbenzyl, 3-methylphenyl, 4-iodophenyl, 2(methylthio)ethyl, or 2-methylbenzyl. Of course, the preferred values for Z (for starting material), Ring A, $R^1$ and $R^2$ and the other designated values in formulae A, B, A', B' etc. include those values or groups which are specifically exemplified in the relevant examples and/or in the appropriate schemes.

Preferred values for $R^3$ include hydrogen and $(COR^6)$.

More preferred values for $R^3$ are hydrogen.

Preferred values for $R^5$ include H, $(C_1-C_4)$alkyl or benzyl.

More preferred values for $R^5$ are H.

Preferred values for R include $(C_1-C_{12})$alkyl or phenyl.

More preferred values for $R^6$ are hydrogen.

Preferred values for $R^6$ include those groups designated as particular values for $(C_1-C_{12})$alkyl or for $(C_2-C_{12})$alkenyl or -alkynyl and substituted versions thereof and also include phenyl and substituted version thereof. More preferred values include hydrogen, methyl, phenethyl, phenyl, isobutyl, tert-butyl, isopropyl, ethyl, or benzyl.

Preferred values of $R^4$ include hydrogen, fluoro, chloro, bromo, iodo, amino, methyl, ethyl, propyl, allyl, propargyl, trifluoromethyl, pentafluoroethyl, trifluoromethylmethyl, nitro, methoxy, ethoxy, propoxy, and cyano.

More preferred values of $R^4$ include hydrogen, fluoro, chloro, bromo, iodo, methyl, ethyl, trifluoromethyl, nitro, methoxy, amino, and cyano.

Preferred compounds having formula B include:

7-chloro-4-hydroxy-5,10-dihydro-2-(4'-methylphenyl) pyridazino[4,5-b]quinoline-1-one;

7,9-dichloro-2,3,5,10-tetrahydropyridazino[4,5-b] quinoline-1,4-dione;

7-chloro-4-hydroxy-2-phenyl-5,10-dihydro-2H-pyridazino [4,5-b]quinoline-1-one;

7-chloro-4-hydroxy-2-(4'-methoxyphenyl)-5,10-dihydro-2H-pyridazino[4,5-b]quinoline-1-one;

7-chloro-2,3,5,10-tetrahydropyridazino[4,5-b]quinoline-1,4-dione;

7,9-dichloro-4-hydroxy-2-(4'-methylphenyl)-5,10-dihydro-2H-pyridazino[4,5-b]quinoline-1-one;

7-chloro-4-hydroxy-2-hydroxyethyl-5,10-dihydro-2H-pyridazino[4,5-b]quinoline-1-one;

7-chloro-4-hydroxy-2-(N-ethyl-4'-methoxyaniline)-5,10-dihydro-2H-pyridazino [4,5-b]quinoline-1-one;

7-chloro-4-hydroxy-2-(4'-fluorophenyl)-5,10-dihydro-2H-pyridazino[4,5-b]quinoline-1-one;

7-chloro-4-hydroxy-2-(4'-methoxy-3-pyridyl)-5,10-dihydro-2H-pyridazino[4,5-b]quinoline-1-one;

7-chloro-4-hydroxy-2-(3',4'-dimethoxyphenyl)-5,10-dihydro-2H-pyridazino [4,5-b]quinoline-1-one;

7-chloro-4-hydroxy-2-(2',4'-dimethylphenyl)-5,10-dihydro-2H-pyridazino[4,5-b]quinoline-1-one;

7-chloro-4-hydroxy-2-(3'-methoxyphenyl)-5,10-dihydro-2H-pyridazino [4,5-b]quinoline-1-one;

7-chloro-4-hydroxy-2-(4'-bromo-2'-methoxyphenyl)-5,10-dihydro-2H-pyridazino[4,5-b]quinoline-1-one;

7-chloro-4-hydroxy-2-(ethylthioethyl)-5,10-dihydro-2H-pyridazino[4,5-b]quinoline-1-one;

7-chloro-4-hydroxy-2-(2',5'-dimethylphenyl)-5,10-dihydro-2H-pyridazino[4,5-b]quinoline-1-one;

7,9-dichloro-4-hydroxy-2-(4'-methoxyphenyl)-5,10-dihydro-2H-pyridazino[4,5-b]quinoline-1-one;

7-chloro-4-hydroxy-2-(4'-methylbenzyl)-5,10-dihydro-2H-pyridazino[4,5-b]quinoline-1-one;

7,9-dichloro-4-hydroxy-2-(2',4'-dimethylphenyl)-5,10-dihydro-2H-pyridazino[4,5-b]quinoline-1-one;

7-chloro-4-hydroxy-2-(4'-bromo-2'-methylphenyl)-5,10-dihydro-2H-pyridazino[4,5-b]quinoline-1-one;

7-chloro-4-hydroxy-2-(2'-fluorobenzyl)-5,10-dihydro-2H-pyridazino[4,5-b]quinoline-1-one;

7-chloro-4-hydroxy-2-(3'-chlorobenzyl)-5,10-dihydro-2H-pyridazino[4-5-b]quinoline-1-one;

7-chloro-4-hydroxy-2-(2'-cyanobenzyl)-5,10-dihydro-2H-pyridazino[4,5-b]quinoline-1-one;

7-chloro-4-hydroxy-2-(3'-methylphenyl)-5,10-dihydro-2H-pyridazino[4,5-b]quinoline-1-one and 7-chloro-4-hydroxy-2-(3'-phenoxyphenyl)-5,10-dihydro-2H-pyridazino[4,5-b]quinoline-1-one.

Pyridazinediones of formula A or B (or other formulae as recited herein) can be made by processes which include processes known in the chemical arts for the production of structurally analogous compounds. The preparation of compounds wherein Z is H on certain starting materials described herein can be effected by chlorinating the hydroxy group of the dialkyl-4-OH-quinoline-2,3-dicarboxylate (starting material) using phosphorous oxychloride. This chlorine is then reduced using tetrakistriphenylphosphine Pd(O) and sodium formate to provide dimethyl quinoline-2,3-dicarboxylate which is then processed through the remaining chemical steps (e.g. adding the hydrazine etc.) The processes for the manufacture of a starting pyridazinedione of formula I as defined above are provided to show the preparation of the preferred starting materials utilized in the present invention and are illustrated by the following procedures in which the meanings of generic radicals are as given above unless otherwise qualified. Such a process can be effected, generally:

(a) to obtain a compound of formula I, by treating a corresponding diester of formula IV, wherein $R^{13}$ is $(C_1-C_3)$alkyl, with an aryl or heteroaryl substituted hydrazine wherein aryl is selected from phenyl or a benz derivative thereof (e.g. napthyl) and is either unsubstituted or substituted with 1, 2 or 3 groups chosen from —O-$(C_1-C_4)$alkyl, —OH, -halo, —NO$_2$, —CN, —CF$_3$, —NH(CO)R', —$(C_1-C_4)$alkyl, —NR'R", —CO$_2$R', —CONR'R", —SO$_m$R', —SO$_2$NR'R", $(C_1-C_6)$alkyloxy$(C_1-C_6)$alkyloxy-, hydroxy$(C_1-C_6)$alkyloxy-, $(C_1-C_6)$alkyloxy$(C_1-C_6)$alkyloxy$(C_1-C_6)$alkyloxy-, hydroxy$(C_1-C_6)$alkyloxy$(C_1-C_6)$alkyloxy-, —O$(C_1-C_6)$alkylNR'R", —NR'$(C_1-C_6)$alkylNR'R", —$(C_1-C_6)$alkylNR'R", —OCF$_3$, —NR'$(C_1-C_6)$alkyloxy, —NR'$(C_1-C_6)$alkylhydroxy; and heteroaryl is selected from unsubstituted or substituted aromatic species and benz derivatives thereof including pyridyl, thienyl, furanyl, or those groups containing two heteroatoms selected from N, O or S such as pyrazole, imidazole, isoxazole, oxazole, thiazole, isothiazole, or those groups containing three heteroatoms chosen from N, O or S such as triazole, oxadiazole wherein the N on the heteroaryl group is optionally substituted with R and the substituted aromatic substituents include typical aromatic substituents selected from hydroxy, alkoxy, halo or cyano and the heteroaryl group is attached to —(CH$_2$)$_n$ via a carbon atom on the heteroaryl group; which forms a compound of formula V (a pyrrolo[3,4-b]quinoline) by refluxing the above reactants in (1) ethanol or other suitable solvent for a 12 hour period followed by reflux in acetic acid (AcOH). The compound of formula V is then treated with methanesulfonic acid (MeSO$_3$H) in refluxing methanol or other suitable solvent for an eighteen hour period to form a compound of formula I wherein $R^1$ or $R^2$ is aryl as defined above (Scheme 1);

(b) to obtain a compound of formula I, by treating a corresponding diester of formula IV, wherein $R^{13}$ is $(C_1-C_3)$ alkyl, with a $(C_1-C_6)$alkylaryl or $(C_1-C_6)$ alkylheteroaryl substituted hydrazine wherein aryl and heteroaryl are as defined above in (a) in (1) refluxing ethanol and (2) refluxing acetic acid to form a compound of formula I wherein $R^1$ or $R^2$ is selected from $(C_1-C_6)$alkylaryl wherein aryl and heteroaryl are defined as above. The positional isomers obtained in this process may readily be separated by fractional acidification of meglumine/choline solutions (Scheme 2);

(c) to obtain a compound of formula I, by treating a compound of formula IV, wherein $R^{13}$ is $(C_1-C_3)$alkyl, with a $(C_1-C_6)$alkyl substituted hydrazine wherein the alkyl group is optionally further substituted with substituents selected from OH, OR', SR', or NR'R" in refluxing ethanol followed by treatment in refluxing acetic acid to form a compound of formula VI or VI' wherein $R^1$ or $R^2$ is a substituted alkyl species as described above. The resulting compounds (when Y is OH, SH or NHR) can then be further derivatized to form compounds wherein W is NR'COR", NR'CO$_2$R", NRCONR'R", CO$_2$R', or CONRR' or as further defined herein (Scheme 3). The isomeric mixture is treated with aqueous meglumine or aqueous meglumine/choline mixture to form a solution which is further acidified with acetic acid to pH 6–7. The solid precipitate is then filtered off to separate the 3-positional isomer while the filtrate is then further treated with acetic acid to a pH of around 5.5 to form a solid which is the 2-positional isomer (VI').

(d) to obtain a compound of formula I as recited in (c) above wherein the substituted alkyl group contains a heterocyclic species, by (1) treating a corresponding compound of formula VI or VI' wherein W is (—OH) with a hydrohalogenic acid (HBr) to form the corresponding halogenated species and (2) treating this compound with a nucleophilic species to form a compound of formula I wherein $R^1$ or $R^2$ is —(CH$_2$)$_n$heterocycle wherein heterocycle comprises a five- and/or six- and/or seven-membered heterocyclic ring containing 1, 2 or 3 heteroatoms chosen from O, N, or S wherein an N on the heterocycle is optionally substituted with R' and a carbon or nitrogen atom on the heterocycle may be substituted with R or R' or to form a compound of formula I with $R^1$ as —(CH$_2$)$_n$Nu wherein Nu is also equal to ArNH—, R'NH—, ArO—, ArS—, or other common nucleophiles which can react with an alkylbromide (Scheme 4). The halogenated intermediate described herein is also used to prepare carboxylic acid and/or ester derivatives thereof by reacting the bromo compound with sodium cyanide and then hydrolyzing and or esterifying the resultant cyano compound.

(e) to obtain a compound of formula I via a process as described herein is achieved according to the general procedure described in Scheme 5 and specifically exemplified in Examples within 35–81. A 3-carboalkoxy-4-hydroxyquinoline-2-carboxylic acid (prepared from the corresponding dialkylester (IV')) is reacted with thionyl chloride to form the corresponding 3-carboalkoxy-2-acid chloride which is reacted with either an arylhydrazine wherein aryl is as defined above (under the appropriate conditions as shown in the examples) or a heteroarylhydrazine wherein heteroaryl is as defined above (under the appropriate conditions as shown in the examples). The solvents used in the formation of the hydrazide include any anhydrous organic solvent selected from, for example THF, toluene, CH$_2$Cl$_2$, CH$_3$Cl, hexane or any inert organic solvent. The present invention relates to a novel process for producing the 2-substituted pyridazino quinolines of formula I (or II) wherein $R^1$ is aryl or heteroaryl comprising the steps of (i) forming the 3-carboalkoxy-2-acid halide intermediate from the corresponding dialkyl ester of formula IV' and (ii) reacting said halide from step (i) with either an arylhydrazine wherein aryl is as defined above under the conditions described in the examples or an heteroarylhydrazine wherein heteroaryl is as defined above under the conditions described in the examples to form a compound of formula II wherein $R^1$ is aryl or heteroaryl. Variable amounts of the 3-isomer is also produced in this process. The above process optionally goes through a novel key intermediate selected from a 3-carboalkoxy-4-hydroxy quinoline-2-carboxylic acid N-2-aryl (or heteroaryl)hydrazide. The cyclization reaction from the acyl hydrazide to the PQD tricyclic ring structure is optimally performed in methanesulfonic acid and methanol. However, lower molecular weight (C$_1$–C$_4$) alkyl sulfonic acids and lower molecular weight alcohols (C$_2$–C$_6$)alkyl) may also be used with optional cosolvents selected from, but not limited to, THF or dioxane or equivalent solvents which solubilize the reactants. In addition, under some circumstances, (e.g. with electron rich substituents on the aromatic ring) alternative acids, e.g. dilute HCl in H$_2$O, may also be utilized to achieve cyclization. Furthermore, other organic solvents such as ether, dioxane, CH$_2$Cl$_2$, CH$_3$CN, DMF or equivalent solvent, may also be utilized to achieve coupling and cyclization. This intermediate is preferably used in the production of compounds of formula II wherein $R^1$ is aryl. The hydrazide may, depending upon the aryl or heteroaryl substituents, proceed directly to the 2-substituted PQD or via the 5-membered pyrrole intermediate which then forms both the 2 and 3 substituted PQD. Electron donating groups on the aryl ring promote selective formation of the 2-substituted PQD. Steric effects may also influence the degree of selectivity.

(f) to obtain a compound of formula I via a process as described herein is achieved according to the general procedure described in Scheme 6 and specifically exemplified in non-limiting examples 42a, 43a and in examples 82–103 and examples 138–142. A 2-pyrrolidinocarbamide-quinoline-3-carboxylic acid, prepared from hydrolysis of the corresponding 3-methyl ester which is prepared by reacting the corresponding 3-carbomethoxy-quinoline-2-carboxylic acid with dicyclohexylcarbodiimide or other appropriate diimide coupling reagent such as diisopropyl carbodiimide and pyrrolidine, is reacted with an N-t-butoxycarbonyl-N'-2(CH$_2$)$_n$M (n=0–4) hydrazine (prepared from the reaction of either (a) t-butylcarbazate and the desired (C$_1$–C$_4$)alkylaryl or a substituted alkyl aryl or an alkoxy alkyl compound wherein the terminal alkyl carbon has a suitable leaving group selected from halo (X) or triflate in a solvent such as DMF, CH$_2$Cl$_2$ or CH$_3$CN or equivalent and a base such as NEt$_3$ or, for n=0 (e.g. direct n-aryl substitution), other groups which may readily react with t-butylcarbazate to form a starting disubstituted hydrazine t-butylO(CO)-N-N-$R^1$ include any alkylaryl, aryloxyalkyl, alkyloxyalkyl, alkyloxyalkyloxy or alkylheteroaryl recited herein wherein the alkyl group has a suitable leaving group (b) a suitable aryl- or substituted arylhydrazine with di-t-butyl-dicarbonate in an organic solvent (e.g. THF or equivalent) or (c) (for n=1–4) a suitable aryl or substituted aryl aldehyde or substitutes alkylaldehyde with t-butylcarbazate in refluxing hexanes or equivalent organic solvent to form the corresponding imine which is then reduced with a reducing agent (e.g. BH$_3$ THF or LiAlH$_4$) to obtain a key intermediate hydrazide which is cyclized in CH$_3$SO$_3$H/THF or equivalent solvent to selectively form a 2-substituted aryl or alkylaryl PQD or substituted alkyl PQD. This process may generally be utilized to selectively form a compound of formula II. t-Butylcarbazate is commercially available and the $R^1$-substituted t-butyl carbonate hydrazines are readily prepared.

(g) N-2 aryl and heteroaryl substituted isomers may readily and selectively be prepared as shown in Scheme 7 by treating an aryl or heteroarylhydrazine with benzaldehyde followed by a reduction of the hydrazide imine to form an N-aryl-N-benzyl substituted hydrazine. This compound is then reacted with a 3-carboxyester-2-acid halide quinoline to form a hydrazide intermediate, e.g. 3-carboalkoxy-4-hydroxyquinoline-2-carboxylic acid N-2-aryl(or heteroaryl)-N-1-benzyl-hydrazide which is treated sequentially with choline hydroxide or heat (80–180° C.) and methanesulfonic acid or equivalent acid with or without a suitable solvent to selectively form an N-2-aryl PQD.

It is noted that, in general, when unsymmetrical hydrazines are employed, for example where $R^1$ and $R^2$ are different groups or where a monosubstituted hydrazine is employed, a mixture of products (2-substituted versus 3-substituted) will be obtained unless the novel processes recited herein are utilized. Such mixtures are separable by standard (for example chromatographic or recrystallization) techniques known to the art and used for the purpose. A compound of formula I wherein L is a heterocyclic moiety such as a 4-($C_1$–$C_6$)substituted piperazine or 4-arylsubstituted piperazine or a phthalimido or another commercially available nucleophilic heterocycle may be formed by reacting the heterocyclic nucleophilic species with a 2- or 3-halo($C_1$–$C_6$)alkylpyridazino[4,5-b]quinolines of formula I, the latter of which is prepared from the corresponding hydroxy species as described in (d) above. As the following examples will show, compounds within the scope of the present invention are prepared by a variety of chemical synthetic steps or procedures. Analogous processes to produce a compound of formula I wherein $R^1$ and $R^2$ equal hydrogen can be utilized to make the immediate precursor to a compound of formula A or formula B except an unsubstituted hydrazine is utilized in the coupling reaction with a corresponding diester of formula IV, (see steps (a) or (b) for analogous process). These processes are also described in EP Application 0 516 297A1. Each of the processes described above describes the preparation of the final intermediate which is reduced under the appropriate conditions to form a compound of formula A, B or C which are potent glycine receptor antagonists. Of course, as the formula pages relating to the preparation of A, A', B, B' and C and C' show, intermediates D, E, F, G, H, I, J, K, L, M, N, O, P and D'–P' are prepared via the analogous processes described in steps (a)–(g). In certain circumstances, it may be necessary to protect a reactive carbonyl before reducing the B ring to the enamine or amine. For example, Formulae shown generally as Q, Q', R, R', S or S' show various acylated intermediates or glycine receptor antagonists which are prepared from the corresponding non-acylated species. Alternatively, acylation of a compound of formula I or II, including those species wherein $R^1$ and $R^2$ equal H, may be achieved before reduction of the B-ring carbonyl or enamine under the general conditions specified herein. In that instance, a compound of formula Q-S' is formed wherein the compounds are useful as intermediates whether or not they are also active as glycine receptor antagonists. As shown in formula A or A', the single dashed line indicates a double bond may be present depending upon the valency or groups attached to the C-1 or C-4 position of the PQD ring structure. Formulae shown as Q, Q', R, R', S and S' indicate the possible formulae which form the basis for A or A' as indicated. For example, Q or Q' show an N3 $R^2$ substituted moiety with a carbonyl at C-4 and an $OR^3$ group off C-1 with a double bond between C-1 and N2. The other possible formulae are shown as R-S'. The curvy line on formula A, A' etc., indicates a group is optionally present. Additionally, an intermediate such as K' may be prepared from the corresponding enamineone precursor. Compounds of formula A or A' wherein $R^5$ is ($C_1$–$C_6$)alkyl or ($C_1$–$C_6$)alkylaryl may be prepared from the corresponding compound of formula I or II by alkyl or alkylaryl addition to the B-ring carbonyl of the PQD systems.

Compounds of formula T may also be formed during the reduction processes described herein (e.g. from a compound of formula II) and are also part of the claimed invention. A compound of formula T wherein the B ring double bond is present and the B-ring carbonyl is present may be prepared by acylating a compound of formula II to form T' with an acylating agent X(CO)$R^6$. A compound of formula T' is useful as an intermediate to produce compounds of formula A or A' and is useful as a glycine receptor antagonist and is claimed herein. A compound of formula T may also be formed by reducing a compound of formula IV so that the ketone remains intact and the double bond of the enamine is reduced. This product may be formed in a reduction of IV which may be carried forward via coupling and cyclization to a PQD of formula T. In general, Scheme 8 describes how some of the compounds within the scope of the present invention are prepared. The preferred compounds are those of formula B. The preferred process for producing compounds of formula B involves (i) preparing a starting PQD of formula II and reducing this compound under the appropriate conditions to a compound of formula B. The preferred conditions involve suspending a compounding of formula II (specifically prepared as shown in examples 1–144) in an organic solvent selected from, but not limited to, THF with subsequent addition of trifluoroacetic acid (significant molar excess). This suspension is cooled to about 0° C. and sodium borohydride is added in molar excess (5×). The reduction is then allowed to proceed at 0° C. for about 15 minutes and then warmed to room temperature and stirred for about 3 hours. Upon work-up and after triturating and filtering (2×), the title compounds are readily obtained. The preferred group for Z on a compound of formula II is oxygen. Z, in a compound of formula I', may also be hydrogen, OH SH or NHR. Key intermediates are shown in the Schemes or described in the text. Examples 1–34 proceed generally from formula IV' and produce, in a non-selective manner, via the intermediate V' (except for those examples which displace or react with an N-2 hydroxy alkyl compound) the desired or preferred N-2 aryl or substituted aryl starting materials (e.g. $R^1$=aryl or subsituted-aryl and n=0). N-2 benzyl or phenethyl compounds and substituted versions thereof are also produced via this process. The isomers produced in this process are readily separable. Other intermediates in the early examples include the N-2 hydroxy alkyl PQD which is further reacted with lower alkyl ($C_1$–$C_4$)acids to form the corresponding ester. The carbon chain bonded to the N-2 nitrogen may vary from 1–6 carbon atoms with the hydroxy group on the terminal position. N-2 aryl derivatives are also prepared in examples 35 etc. wherein a key intermediate is the quinoline 2-acid chloride which is reacted with an arylhydrazine to form, in some cases selectively, the N-2 aryl PQD. Of course N-methyl-glucamine or other salts (e.g. choline, sodium etc.) are readily prepared from the corresponding non-salt form of formula B. The intermediate generated from the acid chloride is the 3-carboalkoxy-4-hydroxyquinoline-2-carboxylic acid N-2 aryl (or substituted-aryl) hydrazide which, under favorable conditions, forms the N-2 aryl substituted PQD starting materials. Of course, if the reduction is performed before coupling and cyclization, the key intermediate is the 3-carboalkoxyquinoline-2-carboxylic acid N-2 substituted hydrazide. Improved conditions using 1 equivalent of the starting arylhydrazine are described in the examples. In general methanesulfonic acid in methanol or THF has been utilized to cyclize the intermediate hydrazide. Of course, any methoxyphenyl species may be hydrolyzed with HBr or other acid (e.g. $CH_3SO_3H$) to form the corresponding hydroxy species.

The N-2 hydroxy alkyl PQD compounds are utilized to form the corresponding N-2 haloalkyl PQD derivatives which are used as intermediates to form, for example, the N-2 alkyl($C_1$–$C_4$)thioalkyl($C_1$–$C_4$) compounds. The appropriate thiolate anion in DMF is reacted with an N-2 haloalkyl PQD. Of course, amines, anilines or other heterocyclic or heteroaryl nucleophiles may react with the N-2-alkyl ($C_1$–$C_4$)halo PQD to form the corresponding nucleophilic substituted PQD. DMF or equivalent organic solvent is utilized in this process.

As exemplified in a non-limiting manner in Example 82, a key process for selectively producing N-2 aryl, heteroaryl, substituted alkyl or other species prepared from any N-2 intermediates involves the initial production of a 2-pyrrolidinoamido substituted quinoline which is formed from the corresponding 2-carboxy-3-carboalkoxy quinoline. This compound or analogous compounds (e.g. with groups equivalent to pyrrolidinoamido) is hydrolyzed to form the corresponding 2-pyrrolidinoamido-3-carboxy quinoline which is then coupled with the selected $R^1$—N—N—C(O) O-t-butylhydrazine using a selected diimide (e.g. DCC or equivalent) to form a hydrazide intermediate—e.g. 2-pyrrolidinoamido-3-carboxylic acid-$NR^1$—N(BOC) hydrazide which, under the cyclization conditions, forms the N-2 substituted PQD without any N-3 substituted PQD formed. While this process is primarily utilized to form the immediate precursors to the reduced PQDs (e.g. compounds of the invention), it may also be utilized using or via intermediates G, G', H, H', P or P'. The hydrazines utilized in this process are readily prepared from commercially available materials as described herein wherein either t-butylcarbazate or di-t-butyldicarbonate are utilized to BOC one N of the hydrazine depending upon whether $R^1$ is aryl or alkylaryl or alkyl or substituted alkyl or heteroaryl or alkyl heteroaryl. For example, the benzyl or substituted benzyl compounds described herein are readily and conveniently prepared from the appropriate 2-pyrrolidinoamido-3-carboxylic acid and the N-benzyl-N1-t-butyl carboxyhydrazine which was actually prepared from the corresponding aryl alkylhalide and t-butyl carbazate. t-Butylcarbazate reacts readily to displace the halide or alcohol such as triflate to form the desired hydrazine.

Another intermediate and glycine receptor antagonist includes N-2-aryl PQDs of formula B substituted with a cyano substitutent or substituents. This moiety (CN) can be further manipulated to form carboxylic acids, carbonyl halides, esters, amides, or tetrazoles. As indicated previously, anion displacement (nucleophilic displacement) is utilized to produce various heterocyclic compounds or benz or heteroaryl benz derivatives thereof which are glycine receptor antagonists. An N-2 halo($C_1$–$C_4$)alkyl PQD is reacted with the selected nucleophile (heterocyclic or heteroaryl wherein heteroaryl includes for example, those compounds shown in the examples and described herein) to form the corresponding N-2 Nucleophile-($C_1$–$C_4$)alkyl PQD.

Certain N-2 heterocyclic PQDs can be further hydrolyzed to form amido alcohols within the scope of the present invention. For example, oxizolidine diones are readily hydrolyzed to the corresponding amide alcohols as shown in Example 112 and Table 5. The Formulae pages show some of the key intermediates recited herein. Key intermediates include compounds of formula XIV–XX. As described previously, the present invention relates to a process for producing a compound of formula B comprising the steps as recited therein.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

Certain diesters of formula IV for use in reacting with substituted hydrazine to make a compound of formula I, can be made by treating a compound of formula VII with a suitable base, such as an alkali metal alkoxide (e.g., potassium t-butoxide) in a suitable solvent such as t-butanol to effect ring closure and thereby yield the desired diester. In said compound of formula VII, the value of Y corresponds to the following to yield a corresponding value for Z as noted:

a. CHO if a value for Z of hydrogen is desired;
b. $COOR^{15}$ wherein $R^{15}$ is ($C_1$–$C_3$)alkyl if a value for Z of hydroxy (or the tautomerically equivalent oxo) is desired; (It is noted that higher alkyl esters can be employed, but they do not provide any synthetic advantage.)
c. $CSOR^{15}$ or $CSSR^{15}$ if a value for Z of thiohydroxy (SH) is desired; and
d. CN if a value for Z of amino is desired. The compound of formula VII need not be isolated to make the corresponding compound of formula IV'. Rather, the diester of formula IV can be made in a one-pot process without separating the compound of formula VII from the reaction mixture.

A diester of formula IV' wherein Z is hydroxy (or oxo) can also be made by treating an isatoic anhydride of formula X directly with a sodium or potassium salt of a ($C_1$–$C_3$)dialkyl (e.g. diethyl) ester of 2-oxosuccinic acid in a suitable solvent such as dimethylformamide.

A diester of formula IV' wherein Z is thiohydroxy can be made by treating a corresponding diester of formula IV wherein $R^3$ is hydroxy with Lawesson's reagent, 2,4-bis(4-methoxyphenyl)-1,3-dithia-2,4-diphosphetane-2,4-disulfide, in a suitable solvent such as toluene or dimethoxyethane and at a temperature in the range of 50–110° C.

A substituted imide of formula V' wherein the B-ring N loses its H and Z is, for example, $NH_2$ can be made by treating a diester of formula IV', wherein the value corresponding to Z is a halo group such as chloro or bromo, with ammonia which forms the corresponding phthalimide which is then further reacted with arylhydrazine to form V' which is then reacted in typical fashion (Scheme 1) to form the final pyridazinoquinoline.

A compound of formula VII, wherein Y is CN, CHO, $COOR^{15}$, $CSOR^{15}$, or $CSSR^{15}$ wherein $R^{15}$ is a ($C_1$–$C_{10}$) alkyl, or a ($C_2$–$C_{10}$)alkenyl or alkynyl group can be made by treating a corresponding ortho amine of formula VIII with a dialkyl acetylenedicarboxylate, such as dimethyl acetylenedicarboxylate, in a suitable solvent such as a ($C_1$–$C_4$)alcohol. As solvent, t-butanol is preferred.

An ortho amine of formula VIII' can be made by esterifying a corresponding acid of formula VIII' by conventional methods. An acid of formula VIII' can in turn be made by deprotecting a corresponding compound of formula VIII" wherein the amino group has been protected with a conventional protecting group Pr (such as tert-butoxycarbonyl, t-BOC). A compound of formula VIII" can in turn be made by sequentially reacting an amine of formula IX first with two equivalents of an organolithium compound (for example t-butyllithium) to form a dilithiated species which can be carboxylated by reacting with carbon dioxide. An amine of formula IX can be prepared by protecting a corresponding (unprotected) amine by conventional methods.

An ortho amine of formula VIII, wherein Y is COOR$^{15}$, can also be made by a process which differs from that described immediately above in that the esterification step is effected by using a base (for example, sodium hydride) followed by an alkylating agent R$^{15}$X on the protected acid of formula VIII" rather than on the acid of formula VIII'.

An ortho amine of formula VIII', wherein Y is COOR$^{15}$, can also be made by treating a corresponding isatoic anhydride of formula X with base (such as an alkali metal hydroxide) in alcoholic solvent of formula R$^{15}$OH.

An isatoic anhydride of formula X can be made by treating an isatin of formula XI with chromium trioxide in the presence of acetic anhydride, or with a peroxycarboxylic acid such as the magnesium salt of monoperoxyphthalic acid, and in a suitable solvent such as acetic acid.

An isatin of formula XI can be made by cyclizing a hydroxyimino acetamide of formula XII in concentrated sulfuric acid at a temperature of 60–80° C.

A hydroxyimino acetamide of formula XII can be made by treating an amine of formula XIII with chloral hydrate in the presence of sodium sulfate and hydroxylamine hydrochloride and in a suitable solvent such as water.

The N-t-butoxy-carbonylhydrazines utilized in the present invention may be prepared according to the procedure set forth in example 82c. For example, N-t-butoxy-carbonyl-N'-pentafluorobenzylhydrazine; N-t-butoxy-carbonyl-N'-2-cyanobenzylhydrazine; N-t-butoxy-carbonyl-N'-3-chlorobenzylhydrazine; N-t-butoxy-carbonyl-N'-3,5-ditrifluoromethyl benzylhydrazine; N-t-butoxy-carbonyl-N'-3-phenylpropylhydrazine; N-t-butoxycarbonyl-N'-4-methylbenzylhydrazine; N-t-butoxy-carbonyl-N'-4-trifluoromethylbenzylhydrazine; N-t-butoxy-carbonyl-N'-4-cyanobenzylhydrazine; and N-t-butoxy-carbonyl-N'-2 4-dimethylphenylhydrazine.

The present invention, therefore, also relates to these novel hydrazine moieties and to processes for their production and use as intermediates to couple with the key intermediate 2-pyrrolidinocarbamide quinoline 3-carboxylic acid to form a compound of formula B via a novel and inventive process as described herein which selectively forms the N-2-substituted PQD. The intermediate hydrazines utilized to prepare N-2-aryl or N-2-substituted aryl PQDs may also be prepared according to the non-limiting example 42a. N'-t-butoxy-carbonyl-N'-aryl or substituted aryl compounds are produced via this novel process to enable selective formation of the N-2-substituted PQDs. This process may be the referred route to aryl substituted compounds claimed and recited herein. Intermediates or compounds shown as D–P or D'–P' are part of the present invention. Process steps recited as (j)–(r) describe alternative methods which may be utilized to prepare the compounds claimed wherein. As indicated previously, the preferred route involves preparing a starting material as described in process steps (a)–(i) and then reducing this compound of formula II to a compound of formula B.

It is noted that many of the starting materials for synthetic methods as described above are commercially available and/or widely reported in the scientific literature.

Examples of suitable pharmaceutically acceptable salts are salts formed with bases which form a physiologically acceptable cation, such as alkali metal (especially lithium, sodium and potassium), alkaline earth metal (especially calcium and magnesium), aluminum and ammonium salts, as well as salts made with appropriate organic bases such as choline hydroxide, triethylamine, morpholine, piperidine, ethylenediamine, lysine, ethanolamine, diethanolamine, triethanolamine, N-methyl-D-glucamine (meglumine), arginine, and tris(hydroxymethyl)aminomethane. Choline, meglumine, sodium and potassium salts are preferred. Choline, sodium and potassium salts are especially preferred.

When used to intervene therapeutically following a stroke, a pyridazinedione of formula B generally is administered as an appropriate pharmaceutical composition which comprises a compound according to the invention as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; and in the form of powders together with pharmaceutically acceptable inert solid diluents such as lactose for administration by insufflation.

The dose of a compound according to the invention which is administered will necessarily be varied according to principles well known in the art taking account of the route of administration, the severity of the postischemic disorder, and the size and age of the patient. In general, a compound of according to the invention will be administered to a warm blooded animal (such as man) so that an effective dose is received, generally a dose in the range of about 0.01 to about 100 mg/kg body weight. For example, if the compound is administered intravenously, it is administered in the range of about 0.01 to about 10 mg/kg body weight. If it is administered orally, it is administered in the range of about 0.5 to about 100 mg/kg body weight.

It will be apparent to those skilled in the art that a compound according to the invention can be co-administered with other therapeutic or prophylactic agents and/or medicaments that are not medically incompatible therewith. In general, representative compounds of the instant invention do not show any indication of overt toxicity in laboratory test animals.

The actions of compounds according to the invention as antagonists at the glycine receptor of the NMDA receptor complex can be shown by one or more standard tests such as the [3H]-glycine binding assay (Test A) and by tests in vivo such as the red nucleus test (Test B) and the Rat Middle Cerebral Artery test (Test C). These tests confirm that compounds of the invention are NMDA receptor antagonists in vitro and in vivo. Certain compounds of the invention are highly potent NMDA receptor antagonists. In particular, the compounds of the present invention of formula A with R$^1$ as an alkyl, aryl or heterocycle or heteroaryl as defined herein and R$^2$ as H are highly potent NMDA receptor (Glycine) antagonists.

Test A

In the [3H]-glycine binding assay, neuronal synaptic membranes are prepared from adult (about 250 g) male Sprague-Dawley rats. Freshly dissected cortices and hippocampi are homogenized in 0.32 M sucrose (110 mg/mL). Synaptosomes are isolated by centrifugation (1000×g, 10 min), the supernatant is pelleted (20,000×g, 20 min) and resuspended in double-distilled water. The suspension was centrifuged for 20 minutes at 8,000×g. The resulting supernatant and buffy coat are washed twice (48,000×g, 10 mins, resuspension in double-deionized water). The final pellet is quickly frozen (dry ice/ethanol bath) under double-deionized water and stored at −70° C.

On the day of the experiment, thawed synaptic membranes are homogenized with a Brinkmann POLYTRON (Brinkmann Instruments, Westbury, N.Y.) tissue homogenizer in 50 millimolar tris(hydroxymethyl)aminomethane citrate, pH 7.1. The membranes are incubated with 0.04% SUFACT-AMPS X100 (Pierce, Rockford, Ill.) in buffer for 20 minutes at 37° C. and washed six times by centrifugation (48,000×g, 10 min) and resuspended in buffer. The final pellet is homogenized at 200 mg wet weight/mL of the buffer for the binding assay.

For [3H]-glycine binding at the N-methyl-D-aspartate receptor, 20 nanomolar [3H]-glycine (40–60 Ci/mmol, New England Nuclear, Boston, Mass.) is incubated with the membranes suspended in 50 millimolar tris(hydroxymethyl)aminomethane citrate, pH 7.1 for 30 minutes at 4° C. Glycine, 1 millimolar, is used to define the nonspecific binding. Bound [3H]-glycine is isolated from free using a Brandel (Biomedical Research and Development Laboratories, Gaithersburg, Md.) cell harvester for vacuum filtration over glass fiber filters (Whatman GF/B from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. IC50 values are obtained from a least-squares regression of a logit-log transformation of the data. Typical IC50 values for compounds of the invention are usually less than 50 $\mu$M (micromolar) and are illustrated by the compound of Example 145 (IC50=0.045 $\mu$M), Example 147 (IC50=0.017 $\mu$M), and Example 148 (IC50=0.44 $\mu$M). The other designated examples disclosed herein are glycine antagonists within the scope of the present invention. Examples 1–144 are simply described as starting materials and do not fall within the scope of the present invention. The present invention, does however, include all the reduced species of examples 1–144 which may fall within formula A or A' or B or B', or T' and other intermediates as designated herein.

Test B

Red Nucleus Test The purpose of this test is to determine the effects of intravenously administered glycine antagonists on the NMDA-induced excitatory response of red nucleus cells. HA-966 (racemic) and CGP 37849 are reference agents that have been shown active in this test (ID50s of 7.9 and 1.7 mg/kg iv, respectively). The procedure for the red nucleus test is as follows. Rats are anesthetized with chloral hydrate (400 mg/kg ip) and the femoral vein is catheterized for iv drug administration. Five-barrel micropipettes are stereotaxically positioned in the red nucleus. Typically, three to four of the five barrels are filled as follows: the recording barrel with 2 M potassium citrate, the current balancing barrel with 4M NaCl, the drug barrel with 25 mM NMDA, and another drug barrel with 2.5 mM quisqualic acid (QA is only used in selectivity studies). NMDA is iontophoretically applied with an ejection current that is adjusted depending on the sensitivity of each individual red nucleus cell. The NMDA is cycled on and off (usually 30–60 sec. on and 60–120 sec. off) and the firing rate of the cell during each period is recorded. Once the baseline firing rate of the cell has been established, the test drug is administered iv. The effect of the drug on the NMDA-induced excitatory response of the red nucleus cell can be both qualitatively and quantitatively evaluated from the recordings and the raw data accumulated. Compounds of the invention exhibited a significant antagonist response. For example, the compound of example 145 as the meglumine salt (N=5) had an ID50 of 6.540.

Test C

Rat Middle Cerebral Artery Test Male SHR rats weighing 280–320 g are used for these studies. The method used for permanent middle cerebral artery (MCA) occlusion is as described by Brint et al (1988). Briefly, focal ischemia is produced by occluding first the left common carotid artery and then the left middle cerebral artery just superior to the rhinal fissure. Following occlusions, drugs are administered intravenously via jugular catheter. Twenty-four hours after MCA/common carotid artery occlusion, the animals are sacrificed and their brains quickly removed. Coronal sections of 1 mm thickness are cut using a vibratome and stained with 2,3,5, triphenyl-2H-tetrazolium chloride (TTC) dye. Following staining, necrotic tissue is readily distinguished from the intact brain and the area of infarcted cortex can be traced on an image analyzer. The infarct volume for each section is quantified with an image analyzer, and the total infarct volume is calculated with a program that summed all interval volume. See S. Brint et al. J. Cerebral Blood Flow 8:474–485 (1988). The statistical analysis of the difference between the volume of ischemic damage in the vehicle control and drug-treated animals is analyzed by student's-t-test. All data are presented as the mean +S.E. of the mean for n animals. compounds of the invention reduced ischemic damage. For example, the compound of example 145 at an I.V. dose of 10 mgs/kg/hr caused an infarct % volume change of −42% while a 5.0 mg/kg/hr I.V. dosage caused a −8% reduction.

The invention will now be illustrated by the following non-limiting examples. In the Examples, unless stated otherwise:

(i) temperatures are given in degrees Celsius (° C.); operations were carried out at room or ambient temperature, that is, at a temperature in the range of 18–25° C.;

(ii) evaporation of solvent was carried out using a rotary evaporator under reduced pressure (600–4000 Pascals; 4.5–30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by TLC or HPLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC or HPLC and had satisfactory nuclear magnetic resonance (NMR) spectra (300 MHz 1H NMR in D-DMSO unless otherwise specified) and microanalytical data;

(vii) yields are given for illustration only;

(viii) reduced pressures are given as absolute pressures in Pascals (Pa); other pressures are given as gauge pressures in bars; following abbreviations have also been used:

v (volume), w (weight); mp (melting point), L [liter(s)], mL (milliliters), mM (millimoles), g [gram(s)], mg [milligram(s)], min (minutes), h (hour); and (x) solvent ratios are given in volume: volume (v/v) terms.

Examples 1–144 are described to show how to prepare an immediate precursor utilized in the reduction of compounds of compounds of formula I, I", II or III to a compound of formula A, A', B, B', C or C'. Example 145 describes the experimental procedure utilized to reduce a compound of formula I to a compound of formula A (or II to B). Examples 146–177 are shown in Table 9 and these examples were prepared as described in Example 145.

As the examples and in vitro or in vivo results indicate, the present invention or the compounds and glycine receptor antagonists recited herein (e.g. A, A', B, B' . . . or T' or U) are useful as in vitro tools for determining relative glycine antagonist properties and as in vivo compounds or compositions which are useful as in vivo tools for determining relative antagonist properties and as compounds or compositions which antagonize the glycine receptor in animals or humans in need of treatment thereof. The present invention, therefore, also relates to a method of in vitro antagonism of a mammalian glycine receptor comprising administering an antagonist effective amount of a compound of formula A or A' or B or B' or T' wherein the respective variables ($R^1$–$R^6$) are as recited previously. The invention further relates to a method of in vivo antagonism of a mammalian, including human, glycine receptor comprising administering a pharmacologically effective amount of a compound of formula A or A', B or B' or T' to a mammal or a human wherein the variables for A, A', B, B' or T' are as previously defined.

EXAMPLES

Example 1
7-Chloro-1-hydroxy-3-(2-hydroxyethyl)-3,4,5,10-tetrahydropyridazino[4,5-b]quinoline-4,10-dione.

To a stirred mixture of dimethyl-7-chloro-4-hydroxy-quinoline-2,3-dicarboxylate (50.0 g, 0.169M, in ethanol (750 mL) was added 2-hydroxyethylhydrazine (286 g, 3.38M of 90% pure material). The resulting dark brown mixture was stirred at reflux for 18 hr and then allowed to cool to room temperature without stirring. The mixture was filtered, and the collected solids were washed once with ethanol and then refluxed for 3 hr in glacial acetic acid (1.0 L). The resulting mixture was allowed to cool to room temperature and then was filtered to separate a yellow solid. This material was dried overnight in vacuo to provide (41.83 g) a mixture of the isomeric 2- and 3-(2-hydroxyethyl) compounds as a yellow solid. This mixture was split into two fractions of 20.23 g and 21.6 g. The smaller fraction (20.23 g) was dissolved with vigorous stirring in water (2700 mL) containing N-methylglucamine (54.0 g). This solution was carefully acidified with glacial acetic acid until the pH just reached 7.0, and the precipitate which formed during the acidification was separated by filtration. The collected solids were washed once with water, dried, and saved. The filtrate and wash were also combined and saved. The larger (21.6 g) of the two original fractions was likewise dissolved in water (2880 mL) containing N-methylglucamine (57.6 g) and similarly acidified with glacial acetic acid to pH 7.0 to provide a second crop of solids. The filtrate and wash from this acidification were also combined and saved. The two crops of collected solids were combined to provide the title 3-(2-hydroxyethyl) compound as a bright yellow solid (19.27 g, 37.0%). Recrystallizaton of a portion of this material from acetic acid provided an analytical sample of the title compound as bright yellow crystals, mp 377–378° C.; MS(CI): 308 (M+H).

Analysis for C13H10ClN3O4: Calculated: C, 50.75; H, 3.28; N, 13.66; Found: C, 50.65; H, 3.39; N, 13.78; NMR: 13.19 (s, 1H, exchangeable), 12.32 (s, 1 H, exchangeable), 8.22 (d, J=9.0 Hz, 1H), 8.15 (d, J=1.8 Hz, 1H), 7.56 (dd, J=9.0, 1.8 Hz, 1H), 4.83 (br s, 1H, exchangeable), 4.10 (t, J=5.7 Hz, 2H), 3.75 (t, J=5.7 Hz, 2H).

The starting material, dimethyl-7-chloro-4-hydroxyquinoline-2,3-dicarboxylate, was prepared as follows:

a. Dimethyl-7-chloro-4-hydroxyquinoline-2,3-dicarboxylate.

A stirred mixture of methyl-2-amino-4-chlorobenzoate (2.50 g, 13.5 mM) and dimethyl acetylenedicarboxylate (2.05 g, 14.4 mM) in t-butanol (22 mL) was refluxed for 7 hours under a nitrogen atmosphere. After adding additional dimethyl acetylenedicarboxylate (1.16 g, 8.13 mM) and refluxing another 2.5 hours, the reaction mixture was allowed to cool to room temperature and potassium t-butoxide (1.56 g, 13.9 mM) was added in one portion. A precipitate formed and the resulting mixture was refluxed for 1.5 hours. The mixture was cooled to room temperature and filtered to separate the solids, which were washed with t-butanol and ether. The solids were dissolved in water and acidified with 1N sulfuric acid to form a precipitate. The resulting mixture was extracted with methylene chloride and the combined extracts were washed with brine and water, dried (MgSO$_4$), filtered and concentrated to give a green solid. Recrystallization of this material from methanol provided dimethyl-7-chloro-4-hydroxyquinoline-2,3-dicarboxylate (1.15 g, 28.94) as an off-white solid, mp 232–233° C.; MS (Cl):296 (M+H).

Analysis for C13H10ClNO5: Calculated: C, 52.81; H, 3.41; N, 4.74; Found: C, 52.75; H, 3.47; N, 4.69.

Example 2
7-Chloro-4-hydroxy-2-(2-hydroxyethyl)-1,2,5,10-tetrahydropyridazino[4,5-b]quinoline-1,10-dione.

All of the filtrates and washes saved from Example 1 were combined and further acidified with glacial acetic acid to pH 5.0. The precipitate which formed was collected, 30 washed with water, and dried to provide the title compound as a pale yellow solid (12.27 g, 23.5%). Recrystallization of a portion of this material from acetic acid provided an analytical sample of the title compound as an off-white crystalline solid, mp 335–336° C.; MS(CI): 308 (M+H).

Analysis for C13H10ClN3O4: Calculated: C, 50.75; H, 3.28; N, 13.66; Found: C, 50.54; H, 3.39; N, 13.65; NMR: 12.53 (br s, 1H, exchangeable), 11.87 (br s, 1H, exchangeable), 8.17 (d, J=8.7 Hz, 1H), 8.04 (s, 1H), 7.45 (d, J=8.7, 1H), 4.82 (br s, 1H, exchangeable), 3.99 (t, J=6.1 Hz, 2H), 3.70 (t, J=6.1 Hz, 2H).

Example 3
2-(2-Acetoxyethyl)-7-chloro-4-hydroxy-1,2,5,10-tetrahydropyridazino[4,5-b]quinoline-1,10-dione.

An orange suspension of 7-chloro-4-hydroxy-2-(2-hydroxyethyl)-1,2,5,10-tetrahydropyridazino[4,5-b]quinoline-1,10-dione (0.250 g, 0.81 mM) in a 30% solution of hydrobromic acid in glacial acetic acid (5 mL) was gently refluxed for 16 hours under nitrogen. The mixture was cooled to room temperature and diluted with water (20 mL) to form a precipitate. The collected solids were washed with water and methanol and then dried to give the title compound (0.242 g, 86%) as a tan solid, mp 307–309° C.; MS(CI): 350 (M+H).

Analysis for C15H12ClN3O5. 0.2 CH3CO2H: Calculated: C, 51.10; H, 3.57; N, 11.60; Found: C, 50.81; H, 3.45; N, 11.86; NMR: 12.64 (br s, 1H, exchangeable), 11.91 (br s, 1H, exchangeable), 8.14 (d, J=8.64 Hz, 1H), 8.02 (d, J=1.74 Hz, 1H), 7.43 (dd, J=1.74, 8.64 Hz), 4.32 (t, J=5.54 Hz, 2H), 4.13 (t, J=5.54 Hz), 1.98 (s, 3H).

Example 4
7-Chloro-4-hydroxy-2-(2-phthalimidoethyl)-1,2,5,10-tetrahydropyridazino[4,5-b]quinoline-1,10-dione.

2-(2-Bromoethyl)-7-chloro-4-hydroxy-1,2,5,10-tetrahydropyridazino[4,5-b]quinoline-1,10-dione (5.00 g, 13.50 mM) and potassium phthalimide (10.50 g, 56.70 mM) were stirred and refluxed in DMF (100 mL) for 22 hours. The cooled yellow suspension was poured into dilute hydrochloric acid (1N, 1.0 L) with good stirring. A white precipitate formed and was collected. This solid was resuspended in aqueous methanol (50%, 1.0 L) and stirred/sonicated to give a fine white suspension. Filtration and resuspension in methanol (0.25 L) gave a free-flowing white suspension after sonication and brief warming. The solids were finally collected and washed with methanol to give the title compound (4.65 g, 79%) as a white powder, mp 349–352° C.; MS(CI): 437 (M+H).

Analysis for $C_{21}H_{13}ClN_4O_5$. 0.35 $H_2O$. 0.10 $CH_3OH$: Calculated: C, 56.78; H, 3.18; N, 12.55; Found: C, 56.40; H, 2.76; N, 12.59; NMR: 12.54 (br s, 1H, exchangeable), 11.88 (br s, 1H, exchangeable), 8.11 (d, J=8.67 Hz, 1H), 8.00 (br s, 1H), 7.83 (s, 4H), 7.42 (d, J=8.67 Hz, 1H), 4.13 (br m, 2H), 3.93 (br m, 2H).

The starting material, 2(2-Bromoethyl)-7-chloro-4-hydroxy-1,2,5,10-tetrahydropyridazino[4,5-b]quinoline-1,10-dione, was prepared as follows:

a. 2(2-Bromoethyl)-7-chloro-4-hydroxy-1,2,5,10-tetrahydropyridazino[4,5-b]quinoline-1,1 0-dione.

7-Chloro-4-hydroxy-2-(2-hydroxyethyl)-1,2,5,10-tetrahydropyridazino[4,5-b]quinoline-1,10-dione (8.00 g, 26.00 mM) was stirred in a mixture of aqueous hydrobromic acid (50%, 80 mL), 30% hydrobromic acid in glacial acetic acid (160 mL) and methanesulfonic acid (8 mL) to give a red solution. This solution was refluxed for 20 hours during which time a precipitate formed. The yellow suspension was cooled to room temperature and stirred for 2 hours. The solids were collected and washed with acetonitrile/ether and ether and air dried to give the title bromoethyl compound (8.40 g, 88%) as an off-white powder, MS(CI): 370 (M+H). NMR: 13.00 (br s, 1H, exchangeable), 8.23–8.18 (m, 2H), 7.60 (dd, J=2.04, 5.73 Hz), 5.20 (t, J=9.37 Hz, 2H), 4.66 (t, J=9,37 Hz, 2H).

Example 5
7-Chloro-1-hydroxy-3-phenyl-3,4,5,10-tetrahydropyridazino[4,5-b]quinoline-4,10-dione, choline salt.

6-Chloro-2-anilino-2,3,4,9-tetrahydro-1H-pyrrolo[3,4-b]quinoline-1,3,9-trione (1.70 g, 5.00 mM) was stirred in methanol (0.85 L), and methanesulfonic acid (85 mL) was added. The yellow suspension was heated to reflux for 16 hours and cooled to room temperature. The resulting mixture was filtered (the filtrate was saved for use in Example 6), and the collected solids were washed with methanol and dried to give 7-chloro-4-hydroxy-3-phenyl-1,2,5,10-tetrahydropyridazino[4,5-b]quinoline-1,10-dione (0.48 g, 28%) as a yellow powder. This powder was stirred in methanol, and choline hydroxide (45 weight % in methanol, 0.5 mL) was added to give an amber solution. This solution was concentrated and the residue diluted with toluene and concentrated. The residue was diluted with toluene and concentrated two additional times, and the resulting solid residue was triturated with ethanol/toluene (20%, 25 mL) to provide a crystalline solid. The solid was collected to give the title compound (0.49 g, 78%) as a yellow powder, mp 253–257° C.; MS(CI): 340 (M+H).

Analysis for $C_{17}H_{10}ClN_3O_3$. $C_5H_{14}$ NO. 0.30 $H_2O$: Calculated: C, 58.90; H, 5.31; N, 12.50; Found: C, 58.88; H, 5.18; N, 12.41; NMR: 15.00 (s, 1H, exchangeable), 8.22 (d, J=8.79 Hz, 1H), 7.85 (d, J=2.01 Hz, 1H), 7.61 (d, J=7.53 Hz, 2H), 7.45 (t, J=7.53 Hz, 2H), 7.38–7.28 (m, 2H), 5.31 (s, 1H, exchangeable), 3.83 (br m, 2H), 3.39 (br m, 2H), 3.10 (s, 9H).

The starting material, 6-Chloro-2-anilino-2,3,4,9-tetrahydro-1H-pyrrolo[3,4-b]quinoline-1,3,9-trione, was prepared in the following manner:

a. 6-Chloro-2-anilino-2,3,4,9-tetrahydro-1H-pyrrolo[3,4-b]quinoline-1,3,9-trione.

To a stirred suspension of dimethyl-7-chloro-4-hydroxy-quinoline-2,3-dicarboxylate (2.50 g, 8.45 mM) in ethanol (35 mL) was added phenylhydrazine (5.82 mL, 59.20 mM) to give a brown solution. This solution was heated to reflux for 16 hours during which time a precipitate formed. The suspension was filtered hot, and the collected solids were washed with ethanol to give the phenylhydrazine salt of the title compound as a white powder (2.10 g). This material was stirred and refluxed in glacial acetic acid (50 mL) for 2 hours. The resulting yellow suspension was cooled to room temperature and filtered to give the title compound (1.70 g, 59%) as a yellow solid, mp 397° C.; MS(CI): 340 (M+H).

Analysis for $C_{17}H_{10}ClN_3O_3$: Calculated: C, 60.10; H, 2.97; N, 12.40; Found: C, 59.96; H, 2.79; N, 12.45; NMR: 13.80 (br s, 1H, exchangeable), 8.54 (s, 1H, exchangeable), 8.23 (d, J=8.70 Hz, 1H), 7.89 (d, J=1.89 Hz, 1H), 7.58 (dd, J=1.89, 8.70 Hz, 1H), 7.18 (t, J=8.01 Hz, 2H), 6.82 (m, 3H).

Example 6
7-Chloro-4-hydroxy-2-phenyl-1,2,5,10-tetrahydropyridazino[4,5-b]quinoline-1,10-dione.

The saved filtrate from Example 5 was diluted with water (0.80 L), and the resulting tan suspension was stirred for 1 hour. The solids were collected and washed with aqueous methanol (50%) to give the title compound (1.20 g, 71%) as an off-white powder, mp 347–349° C.; MS(CI): 340 (M+H).

Analysis for $C_{17}H_{10}ClN_3O_3$. 0.10 $H_2O$: Calculated: C, 59.80; H, 3.01; N, 12.30; Found: C, 59.64; H, 2.76; N, 12.27; NMR: 12.8 (br s, 1H, exchangeable), 12.1 (br s, 1H, exchangeable), 8.16 (d, J=8.67 Hz, 1H), 8.06 (d, J=1.80 Hz, 1H), 7.56–7.33 (m, 6H).

Example 7
7-Chloro-1-hydroxy-3-(4-methoxyphenyl)-3,4,5,10-tetrahydropyridazino[4,5-b]quinoline-4,10-dione.

6-Chloro-2-(4-methoxyanilino)-2,3,4,9-tetrahydro-1H-pyrrolo[3,4-b]quinoline-1,3,9-trione (2.72 g, 7.40 mM) was stirred in methanol (200 mL), and methanesulfonic acid (50 mL) was added. The tan suspension was heated to reflux for 16 hours during which it turned yellow. This yellow suspension was cooled to room temperature and filtered (the filtrate was saved for use in Example 8). The collected solids were washed with methanol to give the title compound as a yellow powder (1.19 g, 44%), mp 371–373° C.; MS(CI): 370 (M+H).

Analysis for $C_{18}H_{12}ClN_3O_4$: Calculated: C, 58.50; H, 3.27; N, 11.36; Found: C, 58.30; H, 3.41; N, 10.92; NMR: 13.33 (br s, 1H, exchangeable), 12.47 (s, 1H, exchangeable), 8.30 (d, J=8.73 Hz, 1H), 8.23 (br s, 1H), 7.61 (m, 3H), 7.08 (d, J=8.90 Hz, 2H), 3.83 (s, 3H).

The starting material, 6-Chloro-2-(4-methoxyanilino)-2,3,4,9- tetrahydro-1H-pyrrolo-[3,4-b]quinoline-1,3,9-trione, was prepared in the following manner:

a. 6-Chloro-2-(4-methoxyanilino)-2,3,4,9-tetrahydro-1H-pyrrolo[3,4-b]quinoline-1,3,9-trione.

To a stirred suspension of dimethyl-7-chloro-4-hydroxyquinoline-2,3-dicarboxylate (0.500 g, 1.69 mM) in ethanol (17 mL) was added 4-methoxyphenylhydrazine hydrochloride (2.07 g, 11.83 mM). Triethylamine (1.88 mL, 13.52 mM) was added, and the mixture was heated to reflux for 40 hours. The resulting suspension was filtered hot, and the collected solids were washed with ethanol to give the 4-methoxyphenylhydrazine salt of the title compound (0.700 g) as a light tan solid. This material was heated to reflux in glacial acetic acid (20 mL) for 2 hours to give a brown suspension. The suspension was cooled to room temperature. The solids were collected and washed with glacial acetic acid, methanol and ether to give the title compound (0.331 g, 53%) as a tan powder, mp 365° C. (decomp.); MS(CI): 370 (M+H).

Analysis for $C_{18}H_{12}ClN_3O_4$: Calculated: C, 58.50; H, 3.27; N, 11.36; Found: C, 58.29; H, 3.41; N, 11.14; NMR: 13.79 (br s, 1H, exchangeable), 8.22 (br d, J=8.70 Hz, 2H, 1H exchangeable), 7.88 (d, J=1.79 Hz, 1H), 7.57 (dd, J=1.79, 8.70 Hz, 1H), 6.78 (s, 4H), 3.67 (s, 3H).

Example 8

7-Chloro-4-hydroxy-2-(4-methoxyphenyl)-1,2,5,10-tetrahydropyridazino[4,5-b]quinoline-1,10-dione.

The saved filtrate from Example 7 was diluted with water (250 mL) to give a yellow suspension. The solids were collected and washed with aqueous methanol (50%) to give the title compound (1.22 g, 45%) as a dull yellow powder, mp 351–353 ° C.; MS(CI): 370 (M+H).

Analysis for $C_{18}H_{12}ClN_3O_4$: Calculated: C, 58.50; H, 3.27; N, 11.36; Found: C, 58.51; H, 3.44; N, 11.03; NMR: 12.74 (s, 1H, exchangeable), 12.01 (s, 1H, exchangeable), 8.15 (d, J=8.70 Hz, 1H), 8.05 (br s, 1H), 7.44 (multiplet, 3H), 7.02 (br d, J=6.96 Hz, 2H), 3.80 (s, 3H).

Example 9

7-Chloro-1-hydroxy-3-(4-hydroxyphenyl)-3,4,5,10-tetrahydropyridazino[4,5-b]quinoline-4,10-dione.

7-Chloro-1-hydroxy-3-(4-methoxyphenyl)-3,4,5,10-tetrahydropyridazino[4,5-b]quinoline-4,10-dione (0.800 g, 2.16 mM) was stirred in methanesulfonic acid (16 mL) to give an amber solution. This solution was heated to 160° C. for 6 hours and cooled to room temperature. Addition of ethyl ether (250 mL) gave a tan precipitate which was stirred for 1 hour. The solid was collected and washed with methanol/ether to give the title compound (0.661 g, 77%) as a tan powder, mp 393–395° C.; MS(CI): 356 (M+H).

Analysis for $C_{17}H_{10}ClN_3O_4$. $0.2CH_3SO_3H$. $1.3 H_2O$: Calculated: C, 51.86; H, 3.39; N, 10.55; Found: C, 51.76; H, 3.02; N, 10.37; NMR: 13.30 (s, 1H, exchangeable), 12.5 (v br s, 1H, exchangeable), 10.8 (br s, 1H, exchangeable), 8.29 (d, J=8.76 Hz, 1H), 8.23 (br s, 1H), 7.61 (br d, J=8.76 Hz, 1H), 7.45 (d, J=8.81 Hz, 2H), 6.88 (d, J=8.81 Hz, 232 (s, 0.5H).

Example 10

7-Chloro-4-hydroxy-2-(4-hydroxyphenyl)-1,2,5,10-tetrahydropyridazino[4,5-b]quinoline-1,10-dione.

7-Chloro-4-hydroxy-2-(4-methoxyphenyl)-1,2,5,10-tetrahydropyridazino[4,5-b]quinoline-1,10-dione (0.800 g, 2.16 mM) was stirred in methanesulfonic acid (16 mL) to give an amber solution. This solution was heated to 150° C. for 6 hours and cooled to room temperature. Addition of ethyl ether (250 mL) and methanol (50 mL) gave a tan precipitate. The solid was collected and washed with methanol/ether to give the title compound (0.530 g, 51%) as a tan powder, mp 316–318° C.; MS(CI): 356 (M+H).

Analysis for $C_{17}H_{10}ClN_3O_4.CH_3SO_3H$. $1.3 H_2O$: Calculated: C, 45.49; H, 3.52; N, 8.84; Found: C, 45.45; H, 3.24; N, 8.64; NMR: 12.80 (v br s, 1H, exchangeable), 8.15 (d, J=8.68 Hz, 1H), 8.04 (d, J=1.84 Hz, 1H), 7.44 (dd, J=1.84, 8.68 Hz, 1H), 7.28 (d, J=8.74 Hz, 2H), 6.81 (d, J=8.74 Hz, 2H), 2.35 (s, 3H).

Example 11

4-hydroxy-8-nitro-2-phenyl-1,2,5,10-tetrahydropyridazino[4,5-b]quinoline-1,10-dione.

2-Anilino-7-nitro-2,3,4,9-tetrahydro-1H-pyrrolo[3,4-b]quinoline-1,3,9-trione (0.830 g, 2.37 mM) was dissolved with stirring in methanesulfonic acid (42 mL) to give a deep orange solution. Methanol (420 mL) was added and the resulting yellow solution heated to reflux for 2 hours to give a yellow suspension. Heat was removed and the suspension was stirred at room temperature for 3 hours. The solids were removed by filtration, and the filtrate was allowed to stand for 20 hours. More solids formed in the filtrate during this time, and the suspension was refiltered. This filtrate was then concentrated to about 250 mL and diluted with water (400 mL) to give a yellow precipitate. These solids were collected and washed with aqueous methanol (50%) and then ether to give the title compound (0.590 g, 71%) as a yellow powder, mp 382–385° C.; MS(CI): 351 (M+H).

Analysis for $C_{17}H_{10}N_4O_5$. $0.1C_4H_{10}O$. $1.1 H_2O$: Calculated: C, 55.40; H, 3.52; N, 14.80; Found: C, 55.42; H, 3.46; N, 14.60; NMR: 12.91 (br s, 1H, exchangeable), 12.44 (br s, 1H, exchangeable), 8.86 (s, 1H), 8.53 (d, J=9.18 Hz, 1H), 8.15 (d, J=9.18 Hz, 1H), 7.57–7.35 (m, 5H).

The starting material, 2-anilino-7-nitro-2,3,4,9-tetrahydro-1H-pyrrolo-[3,4-b]quinoline-1,3,9-trione, was prepared in the following manner:

a. 2-Anilino-7-nitro-2,3,4,9-tetrahydro-1H-pyrrolo[3,4-b]quinoline-1,3,9-trione.

To a stirred suspension of diethyl 6-nitro-4-hydroxyquinoline-2,3-dicarboxylate (1.670 g, 5.00 mM) in ethanol (30 mL) was added phenylhydrazine (3.44 mL, 35.00 mM) to give a deep red solution. The solution was heated to reflux for 1 hour and concentrated to about 15 mL. Continued heating gave a thick suspension which was diluted with ethanol (5 mL) and refluxed for 16 additional hours. The mixture was cooled to room temperature and filtered to give the phenylhydrazine salt of the title compound as a tan solid. This material was refluxed in glacial acetic acid (25 mL) for 2 hours and cooled to room temperature. Filtration gave the title compound (1.01 g, 58%) as a tan powder, mp 368° C. (decomp.); MS(CI): 351 (M+H).

Analysis for $C_{17}H_{10}N_4O_5$: Calculated: C, 58.30; H, 2.88; N, 16.00; Found: C, 58.21; H, 3.07; N, 16.15; NMR: 8.91 (d, J=2.76 Hz, 1H), 8.60 (dd, J=2.76, 9.18 Hz, 1H), 8.06 (d, J=9.18 Hz, 1H), 7.18 (t, J=7.23 Hz, 2H), 6.82 (m, 3H).

Example 12

2-Benzyl-7-chloro-4-hydroxy-1,2,5,10-tetrahydropyridazino[4,5-b]quinoline-1,10-dione.

To a stirred suspension of dimethyl-7-chloro-4-hydroxyquinoline-2,3-dicarboxylate (5.00 g, 16.90 mM) and benzylhydrazine dihydrochloride (46.15 g, 236.50 mM) in ethanol (100 mL) was added triethylamine (75.8 mL, 541.0 mM). The mixture was heated to give a brown solution which was refluxed for 40 hours during which time a precipitate formed. The suspension was cooled to room temperature and filtered to give the benzylhydrazine salt of the title compound as an impure yellow solid. Multiple crystallizations from ethanolic hydrogen chloride and methanol gave the title compound (0.370 g, 6%) as a white powder, mp 347–350° C.; MS(CI): 354 (M+H).

Analysis for $C_{18}H_{12}ClN_3O_3$: Calculated: C, 61.10; H, 3.42; N, 11.90; Found: C, 60.68; H, 3.61; N, 11.80; NMR:

12.65 (br s, 1H, exchangeable), 11.93 (br s, 1H, exchangeable), 8.15 (d, J=8.67 Hz, 1H), 8.02 (d, J=1.83, 1H), 7.43 (d, J=8.55 Hz, 1H), 7.36–7.23 (m, 5H), 5.11 (s, 2H).

Example 13
7-Chloro-4-hydroxy-2-[2-(4-phenylpiperazino)ethyl]-1,2,5,10-tetrahydropyridazino[4,5-b]quinoline-1,10-dione.

2(2-Bromoethyl)-7-chloro-4-hydroxy-1,2,5,10-tetrahydropyridazino[4,5-b]quinoline-1,10-dione (0.500 g, 1.35 mM) was stirred in dimethylformamide (10 mL), and N-phenylpiperazine (10 mL, 10.6 g, 65.5 mM) was added. The resulting yellow suspension was heated to ~110° C. to form a clear yellow solution. The solution was heated for 6 hours during which time a precipitate formed. The suspension was cooled to room temperature and stirred for five days. The resulting yellow suspension was dissolved into aqueous methanol (500 mL, 50%). The pH of this solution was carefully adjusted to pH=6 with 1N hydrochloric acid (~20 mL) which gave a yellow precipitate. This suspension was stirred for 1 hour and filtered to give the title compound contaminated with N-phenylpiperazine (0.753 g). This material was recrystallized from hot ethanol (200 mL) to give the title compound (0.428 g, 70%) as a yellow powder, mp 361–364° C.; MS(CI): 452 (M+H).

Analysis for $C_{23}H_{22}ClN_5O_3$: Calculated: C, 61.10; H, 4.91; N, 15.50; Found: C, 60.72; H, 5.06; N, 15.30; NMR: 7.95 (d, J=8.67 Hz, 1H), 7.64 (br s, 1H), 7.26–7.18 (m, 3H), 6.95 (d, J=8.07 Hz, 2H), 6.78 (t, J=7.32 Hz, 1H), 4.15 (br s, 2H), 3.55–2.85 (br m, 10H).

Example 14
7-Chloro-1-hydroxy-3-(2-phenethyl)-3,4,5,10-tetrahydropyridazino[4,5-b]quinoline-4,10-dione, choline salt.

To a stirred solution of sodium hydroxide (9.46 g, 236.6 mM) in ethanol (100 mL) at 45° C. was added 2-phenethylhydrazine sulfate salt (27.6 g, 118.3 mM) along with additional ethanol (50 mL). The resulting thick white suspension was stirred for 2 hours. The solids were removed by filtration and washed with ethanol (50 ML). The clear combined filtrates were concentrated to ~75 mL, and dimethyl-7-chloro-4-hydroxyquinoline-2,3-dicarboxylate (2.50 g, 8.45 mM) was added to give a brown solution. The solution was refluxed for 16 hours during which time a yellow precipitate formed. The suspension was filtered hot and washed with ethanol (50 mL) to give the 2-phenethylhydrazine salt of 7-chloro-1-hydroxy-3-(2-phenethyl)-3,4,5,10-tetrahydropyridazino[4,5-b]quinoline-4,10-dione as a yellow powder (2.90 g). This material was refluxed in glacial acetic acid (50 mL) for 2 hours and, after cooling to room temperature, the resulting suspension was filtered to give a mixture of 7-chloro-1-hydroxy-3-(2-phenethyl)-3,4,5,10-tetrahydropyridazino[4,5-b]quinoline-4,10-dione and the corresponding 2-substituted phenethyl isomer as a yellow solid (2.20 g, 68%). This mixture was stirred in methanol (250 mL) and methyl-D-glucamine solution (15.0 g methyl-D-glucamine in 250 mL water). Choline hydroxide solution (9.0 mL, 50 weight % in water) was then added to give a deep amber solution. This solution was carefully acidified to pH 9 with glacial acetic acid whereupon a yellow precipitate formed. After stirring this yellow suspension for 1 hour, the solids were collected and washed successively with aqueous methanol (50%), methanol/ether and ether to give the title compound (free acid, 1.13 g, 54%) as a yellow powder. The filtrate and washes from this collection were saved for use in Example 15.

The 7-Chloro-1-hydroxy-3-(2-phenethyl)-3,4,5,10-tetrahydropyridazino[4,5-b]quinoline-4,10-dione (1.00 g, 2.72 mM) isolated above was stirred in methanol (50 mL), and choline hydroxide solution (1.0 mL, 45 weight % in methanol) was added. The resulting suspension was stirred and sonicated for 1 hour to give an amber solution. This solution was azeotroped 3 times from methanol/toluene (10%, 50 mL) to give an orange solid. Trituration from toluene (50 mL) containing ethanol (3 mL) gave a free-flowing suspension which was stirred for 16 hours. The solids were collected and washed with toluene and ether to give a tan powder (1.19 g). This powder was dried under high vacuum (50 mT) at 100° C. for 72 hours to give the title compound (1.00 g, 78%) as a gold powder, mp 227–229° C.; MS(CI): 368 (M+H).

Analysis for $C_{19}H_{13}ClN_3O_3 \cdot C_5H_{14}NO \cdot 0.2 H_2O$: Calculated: C, 60.70; H, 5.82; N, 11.81; Found: C, 60.41; H, 5.74; N, 11.68; NMR: 14.86 (s, 1H, exchangeable), 8.17 (d, J=8.82 Hz, 1H), 7.80 (s, 1H), 7.33–7.19 (m, 6H), 5.37 (br s, 1H, exchangeable), 4.13 (t, J=7.29 Hz, 2H), 3.84 (br s, 2H), 3.37 (m, 2H), 3.10 (s, 9H), 3.00 (t, J=7.29 Hz, 2H).

Example 15
7-Chloro-4-hydroxy-2-(2-phenethyl)-1,2,5,10-tetrahydropyridazino[4,5,-b]quinoline-1,10-dione.

The filtrate and washes saved from Example 14 were acidified with glacial acetic acid to give a precipitate. The solids were collected and washed successively with methanol, water, methanol, and ether to give the title compound (0.81 g, 39%) as a light yellow powder, mp 327–330° C.; MS(CI): 368 (M+H).

Analysis for $C_{19}H_{14}ClN_3O_3 \cdot 0.1 H_2O$: Calculated: C, 61.70; H, 3.87; N, 11.36; Found: C, 61.60; H, 3.99; N, 10.98; NMR: 12.60 (v br s, 1H, exchangeable), 11.95 (v br s, 1H, exchangeable), 8.15 (d, J=8.63 Hz, 1H), 8.01 (d, J=1.35 Hz, 1H), 7.43 (d, J=8.63 Hz, 1H), 7.33–7.22 (m, 5H), 4.11 (t, J=7.46 Hz, 2H), 2.99 (t, J=7.46 Hz, 2H).

Example 16
7-Chloro-1-hydroxy-3-(4-chlorophenyl)-3,4,5,10-tetrahydropyridazino[4,5-b]quinoline-4,10-dione.

A stirred suspension of 6-chloro-2-(4-chloroanilino)-2,3,4,9- tetrahydro-1H-pyrrolo[3,4-b]quinoline-1,3,9-trione (0.670 g, 1.79 mM) in methanol (60 mL) and methanesulfonic acid (15 mL) was refluxed for 3 hours and cooled to room temperature. The mixture was filtered (the filtrate was saved for use in Example 17), and the collected yellow solids were washed with methanol and ether to give the title compound (0.156 g, 23%) as a yellow powder, mp>400° C.; MS(CI): 374 (M+H).

Analysis for $C_{17}H_9Cl_2N_3O_3$: Calculated: C, 54.60; H, 2.42; N, 11.23; Found: C, 54.29; H, 2.19; N, 11.20; NMR: 13.40 (s, 1H, exchangeable), 12.54 (s, 1H, exchangeable), 8.30 (d, J=8.79 Hz, 1H), 8.23 (d, J=1.89 Hz, 1H), 7.75 (d, J=6.90 Hz, 2H), 7.63 (m, 3H).

The starting material, 6-chloro-2-(4-chloroanilino)-2,3,4, 9-tetrahydro-1H-pyrrolo-[3,4-b]quinoline-1,3,9-trione, was prepared as follows:

a. 6-Chloro-2-(4-chloroanilino)-2,3,4,9-tetrahydro-1H-pyrrolo[3,4-b]quinoline-1,3,9-trione.

To a stirred suspension of dimethyl-7-chloro-4-hydroxyquinoline-2,3-dicarboxylate (2.50 g, 8.45 mM) and 4-chlorophenylhydrazine (10.60 g, 59.20 mM) in ethanol (50 mL) was added triethylamine (9.43 mL) to give a brown solution. This solution was refluxed for 24 hours and then cooled to room temperature. Dilution with water (25 mL) gave a brown precipitate. This suspension was stirred for 16 hours and filtered to remove the solids which were discarded. The filtrate formed another precipitate after standing for seven days. This solid was collected and washed with aqueous methanol (50%) and ether to give the 4-chlorophenylhydrazine salt of the title compound as a brown powder (1.20 g). This material was refluxed in glacial acetic acid (25 mL) for 3 hours and cooled to room temperature. The resulting orange suspension was filtered, and the solids were washed with glacial acetic acid and ether to give the title compound (0.810 g, 25%) as a light orange powder, mp 399–401° C.; MS(CI): 374 (M+H).

Analysis for $C_{17}H_9Cl_2N_3O_3$: Calculated: C, 54.60; H, 2.42; N, 11.23; Found: C, 54.29; H, 2.61; N, 11.12; NMR: 13.80 (v br s, 1H, exchangeable), 8.67 (s, 1H, exchangeable), 8.22 (d, J=8.67 Hz, 1H), 7.88 (d, J=1.73 Hz, 1H), 7.57 (dd, J=1.73, 8.67 Hz, 1H), 7.21 (d, J=8.79 Hz, 2H), 6.87 (d, J=8.79 Hz, 2H).

Example 17
7-Chloro-4-hydroxy-2-(4-chlorophenyl)-1,2,5,10-tetrahydropyridazino[4,5-b]quinoline-1,10-dione.

The filtrate saved from Example 16 was diluted with water (75 mL) to give a white suspension which was stirred for 16 hours. This suspension was filtered, and the collected solids were washed successively with water, aqueous methanol, methanol/ether and ether to give the title compound (0.420 g, 63%) as a white powder, mp 359–360° C.; MS(CI): 374 (M+H). Analysis for $C_{17}H_9Cl_2N_3O_3$. 0.5 $H_2O$. $0.2CH_3SO_3H$: Calculated: C, 51.30; H, 2.71; N, 10.40; Found: C, 51.44; H, 2.64; N, 0.60; NMR: 12.91 (br s, 1H, exchangeable), 12.07 (br s, 1H, exchangeable), 8.16 (d, J=8.64 Hz, 1H), 8.06 (d, J=1.62 Hz, 1H), 7.63–7.46 (m, 5H).

Example 18
7-Chloro-1-hydroxy-3-(4-methylphenyl)-3,4,5,10-tetrahydropyridazino[4,5-b]quinoline-4,10-dione.

A stirred suspension of 6-chloro-2-(4-methylanilino)-2,3,4,9-tetrahydro-1H-pyrrolo[3,4-b]quinoline-1,3,9-trione (1.60 g, 4.53 mM) in a solution of methanol (128 mL) and methanesulfonic acid (32 mL) was refluxed for 4 hours and cooled to room temperature. The resulting yellow suspension was stirred at room temperature for five days and then filtered (the filtrate was saved for use in Example 19). The collected solids were washed with methanol and then ether to give the title compound (0.594 g, 37%) as a yellow powder, mp>400° C.; MS(CI): 354 (M+H).

Analysis for $C_{18}H_{12}ClN_3O_3$. 0.4 $H_2O$: Calculated: C, 59.89; H, 3.57; N, 11.64; Found: C, 59.47; H, 3.14; N, 11.57; NMR: 13.34 (s, 1H, exchangeable), 12.48 (s, 1H, exchangeable), 8.30 (d, J=8.75 Hz, 1H), 8.22 (br s, 1H), 7.62 (d, J=8.75 Hz, 1H), 7.55 (d, J=8.01 Hz, 2H), 7.33 (d, J=8.01 Hz, 2H), 2.38 (s, 3H).

The starting material, 6-chloro-2-(4-methylanilino)-2,3,4,9-tetrahydro-1H-pyrrolo-[3,4-b]quinoline-1,3,9-trione, was prepared in the following manner:

a. 6-Chloro-2-(4-methylanilino)-2,3,4,9-tetrahydro-1H-pyrrolo[3,4-b]quinoline-1,3,9-trione.

To a stirred suspension of dimethyl-7-chloro-4-hydroxyquinoline-2,3-dicarboxylate (3.90 g, 13.3 mM) and 4-methylphenylhydrazine hydrochloride (14.8 g, 93.2 mM) in ethanol (140 mL) was added triethylamine (14.8 mL, 106.4 mM). The resulting brown solution was refluxed for 16 hours during which time a precipitate formed. The resulting suspension was cooled to room temperature and filtered to give the 4-methylphenylhydrazine salt of the title compound as a grey powder (2.30 g). This material was refluxed in glacial acetic acid (45 mL) for 2 hours and cooled to room temperature. The resulting brown suspension was filtered to give the title compound (1.60 g, 34%) as a tan powder, mp 380–382° C.; MS(CI): 354 (M+H).

Analysis for $C_{18}H_{12}ClN_3O_3$. 0.2 $H_2O$: Calculated: C, 60.49; H, 3.50; N, 11.76; Found: C, 60.66; H, 3.26; N, 11.76; NMR: 13.81 (v br s, 1H, exchangeable), 8.39 (s, 1H, exchangeable), 8.22 (d, J=8.58 Hz, 1H), 7.89 (d, J=1.97 Hz, 1H), 7.58 (dd, J=1.97, 8.58 Hz, 1H), 6.98 (d, J=8.28 Hz, 2H), 6.73 (d, J=8.28 Hz, 2H), 2.19 (s, 3H).

Example 19
7-Chloro-4-hydroxy-2-(4-methylphenyl)-1,2,5,10-tetrahydropyridazino[4,5-b]quinoline-1,10-dione.

The filtrate saved from Example 18 was diluted with water (160 mL) to give a tan suspension which was stirred for 3 hours. The suspension was filtered, and the collected solids were washed successively with water, methanol/ether, and ether to give the title compound (0.855 g, 53%) as a tan powder, mp 368–370° C.; MS(CI): 354 (M+H).

Analysis for $C_{18}H_{12}ClN_3O_3$. 0.2 $H_2O$: Calculated: C, 60.50; H, 3.50; N, 11.76; Found: C, 60.52; H, 3.23; N, 11.79; NMR: 12.75 (br s, 1H, exchangeable), 12.00 (br s, 1H, exchangeable), 8.15 (d, J=8.61 Hz, 1H), 8.04 (d, J=1.50 Hz, 1H), 7.43 (m, 3H), 7.26 (d, J=8.25 Hz, 2H), 2.36 (s, 3H).

Example 20
7-Chloro-1-hydroxy-3-(4-isopropylphenyl)-3,4,5,10-tetrahydropyridazino[4,5-b]quinoline-4,10-dione.

A stirred suspension of 6-chloro-2-(4-isopropylanilino)-2,3,4,9-tetrahydro-1H-pyrrolo[3,4-b]quinoline-1,3,9-trione (1.13 g, 2.98 mM) in a solution of methanol (90 mL) and methanesulfonic acid (23 mL) was refluxed for 7 hours and cooled to room temperature. The mixture was filtered (the filtrate was saved for use in Example 21), and the collected yellow solids were washed with methanol and ether to give the title compound (0.401 g, 35%) as a yellow powder, mp 393–394° C.; MS(CI): 382 (M+H).

Analysis for $C_{20}H_{16}ClN_3O_3$. 0.2 $H_2O$: Calculated: C, 62.33; H, 4.29; N, 10.90; Found: C, 62.16; H, 3.98; N, 10.82; NMR: 13.33 (s, 1H, exchangeable), 12.48 (s, 1H, exchangeable), 8.28 (d, J=8.76 Hz, 1H), 8.22 (d, J=1.77 Hz, 1H), 7.63–7.58 (m, 3H), 7.40 (d, J=8.49 Hz, 2H), 2.98 (septet, J=6.96 Hz, 1H), 1.25 (d, J=6.96 Hz, 6H).

The starting material, 6-chloro-2-(4-isopropylanilino)-2,3,4,9-tetrahydro-1H-pyrrolo[3,4-b]quinoline-1,3,9-trione, was prepared in the following manner:

a. 6-Chloro-2-(4-isopropylanilino)-2,3,4,9-tetrahydro-1H-pyrrolo[3,4-b]quinoline-1,3,9-trione.

To a stirred suspension of dimethyl-7-chloro-4-hydroxyquinoline-2,3-dicarboxylate (2.01 g, 6.80 mM) and 4-isopropylphenylhydrazine hydrochloride (8.90 g, 47.6 mM) in ethanol (72 mL) was added triethylamine (7.6 mL, 54.5 mM) to give a brown solution. This solution was refluxed for 16 hours, cooled to room temperature, and then added slowly to a mixture of hydrochloric acid (12N, 100 mL) and ice (100 mL) with vigorous stirring whereupon a pink suspension formed. The suspension was filtered, and the collected solids were washed with a cold solution made by mixing methanol (100 mL), hydrochloric acid (100 mL, 12N) and ice (100 g) to give the 4-isopropylphenylhydrazine salt of the title compound as a purple powder (1.80 g). This material was refluxed in glacial acetic acid (15 mL) for 3 hours to give a tan suspension. The suspension was cooled to room temperature and filtered. The collected solids were washed with glacial acetic acid (10 mL) and ether to give the title compound (1.125 g, 43%) as a tan powder, mp 367–369° C.; MS(CI): 382 (M+H).

Analysis for $C_{20}H_{16}ClN_3O_3$. 0.1 $H_2O$: Calculated: C, 62.60; H, 4.26; N, 10.95; Found: C, 62.60; H, 4.35; N, 10.73;

NMR: 13.82 (v br s, 1H, exchangeable), 8.41 (s, 1H, exchangeable), 8.23 (d, J=8.64 Hz, 1H), 7.89 (d, J=1.98 Hz, 1H), 7.61 (dd, J=1.98, 8.64 Hz, 1H), 7.04 (d, J=8.42 Hz, 2H), 6.74 (d, J=8.42 Hz, 2H), 2.78 (septet, J=6.87 Hz, 1H), 1.15 (d, J=6.87 Hz, 6H).

Example 21

7-Chloro-4-hydroxy-2-(4-isopropylphenyl)-1,2,5,10-tetrahydropyridazino[4,5-b]quinoline-1,10-dione.

The filtrate saved from Example 20 was diluted with water (115 mL) to give a light yellow suspension which was stirred for 5 hours at room temperature. The suspension was filtered, and the collected solids were washed successively with water, aqueous methanol (50%), methanol/ether and ether to give the title compound (0.418 g, 37%) as a tan powder, mp 323–326° C.; MS(CI): 382 (M+H).

Analysis for $C_{20}H_{16}ClN_3O_3 \cdot 0.5 H_2O \cdot 0.1 CH_3SO_3H$: Calculated: C, 60.29; H, 4.38; N, 10.49; Found: C, 60.13; H, 4.10; N, 10.40; NMR: 12.73 (br s, 1H, exchangeable), 12.00 (br s, 1H, exchangeable), 8.15 (d, J=8.70 Hz, 1H), 8.05 (d, J=1.74 Hz, 1H), 7.45 (m, 3H), 7.33 (d, J=8.40 Hz, 2H), 2.95 (septet, J=6.90 Hz, 1H), 1.24 (d, J=6.90 Hz, 6H).

Example 22

7,9-Dichloro-4-hydroxy-2-phenyl-1,2,5,10-tetrahydropyridazino[4,5-b]quinoline-1,10-dione.

6,8-Dichloro-2-anilino-2,3,4,9-tetrahydro-1H-pyrrolo[3,4-b]quinoline-1,3,9-trione (0.60 g, 1.60 mM) was stirred in methanol (200 mL) and methanesulfonic acid (20 mL) was added with cooling, maintaining the temperature below 20° C. The resulting orange solution was stirred overnight at room temperature. A precipitate formed overnight and the orange suspension was heated to reflux for 1 hour. The suspension was cooled to room temperature and allowed to stand overnight without stirring. The suspension was filtered and the filtrates were slowly diluted with water (200 mL) to give a yellow suspension. This suspension was stirred for two hours and the solids were collected and washed with water, aqueous methanol, 50% methanol/ether, and ether to give the title compound (0.368 g, 61%) as a light tan powder, mp 361–363° C.; MS(CI): 374 (M+H).

Analysis for $C_{17}H_9Cl_2N_3O_3 \cdot 0.30 H_2O$: Calculated: C, 53.80; H, 2.55; N, 11.07 Found: C, 53.71; H, 2.64; N, 10.97 1H NMR 12.84 (s, 1H, exchangeable), 11.96 (s, 1H, exchangeable), 8.04 (d, J=2.02 Hz, 1H), 7.55–7.45 (m, 5H), 7.36 (t, J=6.84 Hz, 1H).

The starting material, 6,8-dichloro-2-anilino-2,3,4,9-tetrahydro-1H-pyrrolo[3,4-b]quinoline-1,3,9-trione, was prepared in the following manner:

a. 6,8-Dichloro-2-anilino-2,3,4,9-tetrahydro-1H-pyrrolo[3,4-b]quinoline-1,3,9-trione.

To a stirred suspension of dimethyl-5,7-dichloro-4-hydroxyquinoline-2,3-dicarboxylate (3.00 g, 9.09 mM) in ethanol (42 mL) was added phenylhydrazine (6.26 mL, 63.6 mM). The resulting green solution was heated to reflux for 16 hours during which time a small amount of red precipitate formed. This suspension was cooled to room temperature with stirring and additional precipitation occurred to give a thick tan suspension. The solids were collected and washed with ethanol (the ethanol washes were saved). The collected solids were recrystallized from ethanol (1.20 L) to give the phenylhydrazine salt of the title compound (1.17 g) as a tan powder. This material was stirred and refluxed in glacial acetic acid (15 mL) for 2.5 hours and then cooled to room temperature with stirring. The resulting orange suspension was filtered to give the title compound (0.629 g, 19%) as an orange powder which was slightly impure. An analytical sample of the title compound was obtained from the above saved ethanol washes by filtration of a precipitate which formed after these washes stood for several hours. Recrystallization of this collected tan powder (0.126 g) from glacial acetic acid (2 mL) gave the pure title compound (0.083 g) as an orange powder, mp 364–367° C.; MS(CI): 374 (M+H).

Analysis for $C_{17}H_9Cl_2N_3O_3 \cdot 0.30 H_2O \cdot 0.10 CH_3CO_2H$: Calculated: C, 53.60; H, 2.61; N, 10.90 Found: C, 53.49; H, 2.77, N, 10.82 1H NMR 8.53 (s, 1H, exchangeable), 7.85 (d, J=1.94 Hz, 1H), 7.65 (d, J=1.94 Hz, 1H), 7.18 (t, J=7.84 Hz, 2H), 6.82 (d, J=7.84 Hz, 3H).

Example 23

7-Chloro-1-hydroxy-3-(1-naphthyl)-3,4,5,10-tetrahydropyridazino[4,5-b]quinoline-4,10-dione.

6-Chloro-2-(1-naphthylamino)-2,3,4,9-tetrahydro-1H-pyrrolo[3,4-b]quinoline-1,3,9-trione (1.30 g, 3.34 mM) was stirred in methanol (0.65 L) and methanesulfonic acid (65 mL) was added. The brown suspension was heated to reflux for 16 hours during which the solids dissolved to give a brown solution. This solution was cooled to room temperature. Addition of ice (10 mL) gave a tan suspension which was stirred for 1.5 hours. The suspension was filtered (the filtrate was saved for use in Example 24) and the collected solids were washed with methanol and ether to give the title compound (0.560 g, 43%) as a dull yellow powder, mp 374–376° C.; MS(CI): 390 (M+H).

Analysis for $C_{21}H_{12}ClN_3O_3 \cdot 0.20 H_2O$: Calculated: C, 64.10; H, 3.18; N, 10.68 Found: C, 63.91; H, 3.42; N, 10.61 1H NMR 13.40 (s, 1H, exchangeable), 12.58 (s, 1H, exchangeable), 8.35 (d, J=8.70 Hz, 1H), 8.25 (d, J=1.76 Hz, 1H), 8.12–8.07 (m, 2H), 7.74–7.53 (m, 6H).

The starting material, 6-chloro-2-(1-naphthylamino)-2,3,4,9-tetrahydro-1H-pyrrolo-[3,4-b]quinoline-1,3,9-trione, was prepared as follows:

a. 6-Chloro-2-(1-naphthylamino)-2,3,4,9-tetrahydro-1H-pyrrolo[3,4-b]quinoline-1,3,9-trione.

To a stirred suspension of dimethyl-7-chloro-4-hydroxyquinoline-2,3-dicarboxylate (2.00 g, 6.80 mM) and 1-naphthylhydrazine hydrochloride (9.26 g, 47.6 mM) in ethanol (72 mL) was added triethylamine (7.60 mL) to give a brown solution. After refluxing for 4 days, the solution was cooled to room temperature and diluted with ethyl acetate (0.35 L) to give a tan suspension. This suspension was filtered to remove the solids which were discarded. The filtrate was then poured into ethyl acetate (500 mL) which was washed with hydrochloric acid (3×500 mL, 1N). The washed solution was diluted with ether (250 mL) to give a tan suspension. The solids were collected to give the 1-naphthylhydrazine salt of the title compound as a tan powder (2.09 g). This material was refluxed in glacial acetic acid (50 mL) for 2 hours, cooled to room temperature and filtered. The collected solids were washed with glacial acetic acid and ether to give the title compound (1.44 g, 54%) as a tan powder, mp 368° C. (decomp.); MS(CI): 390 (M+H).

Analysis for $C_{21}H_{12}ClN_3O_3 \cdot 0.30 CH_3CO_2H$: Calculated: C, 63.60; H, 3.26; N, 10.30 Found: C, 63.90; H, 3.43; N, 9.97 1H NMR 9.06 (s, 1H, exchangeable), 8.27–8.22 (m, 2H), 7.92–7.88 (m, 2H), 7.63–7.52 (m, 3H), 7.41 (d, J=8.17 Hz, 1H), 7.27 (t, J=7.86 Hz, 1H), 6.80 (d, J=7.86 Hz, 1H).

Example 24

7-Chloro-4-hydroxy-2-(1-naphthyl)-1,2,5,10-tetrahydropyridazino[4,5-b]quinoline-1,10-dione.

The filtrate saved from Example 23 was diluted with water (0.75 L) and then partially concentrated on a rotary evaporator to give a brown suspension. The solids from the suspension were collected and washed with water, methanol/ether and ether to give a brown powder (0.535 g). This material was heated to reflux in methanol (23 mL) and filtered hot to remove undissolved solids which were discarded. The filtrate was concentrated to dryness and triturated with ethyl acetate (20 mL). The resulting suspension was filtered and the collected solids washed with ethyl acetate and ether to give the title compound (0.240 g, 18%) as a grey powder, mp 335–337° C.; MS(CI): 390 (M+H).

Analysis for $C_{21}H_{12}ClN_3O_3$. 0.60 $H_2O$. 0.40 $CH_3SO_3H$. 0.20 $C_4H_{10}O$. 0.15 $C_4H_8O_2$: Calculated: C, 58.60; H, 3.88; N, 9.00 Found: C, 58.37; H, 3.53; N, 9.14 1H NMR 12.80 br s, 1H, exchangeable), 12.1 (br s, 1H, exchangeable), 8.15–8.03 (br m, 4H), 7.67–7.50 (br m, 6H).

Example 25
7-Chloro-3-(4-fluorophenyl)-1-hydroxy-3,4,5,10-tetrahydropyridazino[4,5-b]quinoline-4,10-dione.

A stirred suspension of 6-chloro-2-(4-fluoroanilino)-2,3,4,9-tetrahydro-1H-pyrrolo[3,4-b]quinoline-1,3,9-trione (1.40 g, 3.90 mM) in a solution of methanol (0.73 L) and methanesulfonic acid (73 mL) was refluxed for 16 hours and cooled to room temperature. The resulting orange suspension was filtered (the filtrate was saved for use in Example 26) and the collected solids were washed successively with methanol and ether to give the title compound (0.374 g, 27%) as a light orange powder, mp>400° C.; MS(CI): 358 (M+H).

Analysis for $C_{17}H_9ClFN_3O_3.H_2O$: Calculated: C, 54.30; H, 2.95; N, 11.20 Found: C, 54.08; H, 2.62; N, 10.98 1H NMR 13.38 (s, 1H, exchangeable), 12.51 (s, 1H, exchangeable), 8.30 (d, J=8.75 Hz, 1H), 8.22 (d, J=1.78 Hz, 1H), 7.76–7.71 (m, 2H), 7.63 (dd, J=1.78, 8.75 Hz, 1H), 7.40–7.35 (m, 2H).

The starting material, 6-chloro-2-(4-fluoroanilino)-2,3,4,9-tetrahydro-1H-pyrrolo-[3,4-b]quinoline-1,3,9-trione, was prepared in the following manner:

a. 6-Chloro-2-(4-fluoroanilino)-2,3 4,9-tetrahydro-1H-pyrrolo [3,4-b]quinoline-1,3,9-trione.

To a stirred suspension of dimethyl-7-chloro-4-hydroxyquinoline-2,3-dicarboxylate (2.59 g, 8.79 mM) and 4-fluorophenylhydrazine hydrochloride (10.0 g, 61.5 mM) in ethanol (48 mL) was added triethylamine (9.8 mL, 70.3 mM). The resulting brown solution was refluxed for 48 hours, cooled to room temperature and diluted with ethyl acetate (150 mL) to give a white crystalline precipitate which was removed by filtration and discarded. The filtrate was washed with hydrochloric acid (3×500 mL, 1N) which caused precipitation in the ethyl acetate layer. The precipitate was collected and washed successively with ethyl acetate/ether and ether to give the 4-fluorophenylhydrazine salt of the title compound (2.14 g). This material was refluxed in glacial acetic acid (20 mL) for 2 hours. After cooling the acetic acid solution to room temperature, a precipitate formed and the solids were collected to give the title compound (1.48 g, 47%) as a yellow powder, mp 390–392° C.; MS(CI): 358 (M+H).

Analysis for $C_{17}H_9ClFN_3O_3$. 0.40 $H_2O$: Calculated: C, 55.95; H, 2.71; N, 11.51 Found: C, 56.01; H, 2.67; N, 11.54 1H NMR 13.78 (br s, 1H, exchangeable), 8.52 (s, 1H, exchangeable), 8.22 (d, J=8.71 Hz, 1H), 7.89 (d, J=2.01 Hz, 1H), 7.58 (dd, J=2.01, 8.71 Hz, 1H), 7.05–6.98 (m, 2H), 6.89–6.85 (m, 2H).

Example 26
7-Chloro-2-(4-fluorophenyl)-4-hydroxy-1,2,5,10-tetrahydropyridazino[4,5-b]quinoline-1,10-dione.

The filtrate saved from Example 25 was diluted with water (800 mL) to give a light green suspension which was stirred for 3 hours. The suspension was filtered and the collected solids were washed successively with water, methanol/ether and ether to give the title compound (0.910 g, 65%) as a grey powder, mp 353–356° C.; MS(CI): 358 (M+H).

Analysis for $C_{17}H_9ClFN_3$. 2.00 $H_2O$. 0.06 $CH_3SO_3H$: Calculated: C, 51.30; H, 3.34; N, 10.52 Found: C, 51.58; H, 3.00; N, 10.47 1H NMR 11.95 (br s, 1H, exchangeable), 12.50 (br s, 1H, exchangeable), 8.15 (br d, J=8.26 Hz, 1H), 8.07 (br s, 1H), 7.58 (br s, 2H), 7.43 (br d, J=8.26 Hz, 1H), 7.29–7.24 (br m, 2H).

Example 27
3-(4-Bromophenyl)-7-chloro-1-hydroxy-3,4,5,10-tetrahydropyridazino[4,5-b]quinoline-4,10-dione.

A stirred suspension of 2-(4-bromoanilino)-6-chloro-2,3,4,9-tetrahydro-1H-pyrrolo[3,4-b]quinoline-1,3,9-trione (1.00 g, 2.39 mM) in a solution of methanol (500 mL) and methanesulfonic acid (50 mL) was refluxed for 16 hours and cooled to room temperature. The resulting yellow suspension was filtered (the filtrate was saved for use in Example 28). The collected solids were washed with methanol and then ether to give the title compound (0.222 g, 22%) as a yellow powder, mp>400° C.; MS(CI): 420 (M+H).

Analysis for $C_{17}H_9BrClN_3O_3$. 0.30 $H_2O$: Calculated: C, 48.15; H, 2.28; N, 9.91 Found: C, 48.15; H, 2.36; N, 9.88 1H NMR 13.36 (s, 1H, exchangeable), 12.51 (s, 1H, exchangeable), 8.25 (d, J=8.73 Hz, 1H), 8.19 (d, J=1.55 Hz, 1H), 7.75–7.67 (m, 4H), 7.60 (dd, J=1.55, 8.73 Hz, 1H).

The starting material, 2-(4-bromoanilino)-6-chloro-2,3,4,9-tetrahydro-1H-pyrrolo-[3,4-b]quinoline-1,3,9-trione, was prepared in the following manner:

a. 2-(4-Bromoanilino)-6-chloro-2,3,4,9-tetrahydro-1H-pyrrolo[3,4-b]quinoline-1,3,9-trione.

To a stirred suspension of dimethyl-7-chloro-4-hydroxyquinoline-2,3-dicarboxylate (1.90 g, 6.40 mM) and 4-bromophenylhydrazine hydrochloride (10.0 g, 44.7 mM) in ethanol (35 mL) was added triethylamine (7.1 mL, 51.1 mM). The resulting brown solution was refluxed for 22 hours during which time a tan precipitate formed. This mixture was cooled to room temperature and filtered to give the 4-bromophenylhydrazine salt of the title compound as a white powder (1.69 g). This material was refluxed in glacial acetic acid (20 mL) for 3 hours and cooled to room temperature. The resulting tan suspension was filtered and the solids washed with glacial acetic acid and then ether to give the title compound (1.15 g, 43%) as a tan powder, mp 393–394° C.; MS(CI): 420 (M+H).

Analysis for $C_{17}H_9BrClN_3O_3$: Calculated: C, 48.77; H, 2.17; N, 10.04 Found: C, 48.52; H, 2.26; N, 10.00 1H NMR 13.84 (br s, 1H, exchangeable), 8.71 (s, 1H, exchangeable), 8.23 (d, J=8.63 Hz, 1H), 7.89 (d, J=1.98 Hz, 1H), 7.58 (dd, J=1.98, 8.63 Hz, 1H), 7.32 (d, J=8.70 Hz, 2H), 6.84 (d, J=8.70 Hz, 2H).

Example 28
2-(4-Bromophenyl)-7-chloro-4-hydroxy-1,2,5,10-tetrahydropyridazino[4,5-b]quinoline-1,10-dione.

The filtrate saved from Example 27 was diluted with water (550 mL) to give a tan suspension which was stirred for 2 hours. The suspension was filtered and washed successively with water, methanol/ether and ether to give the title compound (0.716 g, 72%) as a tan powder, mp 359–361° C.; MS(CI): 420 (M+H).

Analysis for C17H9BrClN3O3. 1.30 H2O: Calculated: C, 46.20; H, 2.64; N, 9.51 Found: C, 46.26; H, 2.66; N, 9.37 1H NMR 12.60 (br s, 1H, exchangeable), 11.95 (br s, 1H, exchangeable), 8.16 (d, J=8.61 Hz, 1H), 8.06 (d, J=1.67 Hz, 1H), 7.64 (d, J=8.78 Hz, 2H), 7.55 (d, J=8.78 Hz, 2H), 7.43 (d, J=8.61 Hz, 1H).

Example 29
7-Chloro-1-hydroxy-3-(2-methoxyphenyl)-3,4,5,10-tetrahydropyridazino[4,5-b]quinoline-4,10-dione.

A stirred suspension of 6-chloro-2-(2-methoxyanilino)-2,3,4,9-tetrahydro-1H-pyrrolo[3,4-b]quinoline-1,3,9-trione (1.78 g, 4.81 mM) in a solution of methanol (285 mL) and methanesulfonic acid (89 mL) was refluxed for 8 hours during which time a tan precipitate formed. The resulting suspension was cooled to room temperature and stirred for 16 hours. The suspension was filtered (the filtrate was saved for use in Example 30) and the collected solids were washed with methanol and then ether to give the title compound (0.889 g, 50%) as a yellow powder, mp 356–359° C.; MS(CI): 370 (M+H).

Analysis for C18H12ClN3O4. 1.20 CH3OH: Calculated: C, 56.50; H, 4.15; N, 10.30 Found: C, 56.50; H, 4.15; N, 10.55 1H NMR 13.34 (s, 1H, exchangeable), 12.45 (s, 1H, exchangeable), 8.30 (d, J=8.61 Hz, 1H), 8.21 (s, 1H), 7.63 (d, J=8.61 Hz, 1H), 7.48 (t, J=8.10 Hz, 1H), 7.40 (d, J=7.46 Hz, 1H), 7.23 (d, J=8.10 Hz, 1H), 7.10 (t, J=7.46 Hz, 1H), 3.77 (s, 3H).

The starting material, 6-chloro-2-(2-methoxyanilino)-2,3,4,9-tetrahydro-1H-pyrrolo-[3,4-b]quinoline-1,3,9-trione, was prepared in the following manner:

a. 6-Chloro-2-(2-methoxyanilino)-2,3,4,9-tetrahydro-1H-pyrrolo-[3,4-b]quinoline-1,3,9-trione.

To a stirred suspension of dimethyl-7-chloro-4-hydroxyquinoline-2,3-dicarboxylate (0.218 g, 0.74 mM) and 2-methoxyphenylhydrazine hydrochloride (0.900 g, 5.20 mM) in ethanol (4 mL) was added triethylamine (0.83 mL, 5.9 mM). The resulting brown solution was refluxed for 22 hours. The solution was cooled to room temperature and precipitation occurred to give a tan suspension which was stirred for 16 hours. The suspension was filtered and the collected solids were discarded. The filtrate was diluted with ethyl acetate (50 mL) and washed with hydrochloric acid (3×50 mL, 1N) and brine (50 mL). Concentration of the washed solution under a nitrogen gas stream gave a tan powder (0.527 g). This material was refluxed in glacial acetic acid (5 mL) for 2 hours to give a thick tan suspension. This suspension was cooled to room temperature and stirred for 16 hours. The suspension was filtered and the collected solids washed with glacial acetic acid and then ether to give a tan powder (0.378 g). This material was stirred in a solution of water (5 mL) and methanol (1 mL) to give a tan suspension which was stirred for 16 hours. The suspension was filtered and the collected solids were washed successively with water, methanol and then ether to give the title compound (0.126 g, 46%) as a tan powder, mp 390° C. (decomp.); MS(CI): 370 (M+H).

Analysis for C18H12ClN3O4. 0.20 H2O: Calculated: C, 57.90; H, 3.35; N, 11.25 Found: C, 57.92; H, 3.48; N, 10.93 1H NMR 13.80 (br s, 1H, exchangeable), 8.23 (d, J=8.67 Hz, 1H), 7.89 (d, J=1.98 Hz, 1H), 7.79 (s, 1H, exchangeable), 7.58 (dd, J=1.98, 8.67 Hz, 1H), 6.97 (d, J=7.62 Hz, 1H), 6.80–6.73 (m, 3H), 3.86 (s, 3H).

Example 30
7-Chloro-4-hydroxy-2-(2-methoxyphenyl)-1,2,5,10-tetrahydropyridazino[4,5-b]quinoline-1,10-dione.

The filtrate saved from Example 30 was diluted with water (600 mL) to give a tan suspension which was stirred at 0° C. for 1 hour and filtered to remove the solids. The filtrate was partially concentrated under a nitrogen gas stream to give a white suspension. This suspension was filtered and the collected solids were washed with water to give the title compound (0.347 g, 19%) as a white powder, mp 347–349° C.; MS(CI): 370 (M+H).

Analysis for C18H12ClN3O4. 1.30 H2O. 0.10 CH3SO3H: Calculated: C, 54.00; H, 3.75; N, 10.43 Found: C, 54.07; H, 3.33; N, 10.41 1H NMR 12.68 (br s, 1H, exchangeable), 12.00 (br s, 1H, exchangeable), 8.16 (d, J=8.61 Hz, 1H), 8.07 (s, 1H), 7.48–7.40 (m, 2H), 7.32 (d, J=7.59 Hz, 1H), 7.16 (d, J=8.31 Hz, 1H), 7.05 (t, J=7.59 Hz, 1H), 3.75 (s, 3H).

Example 31
7-Chloro-4-hydroxy-2-(2-hydroxyphenyl)-1,2,5,10-tetrahydropyridazino[4,5-b]quinoline-1,10-dione.

A solution of 7-chloro-4-hydroxy-2-(2-methoxyphenyl)-1,2,5,10-tetrahydropyridazino[4,5-b]quinoline-1,10-dione (0.288 g, 0.78 mM) in methanesulfonic acid (5 mL) was heated to 140° C. for 7 hours and cooled to room temperature. The brown solution was diluted with water (5 mL) which caused an exotherm to 80° C. and a precipitate formed to give a brown suspension. This suspension was further diluted with water (10 mL) and filtered. The collected solids were washed with water (25 mL) and ether to give a brown solid (0.23 g). This material was suspended in water (13 mL) and choline hydroxide solution (45 wt % in methanol, 0.5 mL) was added to give a brown solution. This solution was warmed to 50° C. for 2 hours and cooled to room temperature. Hydrochloric acid (5 mL, 1N) was added to give a grey suspension. This suspension was filtered and the collected solids were washed with water and then ether to give the title compound (0.225 g, 81%) as a grey powder, mp>400° C.; MS(CI): 356 (M+H).

Analysis for C17H10ClN3O4. 0.80 H2O. 0.10 C4H10O: Calculated: C, 55.35; H, 3.36; N, 11.13 Found: C, 55.53; H, 3.00; N, 10.89 1H NMR 12.68 (s, 1H, exchangeable), 12.01 (s, 1H, exchangeable), 9.53 (s, 1H, exchangeable), 8.16 (d, J=8.18 Hz, 1H), 8.06 (s, 1H), 7.46 (d, J=8.18 Hz, 1H), 7.23 (m, 2H), 6.95 (d, J=7.80 Hz, 1H), 6.87 (t, J=7.17 Hz, 1H).

Example 32
7-Chloro-1-hydroxy-3-(3-methoxyphenyl)-3,4,5,10-tetrahydropyridazino[4,5-b]quinoline-4,10-dione.

A stirred suspension of 6-chloro-2-(3-methoxyanilino)-2,3,4,9-tetrahydro-1H-pyrrolo[3,4-b]quinoline-1,3,9-trione (1.85 g, 5.00 mM) in a solution of methanol (0.93 L) and methanesulfonic acid (93 mL) was refluxed for 16 hours to give a tan suspension. This suspension was cooled to room temperature and stirred for 24 hours. The suspension was filtered (the filtrate saved for use in Example 33) and the collected solids were washed with methanol and then ether to give the title compound (0.385 g, 21%) as a tan powder, mp 393–395° C.; MS(CI): 370 (M+H).

Analysis for C18H12ClN3O4. 0.50 H2O. 0.05 CH3OH: Calculated: C, 57.00; H, 3.50; N, 11.05 Found: C, 56.73; H, 3.11; N, 10.98 1H NMR 13.35 (s, 1H, exchangeable), 12.47 (s, 1H, exchangeable), 8.28 (d, J=8.75 Hz, 1H), 8.20 (d, J=1.83 Hz, 1H), 7.60 (dd, J=1.83, 8.75 Hz, 1H), 7.47–7.42 (t, J=8.06 Hz, 1H), 7.28–7.26 (m, 2H), 7.01 (dd, J=1.38, 8.06 Hz, 1H), 3.81 (s, 3H).

The starting material, 6-chloro-2-(3-methoxyanilino)-2,3,4,9-tetrahydro-1H-pyrrolo-[3,4-b]quinoline-1,3,9-trione, was prepared in the following manner:

a. 6-Chloro-2-(3-methoxyanilino)-2,3,4,9-tetrahydro-1H-pyrrolo[3,4-b]quinoline-1,3,9-trione.

To a stirred suspension of dimethyl-7-chloro-4-hydroxyquinoline-2,3-dicarboxylate (4.61 g, 15.6 mM) and 3-methoxyphenylhydrazine hydrochloride (19.10 g, 109 mM) in ethanol (84 mL) was added triethylamine (17.4 mL, 125 mM). The resulting brown solution was refluxed for 40 hours and cooled to room temperature. Ethyl acetate (430 mL) was added to give a tan suspension. This suspension was filtered to remove the solids which were discarded. The filtrate was washed with hydrochloric acid (3×750 mL, 1N) which caused precipitation from the ethyl acetate layer. This ethyl acetate suspension was filtered to give a tan solid (0.940 g). The filtrate was saved. The combined hydrochloric washes were re-extracted with ethyl acetate and these extracts were combined with the saved ethyl acetate filtrate from above. This solution was concentrated to provide a solid which was triturated with ether/ethyl acetate to give a tan suspension. This suspension was filtered to give a second crop of tan solid (1.60 g). The filtrate was concentrated to a solid and triturated with ether/ethyl acetate to give a suspension. This suspension was filtered to give a third crop of tan solid (0.70 g). The solids saved from the above filtrations were combined (3.24 g) and refluxed in glacial acetic acid (32 mL) for 3 hours. The resulting suspension was cooled to room temperature and stirred for 16 hours. This suspension was filtered and the collected solids were washed with glacial acetic acid, and then ether to give the title compound (1.93 g, 33 %) as a tan powder, mp 369° C. (decomp.); MS(CI): 370 (M+H).

Analysis for C18H12ClN3O4. 0.50 H2O: Calculated: C, 57.10; H, 3.46; N, 11.10 Found: C, 57.21; H, 3.53; N, 10.86 1H NMR 13.75 (br s, 1H, exchangeable), 8.51 (s, 1H, exchangeable), 8.23 (d, J=8.69 Hz, 1H), 7.89 (d, J=1.87 Hz, 1H), 5.58 (dd, J=1.87, 8.69 Hz, 1H), 7.08 (t, J=7.96 Hz, 1H), 6.42–6.39 (m, 3H), 3.69 (s, 3H).

Example 33
7-Chloro-4-hydroxy-2-(3-methoxyphenyl)-1,2,5,10-tetrahydropyridazino[4,5-b]quinoline-1,10-dione.

The filtrate set aside and saved from Example 32 was diluted with water/ice (1.0 L) to give a brown suspension which was stirred for 16 hours. The suspension was filtered and the collected solids were washed with water and then ether to give the title compound (1.04 g, 56%) as a tan powder, mp 312–315° C.; MS(CI): 370 (M+H).

Analysis for C18H12ClN3O4. 0.20 H2O. 0.10CH3SO3H: Calculated: C, 56.80; H, 3.37; N, 10.97 Found: C, 56.90; H, 3.55; N, 10.93 1H NMR 8.17 (d, J=8.64 Hz, 1H), 8.06 (d, J=1.71 Hz, 1H), 7.43 (dd, J=1.71, 8.64 Hz, 1H), 7.36 (t, J=8.49, 1H), 7.15–7.12 (m, 2H), 6.93 (d, J=8.49 Hz, 1H), 3.79 (s, 3H).

Example 34
7-Chloro-4-hydroxy-2-(3-hydroxyphenyl)-1,2,5,10-tetrahydropyridazino [4,5-b]quinoline-1,10-dione.

A solution of 7-chloro-4-hydroxy-2-(3-methoxyphenyl)-1,2,5,10-tetrahydropyridazino[4,5-b]quinoline-1,10-dione (0.600 g, 1.62 mM) in methanesulfonic acid (12 mL) was heated to 130–140° C. for 3.5 hours and cooled to room temperature. The brown solution was diluted with water (36 mL) which caused an exotherm and a precipitate formed to give a brown suspension. This suspension was filtered and the collected solids were washed with water (50 mL) and ether to give a brown solid (0.447 g). This material was suspended in water (26 mL) and choline hydroxide solution (45 wt % in methanol, 1.5 mL) was added to give a brown solution. This solution was warmed to 50° C. for 3 hours and cooled to room temperature. Hydrochloric acid (10 mL, 1N) was added to give a brown suspension which was filtered. The collected solids were washed with water and then ether to give a brown powder (0.302 g). This brown powder was suspended in methanol and the resulting suspension concentrated to leave a brown solid. The solid was suspended in methanol and concentrated two additional times to give the title compound (0.260 g, 45%) as a brown powder; mp 333° C. (dec.); MS (CI): 356 (M+H).

Analysis for C17H10ClN3O4. 1.0 H2O. 1.40HCl: Calculated: C, 48.1; H, 3.18; N, 9.89 Found: C, 48.5; H, 3.16; N, 9.45 1H NMR 9.6 (br s, 1H, exchangeable), 8.15 (br s, 1 H), 8.06 (br s, 1H), 7.46 (br s, 1H), 7.23 (br s, 1H), 6.95 (br s, 1H), 6.75 (br s, 1H).

Example 35
7-Chloro-4-hydroxy-2-(4-trifluoromethoxyphenyl)-1,2,5,10-tetrahydropyridazino[4,5-b]quinoline-1,10-dione.

To a stirred suspension of 3-carbomethoxy-7-chloro-4-hydroxyquinoline-2-carboxylic acid N-2-(4-trifluoromethoxyphenyl) hydrazide (600 mg, 1.3 mM) in methanol (85 mL) at ambient temperature was added methanesulfonic acid (3 mL). The reaction mixture was heated to reflux for 68 hours during which time a slight precipitate formed. The solid was removed by filtration. Water (150 mL) was added to the filtrate to produce a light suspension which was isolated via vacuum filtration and dried over phosphorous pentoxide to provide the title compound (467 mg, 84%) as a peach colored solid, mp 320–322° C.; MS (CI): 424 (M+H).

Analysis for C18H9N3O4F3Cl. 0.8 H2O: Calculated: C, 49.34; H, 2.44; N, 9.59 Found: C, 49.01; H, 2.10; N, 9.55 1H NMR 12.90 (s,1H, exchangeable), 12.07 (br s, 1H, exchangeable), 8.16 (d, J=8.64 Hz, 1H), 8.06 (s, 1H), 7.71 (d, 2H, J=8.82), 7.45–7.50 (m, 3H).

The starting material, 3-carbomethoxy-7-chloro-4-hydroxyquinoline-2-carboxylic acid N-2-(4-trifluoromethoxyphenyl)hydrazide, was prepared in the following manner:

a. 3-Carbomethoxy-7-chloro-4-hydroxyquinoline-2-carboxylic acid.

To a stirred suspension of dimethyl-7-chloro-4-hydroxyquinoline-2,3-dicarboxylate (1.0 g, 3.38 mM) in water (20 mL) was added an aqueous solution of sodium hydroxide (0.27 g, 6.75 mM). Upon addition, the suspension dissolved. The reaction mixture was warmed to 60° C. for 1 hour. After this time the reaction was cooled to room temperature and acidified with concentrated hydrochloric acid. The product was then extracted into diethyl ether and ethyl acetate. The organic extracts were dried over magnesium sulfate, filtered and concentrated in vacuo to provide the title compound as a crude solid (900 mg). This material was purified by recrystallization employing an ethyl acetate/hexane co-solvent system to provide the title compound (571 mg, 60%) as a white solid mp 296° C. (dec); MS (CI)=238 (M+H).

Analysis for C12H8NO5Cl. 0.45 CH3CO2CH2CH3. 0.10 H2O: Calculated: C, 51.30; H, 3.68; N 4.34 Found: C, 51.28; H, 3.62; N 3.97 1H NMR 8.22 (d, J=8.7 Hz, 1H), 7.92 (d, J=1.8 Hz, 1H), 7.28 (dd, J=8.7, 1.8 Hz, 1H), 3.90 (s, 3H).

b. 3-Carbomethoxy-7-chloro-4-hydroxy quinoline-2-carboxylic acid N-2-(4-trifluoromethoxyphenyl) hydrazide.

The free base of 4-(trifluoromethoxy)phenylhydrazine was prepared from the hydrochloride salt by treatment of the suspended salt (400 mg, 1.75 mM) in ethyl acetate (50 mL) with 2N sodium hydroxide (50 mL). The organic layer was separated, dried over magnesium sulfate and concentrated in vacuo to provide the free base of 4-(trifluoromethoxy) phenylhydrazine (325 mg, 1.69 mM). This material was placed into anhydrous tetrahydrofuran (5 mL) and cooled to 0° C. under a nitrogen atmosphere.

Concurrently, 3-carbomethoxy-7-chloro-4-hydroxyquinoline-2-carbonyl chloride was prepared from 3-carbomethoxy-7-chloro-4-hydroxyquinoline-2-carboxylic acid (121 mg, 0.43 mM) by heating to 60° C. in thionyl chloride (4 mL). After 3 hours the crude acid chloride was isolated by distilling away the excess thionyl chloride. The crude 3-carbomethoxy-7-chloro-4-hydroxyquinoline-2-carbonyl chloride (130 mg, 0.43 mM) was then placed in anhydrous tetrahydrofuran (3 mL) at ambient temperature and added via cannula to the 4-(trifluoromethoxy) phenylhydrazine solution. After 30 minutes the reaction mixture was poured into 1.0N hydrochloric acid producing a precipitate. The solid was isolated to yield the title compound (185 mg, 95%) as an off-white solid, mp 346–350° C.; MS 456 (M+H). 1H NMR 12.67 (s, 1H, exchangeable), 10.79 (s, 1H, exchangeable), 8.37 (br s, 1H, exchangeable), 8.13 (d, J=8.61 Hz, 1H), 7.83 (d, J=1.76 Hz, 1H), 7.48 (dd, J=8.61, 1.76 Hz, 1H), 7.21 (d, J=8.50 Hz, 2H), 6.94 (d, J=8.50 Hz, 2H), 3.70 (s, 3H).

Example 36

7-Chloro-3-(3-chloro-4-methoxyphenyl)-1-hydroxy-3,4,5, 10-tetrahydropyridazino[4,5-b]quinoline-4,10-dione.

A stirred solution of 3-carbomethoxy-7-chloro-4-hydroxy-quinoline-2-carboxylic acid N-2-(3-chloro-4-methoxyphenyl)hydrazide (2.25 g, 5.16 mM) in methanol (1.13 L) and methanesulfonic acid (113 mL) was refluxed for 1 hour during which time a brown precipitate formed. This suspension was cooled to room temperature, stirred for 16 hours and filtered (the filtrate was saved for use in Example 37). The collected solids were washed with methanol and then ether to give the title compound (0.153 g, 7%) as a yellow powder, mp 395–396° C.; MS(CI): 404 (M+H).

Analysis for C18H11Cl2N3O4. 1.20 H2O: Calculated: C, 50.77; H, 3.17; N, 9.87 Found: C, 50.33; H, 2.87; N, 9.61 1H NMR 13.36 (s, 1H, exchangeable), 12.50 (s, 1H, exchangeable), 8.28 (d, J=8.78 Hz, 1H), 8.22 (d, J=1.74 Hz, 1H), 7.77 (d, J=2.42 Hz, 1H), 7.67 (dd, J=2.42, 8.91 Hz, 1H), 7.62 (dd, J=1.74, 8.78 Hz, 1H), 7.30 (d, J=8.91 Hz, 1H), 3.94 (s, 3H).

The starting material, 3-carbomethoxy-7-chloro-4-hydroxyquinoline-2-carboxylic acid N-2-(3-chloro-4-methoxyphenyl)hydrazide, was prepared in the following manner:

a. 3-Chloro-4-methoxyphenylhydrazine

A solution of 3-chloro-p-anisidine hydrochloride (10 g, 52 mM) in hydrochloric acid (48 mL, 12N) was cooled to −10° C. A solution of sodium nitrite (3.56 g, 52 mM) in water (19.5 mL) was slowly added to the reaction such that the temperature did not exceed −5° C. The reaction mixture was then stirred for 1 hour at 0° C. The resulting diazonium salt solution was then added to a cold (0° C., ice bath) solution of tin chloride dihydrate (44 g, 193 mM) in hydrochloric acid (29 mL, 12N) at a rate such that the temperature did not exceed 5° C. A purple foamy suspension was formed and, after adding water (20 mL), the mixture was stirred for 3 hours at 0° C. The purple solids were filtered, washed with ethyl acetate and then added to aqueous sodium bicarbonate solution. The resulting mixture was partitioned with ethyl acetate and the entire mixture filtered to separate insoluble tin salts. The collected tin salts were washed with water and ethyl acetate. The ethyl acetate layer from the initial filtration and the ethyl acetate from the washes of the tin salts were combined, dried over magnesium sulfate and concentrated to provide the title compound (4.49 g, 51%) as a brown solid; MS(CI): 172 (M-1) 1H NMR 6.94–6.90 (m, 2H), 6.71 (dd, J=2.70, 9.00 Hz, 1H), 3.73 (s, 3H).

b. 3-Carbomethoxy-7-chloro-4-hydroxyquinoline-2-carboxylic acid N-2-(3-chloro-4-methoxyphenyl) hydrazide.

To a solution of 3-chloro-4-methoxyphenylhydrazine (4.26 g, 24.7 mM) in 35b.) in tetrahydrofuran (200 mL) was added a solution of 3-carbomethoxy-7-chloro-4-hydroxyquinoline-2-carbonyl chloride (3.54 g, 11.8 mM, as prepared in Example 35b.) in tetrahydrofuran (100 mL) at 0° C. The resulting yellow suspension was stirred at 0° C. for 30 minutes and diluted with water (200 mL) to give a yellow solution. This solution was further diluted with hydrochloric acid (600 mL, 1N) to give a tan suspension which was stirred for 1 hour. The suspension was filtered (the filtrate was saved) and the collected solids were washed with water and then ether to give the title compound (2.30 g, 45%) as a tan powder, MS(CI): 436 (M+H), which was used above in the synthesis described for 7-chloro-3-(3-chloro-4-methoxyphenyl)-1-hydroxy-3,4,5,10-tetrahydropyridazino [4,5-b]quinoline-4,10-dione. 1H NMR 12.69 (s, 1H, exchangeable), 10.72 (s, 1H, exchangeable), 8.14 (d, J=8.50 Hz, 1H), 8.00 (br s, 1H, exchangeable), 7.76 (s, 1H), 7.48 (d, J=8.50 Hz, 1H), 7.05 (d, J=8.80 Hz, 1H), 6.98 (d, J=2.28 Hz, 1H), 6.85 (dd, J=2.28, 8.80 Hz, 1H), 3.78 (s, 3H), 3.70 (s, 3H). After sitting for five days, further precipitation occurred in the above saved acidic filtrate. The solids were collected to provide material (1.80 g) consisting of a mixture of the title compound (60%), 7-chloro-2-(3-chloro-4-methoxyphenyl)-1-hydroxy-1,2,5,10-tetrahydropyridazino [4,5-b]quinoline-1,10-dione (35%) and 7-chloro-3-(3-chloro-4-methoxyphenyl)-1-hydroxy-3,4,5,10-tetrahydropyridazino[4,5-b]quinoline-4,10-dione (5%).

Example 37

7-Chloro-2-(3-chloro-4-methoxyphenyl)-4-hydroxy-1,2,5, 10-tetrahydropyridazino[4,5-b]quinoline-1,10-dione.

The filtrate saved from Example 36 was concentrated to approximately 500 mL and diluted with water/ice (1.1 L) to give a light green suspension which was stirred for 3 hours. The suspension was filtered and the collected solids were resuspended in water (500 mL) and stirred for 16 hours. This suspension was filtered and the collected solids were washed successively with water, acetonitrile/ether and then ether to give the title compound (1.42 g, 68%) as a green powder, mp 348–351° C.; MS(CI): 404 (M+H).

Analysis for C18H11C12N3O4. 1.20 H2O. 0.50 CH3SO3H: Calculated: C, 46.89; H, 3.27; N, 8.87 Found: C, 46.54; H, 2.96; N, 8.91 1H NMR 12.82 (br s, 1H, exchangeable), 12.05 (br s, 1H, exchangeable), 8.16 (d, J=9.01 Hz, 1H), 8.06 (d, J=1.56 Hz, 1H), 7.64 (d, J=2.37 Hz, 1H), 7.52 (dd, J=2.37, 8.89 Hz, 1H), 7.45 (dd, J=1.56, 9.01 Hz, 1H), 7.23 (d, J=8.89 Hz, 1H), 3.91 (s, 3H).

Example 38

7-Chloro-2-(2-methoxypyrid-5-yl)-4-hydroxy-1,2,5,10-tetrahydropyridazino[4,5-b]quinoline-1,10-dione.

To a cold (ice bath) stirred solution of 5-hydrazino-2-methoxypyridine (0.839 g, 6.03 mM) in anhydrous THF (40 mL) was added dropwise a solution of 3-carbomethoxy-7-chloro-4-hydroxyquinoline-2-carbonyl chloride (1.67 g, 5.59 mM) in THF (40 mL). After stirring at 0° C. for 3 hr, the reaction mixture was allowed to warm to room temperature and stirred an additional 17 hr. The reaction mixture was diluted with water/ethyl acetate (30 mL/40 mL) and the pH of the resulting mixture adjusted to 4 by adding 2N sodium hydroxide. The resulting mixture was filtered and the collected orange solid was then triturated in warm methanol (10 mL) and filtered to separate the title compound (0.17 g, 5.7%) as a brown solid, mp 235–237° C. (dec); MS(CI): 371 (M+H).

Analysis for $C_{17}H_{11}ClN_4O_4 \cdot 1.45 H_2O$ Calculated: C, 51.45; H, 3.53; N, 14.12 Found: C, 51.26; H, 2.95; N, 14.18 1H NMR 12.88 (br s, 1H, exchangeable), 12.09 (br s, 1H, exchangeable), 8.34 (d, J=2.24 Hz, 1H), 8.16 (d, J=7.6 Hz, 1H), 8.05 (s, 1H), 7.85 (dd, J=8.7, 2.24 Hz, 1H), 7.46 (d, J=7.6 Hz, 1H), 6.93 (d, J=8.7 Hz, 1H), 3.88 (s, 3H).

The starting materials, 3-carbomethoxy-7-chloro-4-hydroxyquinoline-2-carbonyl chloride and 5-hydrazino-2-methoxypyridine, were prepared in the following manner:

a. 3-Carbomethoxy-7-chloro-4-hydroxyquinoline-2-carbonyl chloride.

After refluxing a mixture of 3-carbomethoxy-7-chloro-4-hydroxyquinoline-2-carboxylic acid (1.56 g, 5.6 mM) and thionyl chloride (5 mL, 68.5 mM) in methylene chloride (12 mL) for 2 hr, the resulting cloudy solution was concentrated to leave a solid. This residue was diluted with THF and re-concentrated to leave a solid which was again treated with THF and concentrated to leave the crude title compound (1.67 g, 100%) as a cream colored solid.

b. 5-Hydrazino-2-methoxypyridine.

To a stirred cold (−10° C.) solution of 5-amino-2-methoxypyridine (5.01 g, 40.4 mM) in concentrated hydrochloric acid (50 mL) was added dropwise a solution of sodium nitrite (2.9 g, 42 mM) in water (10 mL). After stirring at −10° C. for 10 min, the reaction mixture was added in portions to a cold (−20° C.) stirred solution of stannous chloride dihydrate (22.9 g, 101 mM) in concentrated hydrochloric acid (15 mL). The resulting thick mixture was diluted with water (10 mL) and concentrated hydrochloric acid (15 mL) and stirring at −10° C. was continued for an additional 1 hr. The mixture was then filtered and the collected solids washed with ether (three 40 mL portions) and dried in vacuo to afford the crude hydrochloride salt (7.03 g, 125%) of the title compound as a pink solid. A portion (3.97 g, ca. 22 mM) of this material was suspended in ethyl acetate/ether (75 mL/25 mL) and 2N sodium hydroxide was added to the resulting stirred suspension until the pH reached 6.5. After stirring for 15 min, the organic phase was separated and the aqueous phase was extracted twice with 50 mL portions of ethyl acetate/ether (1:1). The organic phases were combined, dried (MgSO$_4$), filtered and concentrated to leave the title compound (0.839 g, 27%) as a crude solid which was used without further purification.

Example 39

7-Chloro-4-hydroxy-2-(4-methoxy-2-methylphenyl)-1,2,5,10-tetrahydropyridazino[4,5-b]quinoline-1,10-dione.

To a stirred suspension of 7-chloro-3-methoxycarbonyl-4-oxo-1,4-dihydro-quinoline-2-carboxylic acid N-2-(4-methoxy-2-methylphenyl)hydrazide (3.0 g, 7.2 mM) and the solids (0.6 g, 1.6 mM) of a mixture consisting of 7-chloro-4-hydroxy-2-(4-methoxy-2-methylphenyl)-1,2,5,10-tetrahydropyridazino[4,5-b]quinoline-1,10-dione and 6-chloro-2-(4-methoxy-2-methylanilino)-2,3,4,9-tetrahydro-1H-pyrrolo- [3,4-b]quinoline-1,3,9-trione) collected from the concentrated filtrate described in Example 1a, in methanol (500 mL) was added methanesulfonic acid (50 mL) and the resulting amber suspension was refluxed for 7 hr. The resulting solution was stirred at room temperature overnight and then diluted with ~600 mL of ice/water to give a tan suspension. After stirring for 2 hr, the suspension was filtered to give a solid (2.8 g, 100%). Recrystallization of this material from boiling methanol (500 mL) gave the title compound as a white powder (1.7 g, 61%), mp 354–356° C.

Analysis for $C_{19}H_{14}ClN_3O_4 \cdot 1.5 H_2O \cdot 0.2 CH_3OH \cdot 0.2 (C_2H_5)_2O$: Calculated: C, 55.60; H, 4.62; N, 9.73 Found: C, 55.25; H, 4.35; N, 9.60 H NMR (DMSO-d6): 12.74 (br s, 1H, exchangeable), 12.00 (br s, 1H, exchangeable), 8.16 (d, J=8.8 Hz, 1H), 8.06 (s, 1H), 7.46 (d, J=8.8 Hz, 1H), 7.21 (d, J=8.6 Hz, 1H), 6.91 (s, 1H), 6.85 (d, J=8.6 Hz, 1H), 3.79 (s, 3H), 2.08 (s, 3H).

The starting material, 7-chloro-3-methoxycarbonyl-4-oxo-1,4-dihydroquinoline-2-carboxylic acid N-2-(4-methoxy-2-methylphenyl)hydrazide, was prepared in the following manner:

a) 7-Chloro-3-methoxycarbonyl-4-oxo-1,4-dihydroquinoline-2-carboxylic acid N-2-(4-methoxy-2-methylphenyl)hydrazide.

4-Methoxy-2-methylphenylhydrazine hydrochloride (4.7 g, 25 mM) was partitioned between diethyl ether (300 mL) and 2N sodium hydroxide (50 mL). The ether layer was separated and the aqueous layer was extracted with an additional portion of ether (300 mL). The combined ether extracts were dried (Na$_2$SO$_4$), filtered and concentrated to leave the free hydrazine as a yellow powder. This hydrazine was dissolved in anhydrous tetrahydrofuran (180 mL). After cooling the resulting amber solution to 0° C., a solution of 7-chloro-3-methoxycarbonyl-4-oxo-1,4-dihydroquinoline-2-carbonyl chloride (3.0 g, 10.0 mM) in THF (90 mL) was added dropwise over 15 minutes. When the addition was completed, the resulting yellow suspension was stirred at 0° C. for 30 minutes and then at room temperature for 2 hr. The reaction mixture was quenched by adding ~200 g of water/ice followed by 500 mL of cold 1N hydrochloric acid. The resulting yellow suspension was stirred for 1 hr and the yellow solids were collected via filtration, washed with water and then ether and air dried to provide the title compound as a white powder (3.3 g, 79%). The filtrate was partially concentrated to remove most of the THF and the resulting suspension was filtered to provide an additional ~0.6 g of solids consisting (HPLC analysis) of 35% of 7-chloro-4-hydroxy-2-(4-methoxy-2-methylphenyl)-1,2,5,10-tetrahydropyridazino[4,5-b]quinoline-1,10-dione and 65% of 6-chloro-2-(4-methoxy-2-methylanilino)-2,3,4,9-tetrahydro-1H-pyrrolo-[3,4-b]quinoline-1,3,9-trione.

The 7-chloro-3-methoxycarbonyl-4-oxo-1,4-dihydroquinoline-2-carbonyl chloride used in Example 39a was prepared in the following manner:

b) 7-Chloro-3-methoxycarbonyl-4-oxo-1,4-dihydroquinoline-2-carbonyl chloride.

To a stirred suspension of 7-chloro-3-methoxycarbonyl-4-oxo-1,4-dihydroquinoline-2-carboxylic acid (prepared from the diester) (35.0 g, 0.124M) in alcohol free chloroform (850 mL) under nitrogen was added thionyl chloride (60.3 g, 37 mL, 0.507M) in one portion. The resulting mixture was refluxed until solution occurred (1.5 hr). After cooling to room temperature, the solution was concentrated using a rotary evaporator (bath temperature=25° C.) to give a tan solid. This material was dried in vacuo at room temperature for two days to provide the title acid chloride (34.7 g, 93.2%) as a tan solid.

The 2-methyl-4-methoxyphenylhydrazine hydrochloride used in Example 39a was prepared in the following manner:

c) 2-Methyl-4-methoxyphenylhydrazine hydrochloride.

A solution of sodium nitrate (5.60 g, 81.2 mM) in water (56 mL) was added in the course of 20 minutes to a mechanically stirred suspension of 2-methyl-4-methoxyaniline (10.42 mL, 81.0 mM) in a mixture of 12N HCl (60 mL) and water (64 mL) maintained at −5° C. The dark solution was cooled to −15° C. over 15 minutes and a solution of $SnCl_2.2H_2O$ (53.3 g, 236.2 mM) in 12N HCl (36 mL) was added over 30 minutes, the temperature being maintained between −15 and −10° C. The pink suspension was stirred at −15° C. for 30 minutes and ethanol (25 mL) was added dropwise. The suspension was stirred at −15° C. for 3 hours and filtered under N2(g). The filtration was done at −10° C. jacketed funnel) and took 2 hours. The cake was sucked dry and washed with 50% ethanol/ether (200 mL) and ether (500 mL). The solid was dried under a N2(g) stream for 20 hours to give the hydrochloride salt of the title compound (8.60 g, 56%) as a grey powder, mp 107° C. (decomp.); MS(CI): 152 (M+H).

Analysis for C8H12N2O. HCl. H2O: Calculated: C, 46.49; H, 7.32; N, 13.55 Found: C, 46.46; H, 6.92; N, 13.300. MHz 1H NMR (DMSO-d6): 10.01 (s, 3H, exchangeable), 7.48 (br s, 1H, exchangeable), 6.94 (d, J=8.8 Hz, 1H), 6.77–6.74 (m, 2H), 3.70 (s, 3H), 2.19 (s, 3H).

Example 39(2)

An alternate synthesis of 7-chloro-3-methoxycarbonyl-4-oxo-1,4-dihydroquinoline-2-carboxylic acid N-2-(4-methoxy-2-methylphenyl)hydrazide.

4-Methoxy-2-methylphenylhydrazine hydrochloride (11.38 g, 60.32 mM) was suspended in dry tetrahydrofuran (264 mL) under argon and treated with 2,6-lutidine (14.06 mL, 120.6 mM). This reaction mixture was cooled in an ice bath and a solution of 7-chloro-3-methoxycarbonyl-4-oxo-1,4-dihydroquinoline-2-carbonyl chloride (18.14 g, 60.32 mM) in THF (328 mL) was added at a rate to maintain the reaction temperature at 2–50° C. After the addition was completed, the reaction mixture was stirred 25 minutes at 0–20° C. and then added with stirring to ice cold 1.0N HCl (1300 mL). Stirring was continued for several hours until the mixture became a free flowing suspension. The solids were filtered off, washed with water and air dried to give the title compound (17.57 g, 70%) as a tan solid which was cyclized to title compound (39) using standard conditions. Note: 2,6-di-tert-butylpyridine may be used in place of 2,6-lutidine (2,6-dimethylpyridine) in the above procedure.

Example 40

7-Chloro-4-hydroxy-2-(4-methoxy-2-methylphenyl)-1,2,5,10-tetrahydropyridazino[4,5-b]quinoline-1,10-dione N-methylglucamine salt.

7-Chloro-4-hydroxy-2-(4-methoxy-2-methylphenyl)-1,2,5,10-tetrahydropyridazino[4,5-b]quinoline-1,10-dione (0.45 g, 1.17 mM) was stirred in methanol (20 mL) and N-Methyl-D-Glucamine (0.23 g, 1.17 mM) was added to give a clear yellow solution. This solution was concentrated and the residue was dissolved in water (20 mL) to give a yellow solution. This solution was filtered through a Gellman 0.45 μm Acrodisc and concentrated to give a yellow residue. The residue was triturated with 2-propanol (20 mL) to give a yellow suspension. The solids were collected and washed with 2-propanol to give the title compound (0.20 g, 29%) as a yellow powder, mp 177° C. (decomp.).

Analysis for C19H14ClN3O4. C7H18NO5. 1.5 H2O: Calculated: C, 51.53; H, 5.65; N, 9.24 Found: C, 51.17; H, 5.28; N, 8.88 300 MHz 1H NMR (DMSO-d6): 8.14 (s, 1H), 8.10 (d, J=8.6 Hz, 1H), 7.33 (d, J=8.6 Hz, 1H), 7.06 (d, J=8.0 Hz, 1H), 6.76 (br m, 2H), 3.84 (m, 1H), 3.76 (s, 3H), 3.65–3.56 (m, 2H), 3.48–3.38 (m, 3H), 2.95–2.87 (m, 2H), 2.51–2.46 (m, 3H), 2.02 (s, 3H).

Example 41

7-Chloro-3-(4-chloro-2-methylphenyl)-1-hydroxy-3,4,5,10-tetrahydropyridazino [4,5-b]quinoline-4,10-dione.

7-Chloro-3-methoxycarbonyl-4-oxo-1,4-dihydroquinoline-2-carboxylic acid N-2-(4-chloro-2-methylphenyl)hydrazide (2.00 g, 4.76 mM) was suspended in methanol (1.0 L) and methanesulfonic acid (100 mL) was added at a fast dropwise rate with good stirring. The resulting yellow suspension was refluxed for four days to give an orange solution. Methanol (500 mL) was distilled off and the concentrated solution was cooled to room temperature to give a yellow suspension. This suspension was filtered (the filtrate was saved for use in Example 42). The collected solids were washed with methanol and ether to give the title compound (0.72 g, 39%) as a yellow powder, mp 336–339° C.; MS(CI): 388 (M+H).

Analysis for C18H11Cl2N3O3. 1.15 H2O: Calculated: C, 52.87; H, 3.27; N, 10.28 Found: C, 52.5 1; H, 2.87; N, 10.12 300 MHz 1H NMR (DMSO-d6): 13.40 (s, 1H, exchangeable), 12.55 (s, 1H, exchangeable), 8.30 (d, J=8.8 Hz, 1H), 8.20 (s, 1H), 7.62 (d, J=8.8 Hz, 1H), 7.53 (s, 1H), 7.43 (s, 2H), 2.16 (s, 3H).

Example 42

7-Chloro-2-(4-chloro-2-methylphenyl)-4-hydroxy-1,2,5,10-tetrahydropyridazino[4,5-b]quinoline-1,10-dione.

The saved filtrate from Example 41. was diluted with water (1.0 L) and the resulting suspension was stirred for 2 hours. The solids were collected and washed with water and then ether to give the title compound (0.54 g, 29%) as an off-white powder, mp 355–357° C.; MS(CI): 388 (M+H).

Analysis for C18H11Cl2N3O3. 0.20 H2O: Calculated: C, 55.18; H, 2.93; N, 10.72 Found: C, 55.00; H, 2.62; N, 10.66 300 MHz 1H NMR (DMSO-d6): 12.84 (br s, 1H, exchangeable), 12.07 (br s, 1H, exchangeable), 8.16 (d, J=8.6 Hz, 1H), 8.07 (s, 1H), 7.47–7.33 (m, 4H), 2.12 (s, 3H).

Example 42a

Alternatively, the title compound was prepared by the following procedure described generally in Scheme 6 and similar conditions to that described in Example 82 wherein to a stirred suspension of 2-pyrrolidinocarbamide-7-chloro-4-hydroxy quinoline 3-carboxylic acid in THF was added DCC. A THF solution of N-t-butoxy-carbonyl-N'-4-chloro-2-methylphenylhydrazine was immediately added to the above suspension. The reaction mixture was stirred at room temperature for 4 hours. Upon completion of the coupling (after monitoring by an appropriate chromatographic method—e.g. TLC or HPLC) the byproduct urea was removed via vacuum filtration. Partial purification by flash chromatography employing 5% methanol/$CH_2Cl_2$ yielded the desired hydrazide. To the hydrazide suspended in THF was added methanesulfonic acid. The reaction was stirred at room temperature for 24 hours and then poured into ice water. The resulting precipitate was isolated, dried and triturated/sonicated with methanol and isolated to yield the title compound.

The starting material, 2-pyrrolidinocarbamide-7-chloro-4-hydroxyquinoline-3-carboxylic acid, and related starting materials were prepared according to the procedures described for example 82a and b herein.

The starting material, N-t-butoxycarbonyl-N1-4-chloro-2-methylphenylhydrazine, was prepared in the following manner:

To a suspension of 4-chloro-2-methyl-phenylhydrazine (992 mg, 6.33 mM) and potassium carbonate (1.44 g, 10.4 mM) in saturated aqueous sodium bicarbonate solution (12 mL) was added a solution of di-t-butyl dicarbonate (1.52 g, 6.96 mM) in THF (24 mL). After 2.5 hours, the mixture was partitioned between diethyl ether and the aqueous layer. The organic extracts were combined and washed with water and brine, dried (MgSO$_4$), filtered and concentrated in vacuo. The crude material was purified by flash column chromatography with 25% diethylether-hexane as eluant yielding the title compound (1.56 g, 96%) as a tan solid, MS(CI): 256,(M). 300MH2H NMR (DMSO-d6); 8.81(br S, 1H), 7.17(br S, 1H), 7.00–7.08(m, 2H), 6.55–6.62(m, 1H), 2.09(s, 3H), 1.41(s,9H).

Example 43
7-Chloro-2-(2,4-dimethylphenyl)-4-hydroxy-1,2,5,10-tetrahydropyridazino[4,5-b]quinoline-1,10-dione.

7-Chloro-3-methoxycarbonyl-4-oxo-1,4-dihydroquinoline-2-carboxylic acid N-2-(2,4-dimethylphenyl)hydrazide (3.80 g, 9.50 mM) was suspended in methanol (330 mL) and methanesulfonic acid (83 mL) was added at a fast dropwise rate with good stirring. The resulting orange suspension was refluxed for 20 hours to give an amber solution. This solution was cooled to room temperature and water (75 mL) was added dropwise to give a yellow suspension which was stirred for 2 hours. The solids were filtered off and the filtrate was diluted with water (300 mL) to give a yellow suspension which was stirred for 20 hours. The solids were collected and washed with water, methanol/ether, then ether to give the crude title compound (1.80 g). Recrystallization from methanol gave the title compound (0.58 g, 17%) as a tan powder, mp 349–351° C.; MS(CI): 368 (M+H).

Analysis for C19H14ClN3O3. H2O. 0.5 CH3OH: Calculated: C, 56.25; H, 4.34; N, 10.06 Found: C, 56.01; H, 4.36; N, 9.90 300 MHz 1H NMR (DMSO-d6): 12.72 (br s, 1H, exchangeable), 12.02 (br s, 1H, exchangeable), 8.16 (d, J=8.7 Hz, 1H), 8.06 (s, 1H), 7.46 (d, J=8.7 Hz, 1H), 7.18 (m, 3H), 2.33 (s, 3H), 2.07 (s, 3H).

The starting material, hydrazide, was prepared from the corresponding acid chloride which was prepared from the corresponding diester.

Example 43a
Alternatively, the title compound was prepared according to the general procedure described in 42a except using the appropriate N-t-butoxy-carbonyl-N'-2,4-dimethyl-phenylhydrazine which was prepared as described in 42a except 2,4-dimethyl-phenylhydrazine was reacted with di-t-butyldicarbonate.

Example 44
7-Chloro-2-(3,4-dihydroxyphenyl)-4-hydroxy-1,2,5,10-tetrahydropyridazino[4,5-b]quinoline-1,10-dione.

7-Chloro-4-hydroxy-2-(3,4-dimethoxyphenyl)-1,2,5,10-tetrahydropyridazino[4,5-b]quinoline-1,10-dione (1.00 g, 2.50 mM) was refluxed in 48% HBr (40 mL) for 6 hours to give an orange suspension. Heat was removed and the suspension was filtered while still warm. The collected solids were washed with water and then ether to give the crude product (0.94 g) as a yellow powder. This material was recrystallized from refluxing methanol (600 mL) to give the title compound (0.63 g, 68%) as a yellow powder, mp 269–272° C.; MS(CI): 372 (M+H).

Analysis for C17H10ClN3O5. 0.5 H2O. 0.75 CH3OH: Calculated: C, 52.67; H, 3.49; N, 10.38 Found: C, 52.66; H, 3.64; N, 10.14 300 MHz 1H NMR (DMSO-d6): 12.67 (br s, 1H, exchangeable), 11.97 (br s, 1H, exchangeable), 9.19 (br s, 1H, exchangeable), 9.10 (br s, 1H, exchangeable), 8.15 (d, J=8.3 Hz, 1H), 8.04 (s, 1H), 7.44 (d, J=8.3 Hz, 1H), 6.89–6.73 (m, 3H).

The starting material, 7-chloro-4-hydroxy-2-(3,4-dimethoxyphenyl)-1,2,5,10-tetrahydropyridazino[4,5-b]quinoline-1,10-dione, was prepared as described in Example 45.

Example 45
7-Chloro-4-hydroxy-2-(3,4-dimethoxyphenyl)-1,2,5,10-tetrahydropyridazino[4,5-b]quinoline-1,10-dione.

7-Chloro-3-methoxycarbonyl-4-oxo-1,4-dihydroquinoline-2-carbonyl chloride (7.00 g, 23.3 mM) was dissolved in tetrahydrofuran (210 mL) and added dropwise over 20 minutes to a cold (0° C.) solution of 3,4-dimethoxyphenylhydrazine (9.80 g, 58.3 mM) in tetrahydrofuran (420 mL) with stirring. The resulting brown suspension was stirred at 0° C. for 30 minutes and at room temperature for 2 hours. Ice/water slurry (450 mL) was added to the reaction mixture followed by 1N HCl (1.2 L) and the brown suspension was stirred for 1 hour. The solids were separated by filtration and washed with water and then ether to provide 7-chloro-3-methoxycarbonyl-4-oxo-1,4-dihydroquinoline-2-carboxylic acid N-2-(2,4-dimethoxyphenyl)hydrazide (15 g, wet). The combined filtrate and washes were partially concentrated to remove the THF whereupon a precipitate formed. This precipitate was collected and washed with water and then ether to give the crude title compound (2.00 g). Recrystallization of this crude from refluxing methanol (500 mL) gave the title compound (0.98 g, 10%) as a tan powder, mp 334–336° C.; MS(CI): 400 (M+H).

Analysis for C19H14ClN3O5. CH3OH: Calculated: C, 55.63; H, 4.20; N, 9.73 Found: C, 55.27; H, 4.31; N, 9.56 300 MHz 1H NMR (DMSO-d6): 12.75 (s, 1H, exchangeable), 12.01 (s, 1H, exchangeable), 8.16 (d, J=8.6 Hz, 1H), 8.05 (s, 1H), 7.45 (d, J=8.6 Hz, 1H), 7.13 (S, 1H), 7.03 (S, 2H), 3.80 (S, 3H), 3.76 (S, 3H).

Example 46
7-Chloro-4-hydroxy-2-(2-methylthioethyl)-1,2,5,10-tetrahydropyridazino[4,5-b]quinoline-1,10-dione.

To a suspension of sodium thiomethoxide (230 mg, 3.2 mM) in dimethylformamide (20 mL), was added in one portion 2-(2-bromoethyl)-7-chloro-4-hydroxy-1,2,5,10-tetrahydropyridazino[4,5-b]quinoline-1,10-dione (0.4 g, 1.08 mM) as a dry powder. This mixture was warmed to gentle reflux for about three hours. At this point the heat was removed and the reaction mixture was poured into ice cold 1.2N HCl (100 mL) and stirred about one hour. The resulting precipitate was vacuum filtered and washed with water and ether, then vacuum dried at 50° C. to yield 330 mg (91 %) of the title compound as an off-white powder. mp 275–277° C.; MS: 338(M+1).

Analysis for C14H12ClN3O3S Calculated: C, 49.78; H, 3.58; N, 12.44 Found: C, 49.73; H, 3.73; N, 12.30 NMR: 2.11(s, 3H), 2.79 (t, 2H, J=7.13 Hz), 4.09 (t, 2H, J=7.08 Hz), 7.42(dd, 1H, J=8.59, 1.6 Hz), 8.57(d, 1H, J=1.77 Hz), 8.13(d, 1H, J=8.64 Hz), 11.8 (brs, 1H), 12.64(brs, 1H).

Example 47
7,9-dichloro-2-(2,4-dimethylphenyl)-4-hydroxy-1,2,5,10-tetrahydropyridazino[4,5-b]quinoline-1,10-dione.

To a stirred suspension of 5,7-dichloro-3-methoxycarbonyl-4-oxo-1,4-dihydroquinoline-2-carboxylic acid N-2-(2,4-dimethylphenyl)hydrazide (3.60 g, 8.31 mM) in methanol (151 mL) was slowly added methanesulfonic acid (7.2 mL) and the resulting mixture was heated to reflux. After 2 hr at reflux, the reaction mixture was allowed to cool to room temperature and then filtered to separate the precipitated solids. The filtrate was diluted with water (150 mL)

whereupon a white precipitate formed. This mixture was stirred overnight at room temperature and the solids were collected by filtration, then washed with water and ether and air dried to give the title compound as a white powder (2.78 g, 84%), mp 335–336° C.; MS(CI): 402 (M+H).

Analysis for C19H13Cl2N3O3. 0.2 H2O Calculated: C, 56.25; H, 3.37; N, 10.09 Found: C, 56.23; H, 3.33; N, 10.35 NMR: 12.73 (br s, 1H, exchangeable), 11.92 (br s, 1H, exchangeable), 8.03 (s, 1H), 7.51 (s, 1H), 7.17–7.08 (m, 3H), 2.32 (s, 1H), 2.06 (s, 1H).

The starting material, 5,7-dichloro-3-methoxycarbonyl-4-oxo-1,4-dihydroquinoline-2-carboxylic acid N-2-(2,4-dimethylphenyl)hydrazide, was prepared in the following manner:

a) 3-Carbomethoxy-5,7-dichloro-4-hydroxyquinoline-2-carboxylic acid.

To a stirred suspension of dimethyl-5,7-dichloro-4-hydroxyquinoline-2,3-dicarboxylate (4.0 g, 12.2 mM) in water (72 mL) was added an aqueous solution of sodium hydroxide (0.97 g, 24.2 mM in 22 mL water). The solids immediately dissolved and the resulting solution was heated at 55° C. for 30 min. The reaction mixture was then slowly cooled to 20° C. and acidified by adding 6 N hydrochloric acid (4 mL) while maintaining the temperature below 20° C. A precipitate formed and, after stirring the suspension for 2 hr, the mixture was filtered and the collected solids washed successively with water, ether/methanol, and ether. Air drying provided the title compound (2.82 g, 74%) as a tan solid. An analytical sample of the title compound was obtained by recrystallization of a small portion of the isolated solid from ethyl acetate to provide a tan solid, mp 339–340° C.; MS(CI): 315 (M+H).

Analysis for C12H7Cl2N3O5N Calculated: C, 45.6; H, 2.23; N, 4.43 Found: C, 45.78; H, 2.43; N, 4.52 1H NMR (MeOD): 7.82 (d, J=2.0 Hz, 1H), 7.44 (d, J=2.0 Hz, 1H), 3.8 (s, 3H).

b) 3-Carbomethoxy-5,7-dichloro-4-hydroxyquinoline-2-carbonyl chloride.

Thionyl chloride (1.50 g, 12.6 mM) was added to a stirred suspension of 3-carbomethoxy-5,7-dichloro-4-hydroxyquinoline-2-carboxylic acid (1.0 g, 3.17 mM) in ethanol free chloroform (25 mL). The resulting suspension was refluxed for 5 hr whereupon solution occurred. The reaction mixture was allowed to cool to room temperature and then concentrated to leave the title acid chloride (0.88 g, 83%) as a tan solid. This material was used as is for the formation of acid hydrazides.

c) 5,7-Dichloro-3-methoxycarbonyl-4-oxo-1,4-dihydroquinoline-2-carboxylic acid N-2-(2,4-dimethylphenyl)hydrazide.

3-Carbomethoxy-5,7-dichloro-4-hydroxyquinoline-2-carbonyl chloride (3.65 g, 11.0 mM) was dissolved in tetrahydrofuran (274 mL) and added dropwise to a cooled (0° C.) solution of 2,4-dimethylphenylhydrazine (3.13 g, 23.0 mM) in tetrahydrofuran (172 mL) with stirring. A brown/red suspension slowly formed and the resulting mixture was stirred at 0° C. for 30 min. The reaction was quenched by adding cold water (223 mL) followed by 1N HCl (669 mL). The resulting mixture was stirred for 1 hr and then filtered to separate the precipitated solids. The collected solids were washed with water and then ether to provide, after air drying, the title compound (3.60 g, 76%) as a white powder; MS(CI): 434 (M+H). 1H NMR (DMSO-d6): 12.55 (br s, 1H, exchangeable), 10.67 (br s, 1H, exchangeable), 7.76 (d, J=1.6 Hz, 1H), 7.54 (d, J=1.6 Hz, 1H), 7.19 (br s, exchangeable, 1H), 6.91–6.76 (m, 3H), 3.69 (s, 3H), 2.19 (s, 6H).

Example 48

7-Chloro-4-hydroxy-2-(4-methoxy-2-methylphenyl)-1,2,5,10-tetrahydropyridazino[4,5-b]quinoline-1,10-dione sodium salt.

To a stirred suspension of 7-chloro-4-hydroxy-2-(4-methoxy-2-methylphenyl)-1,2,5,10-tetrahydropyridazino[4,5-b]quinoline-1,10-dione (2.00 g, 5.22 mM) in 0.1N sodium hydroxide (52.2 mL, 5.22 mM) was added water (100 mL) and methanol (3 mL). After brief sonication, the solids dissolved and the resulting solution was filtered through a Gelman Glass Acrodisc frit (0.45 μm) and concentrated to dryness. The residue was triturated with isopropanol (100 mL) and filtered to separate the solids. The solids were washed several times with isopropanol and then dried under vacuum at 100° C. overnight to provide the title compound (1.64 g, 78%) as a yellow powder, mp 356° C.(dec).

Analysis for C19H13ClN3O4. 1.0 Na. 0.02 (CH3) 2CHOH. 1.8 H2O Calculated: C, 52.10; H, 3.84; N, 9.56 Found: C, 52.10; H, 3.71; N, 9.40 1H NMR (DMSO-d6): 8.15–8.17 (m, 2H), 7.31 (dd, J=8.7, 2.0 Hz, 1H), 7.11 (d, J=8.4 Hz, 1H), 6.83–6.76 (m, 2H), 3.76 (s, 3H), 2.07 (s, 3H).

Example 49

7-Chloro-4-hydroxy-2-(4-methoxy-2-methylphenyl)-1,2,5,10-tetrahydropyridazino[4,5-b]quinoline-1,10-dione choline salt.

To a stirred suspension of 7-chloro-4-hydroxy-2-(4-methoxy-2-methylphenyl)-1,2,5,10-tetrahydropyridazino[4,5-b]quinoline-1,10-dione (400 mg, 1.03 mM) in methanol (4 mL) was added choline hydroxide (45% by weight in methanol, 295.6 μL, 1.03 mM). After brief sonication, all solids dissolved and the resulting solution was filtered through a Gelman Glass Acrodisc filter (0.45 μm) along with an additional quantity of methanol (8 mL). The filtrate was concentrated to dryness and the residual oil was stirred with isopropanol (15 mL) and ethanol (8 mL) whereupon crystallization occurred. The solids were collected and dried under vacuum at 100° C. overnight to give the title compound (411 mg, 81 %) as a yellow solid, mp 229–230° C.

Analysis for C19H13ClN3O4. C5H14NO. 1.1 H2O Calculated: C, 56.88; H, 5.81; N, 11.06 Found: C, 56.91; H, 5.47; N, 10.98 1H NMR (DMSO-d6): 8.09–8.12 (m, 2H), 7.31 (dd, J-8.6, 2.1 HZ, 1H), 7.07 (d,j=8.5 Hz, 1H), 6.75–6.82 (m, 2H), 3.80–3.85 (m, 2H), 3.77 (s, 3H), 3.37–3.40 (m, 2H), 3.09 (s, 9H), 2.04 (2, 3H).

Example 50

2-(4-Benzyloxyphenyl)-7-chloro-4-hydroxy-1,2,5,10-tetrahydropyridazino[4,5-b]quinoline-1,10-dione choline salt.

To a stirred suspension of 7-chloro-3-methoxycarbonyl-4-oxo-1,4-dihydroquinoline-2-carboxylic acid N-2-(4-benzyloxyphenyl)hydrazide (1.19 g, 2.50 mM) in methanol (50 mL) was added methanesulfonic acid (2.4 mL) and the resulting mixture was refluxed for 1 hr. After cooling to room temperature, the reaction mixture was filtered and the collected solids washed with ether and air dried to give 900 mg of material which was saved for further purification. The filtrate was diluted with an equal volume of water and, after stirring for 30 min, the resulting suspension was filtered; the collected solids were washed with water and ether and air dried to provide the title compound (151.8 mg) in the free acid form. The solids (900 mg) which were initially collected and saved were recrystallized by dissolving in a hot mixture of methanol (3.8 L) and methanesulfonic acid (63 mL) and then allowing to cool to room temperature. The resulting suspension was filtered to remove a precipitate and the filtrate was diluted with an equal volume of water and stirred overnight. The resulting precipitate which formed was collected, washed with water and ether and then air dried to give the title compound (422.2 mg) in the free acid form (total combined yield of the free acid title compound: 574 mg, 52%); MS(CI): 446 (M+H). 300 MHz 1H NMR (DMSO-d6): 12.71 (br s, 1H, exchangeable), 11.98 (br s, 1H, exchangeable), 8.14 (d, J=8.6 Hz, 1H), 8.03 (s, 1H), 7.47–7.32 (m, 9H), 7.07 (d, J=8.9 Hz, 1H), 5.14 (s, 2H).

To a stirred suspension of 2-(4-benzyloxyphenyl)-7-chloro-4-hydroxy-1,2,5,10-tetrahydropyridazino[4,5-b]quinoline-1,10-dione (515 mg, 1.16 mM) in methanol (77 mL) was added choline hydroxide (45 weight % in methanol, 0.36 mL, 1.28 mM). The resulting mixture was filtered to separate a small quantity of fine solids and the filtrate was concentrated to leave an oily residue. This residue was diluted with toluene (70 mL) and concentrated. The residue was diluted with toluene/ethanol (70 mL/20 mL) and concentrated. The residue was diluted with a final portion of toluene (70 mL) and concentrated to provide the choline salt title compound (640 mg, 99%) as a yellow-green solid, mp 304–306° C.; MS(FAB): 446 (M+1), 444 (M−1).

Analysis for C24H16ClN3O4. 0.5 H2O. 1.0 C5H14NO Calculated: C, 61.95; H, 5.43; N, 9.89 Found: C, 62.31; H, 5.59; N, 10.02 300 MHz- 1H NMR (DMSO-d6): 8.11–8.09 (m, 2H), 7.48–7.28 (m, 8H), 7.00 (d, J=8.88 Hz, 2H), 5.13 (s, 2H), 3.83 (br s, 2H), 3.09 (s, 9H)

a) 7-Chloro-3-methoxycarbonyl-4-oxo-1,4-dihydroquinoline-2-carboxylic acid N-2-(4-benzyloxyphenyl)hydrazide.

The 7-chloro-3-methoxycarbonyl-4-oxo-1,4-dihydroquinoline-2-carboxylic acid N-2-(4-benzyloxyphenyl)hydrazide used in Example 50 was prepared according to the procedure used in Example 41) except that 4-benzyloxyphenylhydrazine was used instead of 4-chloro-2-methylphenyl-hydrazine.

Example 51
7-Chloro-2-(2,4-dichlorophenyl)-4-hydroxy-1,2,5,10-tetrahydropyridazino[4,5-b]quinoline-1,10-dione.

To a stirred suspension of 7-chloro-3-methoxycarbonyl-4-oxo-1,4-dihydroquinoline-2-carboxylic acid N-2-(2,4-dichlorophenyl)hydrazide (3.00 g, 6.81 mM) in methanol (1500 mL) was added methanesulfonic acid (150 mL). The resulting suspension was refluxed for 9 days and the resulting solution was then cooled to ambient temperature and concentrated to one-half its original volume using a rotary evaporator. The suspension which was obtained was stirred at room temperature for 30 min and filtered to separate the solids. The filtrate was diluted with an equal volume of water whereupon a precipitate formed. This mixture was stirred at ambient temperature overnight and then filtered. The collected solids were washed with ether and then suspended in methanol (500 mL) and sonicated for 5 min. The resulting mixture was filtered to separate the solids and the filtrate was concentrated. The residue was suspended in ether and filtered. The collected solids were washed with water and ether and then air-dried to provide the title compound (198.5 mg, 7%) as a yellow solid, mp 360–361° C.; MS(CI): 408 (M+H).

Analysis for C17H8Cl3N3O3. 0.2 H2O. 0.10 CH3SO3H Calculated: C, 49.02; H, 2.35; N, 9.75 Found: C, 48.69; H, 2.10; N, 9.96 300-MHz 1H NMR (DMSO-d6): 12.99 (br s, 1H, exchangeable), 12.12 (br s, 1H, exchangeable), 8.15 (d, J=8.67 Hz, 1H), 8.07 (d, J=1.23 Hz, 1H), 7.85 (d, J=1.02 Hz, 1H), 7.60 (s, 2H), 7.47 (dd, J=1.61, 8.63 Hz, 1H)

a) 7-Chloro-3-methoxycarbonyl-4-oxo-1,4-dihydroquinoline-2-carboxylic acid N-2-(2,4-dichlorophenyl)hydrazide.

The 7-chloro-3-methoxycarbonyl-4-oxo-1,4-dihydroquinoline-2-carboxylic acid N-2-(2,4-dichlorophenyl)hydrazide used in Example 51 was prepared according to the procedure used in Example 41a) except that 2,4-dichlorophenylhydrazine was used instead of 4-chloro-2-methylphenylhydrazine.

Example 52
7-Chloro-3-(2,4-dichlorophenyl)-1-hydroxy-3,4,5,10-tetrahydropyridazino[4,5-b]quinoline-4,10-dione.

To a stirred suspension of 7-chloro-3-methoxycarbonyl-4-oxo-1,4-dihydroquinoline-2-carboxylic acid N-2-(2,4-dichlorophenyl)hydrazide (1.28 g, 2.92 mM) in methanol (645 mL) was added methanesulfonic acid (65 mL). The resulting suspension was refluxed for 10 days and the resulting solution was then cooled to ambient temperature whereupon a precipitate formed. The mixture was filtered to separated the solids and the filtrate was diluted with water (300 mL) to form another precipitate. This precipitate was collected and dried to provide the title compound (266.5 mg, 22%) yellow solid, mp 342–343° C.; MS(CI): 408 (M+H).

Analysis for C17H8Cl3N3O3. 0.1 CH3SO3H. 0.2 H2O Calculated: C, 48.73; H, 2.16; N, 9.95 Found: C, 48.69; H, 2.10; N, 9.96 300-MHz 1H NMR (DMSO-d6): 13.50 (br s, 1H, exchangeable), 8.29 (d, J=8.76 Hz, 1H), 8.19 (d, J=1.26 Hz, 1H), 7.92 (d, J=1.71 Hz, 1H), 7.70–7.61 (m, 3H)

a) 7-Chloro-3-methoxycarbonyl-4-oxo-1,4-dihydroquinoline-2-carboxylic acid N-2-(2,4-dichlorophenyl)hydrazide.

The 7-chloro-3-methoxycarbonyl-4-oxo-1,4-dihydroquinoline-2-carboxylic acid N-2-(2,4-dichlorophenyl)hydrazide used in Example 52 was prepared according to the procedure used in Example 51).

Example 53
7-Chloro-4-hydroxy-2-[2-(4-methoxyanilino)ethyl]-1,2,5,10-tetrahydropyridazino[4,5-b]quinoline-1,10-dione.

2-(2-Bromoethyl)-7-chloro-4-hydroxy-1,2,5,10-tetrahydropyridazino[4,5-b]quinoline-1,10-dione (1.00 g, 2.7 mM, prepared in Example 4a. and p-anisidine (1.33 g, 10.8 mM) were stirred and heated to reflux in DMF (20 mL) for 1.5 hours to give a brown solution. The solution was cooled to room temperature and ether (80 mL) was added to give a dark suspension. The suspension was stirred for two hours and filtered. The collected solids were washed with ether (150 mL) to give the title compound as a tan powder (1.17 g, 60%), mp 239–241° C.; MS(CI):413.

Analysis for C20H17ClN4O4. HBr. 3.0 C3H7NO. 0.5 H2O: Calculated: C, 48.24; H, 5.58; N, 13.58 Found: C, 47.80; H, 5.20; N, 13.93 300 MHz 1H NMR (DMSO-d6): 8.14 (d, J=8.7 Hz, 1H), 8.09 (d, J=1.9 Hz, 1H), 7.35 (d, J=8.7 Hz, 1H), 6.75 (d, J=8.9 Hz, 2H), 6.58 (d, J=8.9 Hz, 2H), 3.96 (t, J=6.8 Hz, 2H), 3.62 (s, 3H), 3.27 (t, J=6.8 Hz, 2H).

Example 54
7-Chloro-2-(3-chloro-4-hydroxyphenyl)-4-hydroxy-1,2,5,10-tetrahydropyridazino[4,5-b]quinoline-1,10-dione.

7-Chloro-2-(3-chloro-4-methoxyphenyl)-4-hydroxy-1,2,5,10-tetrahydropyridazino[4,5-b]quinoline-1,10-dione (previously prepared in Example 37 1.00 g, 2.47 mM) was stirred in methanesulfonic acid (20 mL) to give a black solution. This solution was heated to 145° C. for 6 hours and cooled to room temperature. Water (60 mL) was added to give a tan suspension which was stirred for 3 hours and filtered. The collected solids were washed with water and ether to give the title compound as a gold powder (0.98 g, 76 %), mp 350–353° C.; MS(CI): 390.

Analysis for C17H9Cl2N3O4. H2O. 1.2 CH3SO3H: Calculated: C, 41.76; H, 3.04; N, 8.02 Found: C, 41.74; H, 2.76;

N, 7.68 300 MHz 1H NMR (d6-DMSO): 8.15 (d, J=8.5 Hz, 1H), 8.05 (d, J=1.9HZ, 1H), 7.53 (d, J=2.2HZ, 1H), 7.45 (d, J=8.5 Hz, 1H), 7.33 (dd, J=2.2,8.7 Hz, 1H), 7.03 (d, J=8.7 Hz, 1H).

Example 55

7-Chloro-4-hydroxy-2-(4-hydroxy-2-methylphenyl)-1,2,5,10-tetrahydropyridazino[4,5-b]quinoline-1,10-dione.

7-Chloro-4-hydroxy-2-(4-methoxy-2-methylphenyl)-1,2,5,10-tetrahydropyridazino[4,5-b]quinoline-1,10-dione (1.00 g, 2.61 mM) was stirred in methanesulfonic acid (10 mL) to give a brown solution. This solution was heated to 150° C. for 3 hours and cooled to room temperature. The cooled solution was added dropwise to water (50 mL) with stirring to give a grey suspension which was stirred for 20 hours and filtered. The collected solids were washed with water and then suspended in water (50 mL). To this suspension was added choline hydroxide solution (2 mL, 45 wt % in methanol) which dissolved the solids to give a brown solution. This solution was heated to reflux for 1 hour, additional choline hydroxide solution (2 mL) was added and the solution was heated to reflux for 3 hours. The solution was cooled to room temperature and acidified to pH=1 with 1N HCl to give a brown suspension. The suspension was filtered and the collected solids were washed with water to give a brown solid. Several recrystallizations from hot methanol gave the title compound as an off-white powder (0.35 g, 36%), mp 287° C. (decomp.); MS(CI): 370.

Analysis for C18H12ClN3O4. H2O. 0.7 CH3OH: Calculated: C, 54.75; H, 4.13; N, 10.24 Found: C, 54.75; H, 3.87; N, 10.18 300 MHz 1H NMR (d6-DMSO): 12.60 (br s, 1H, exchang.), 12.00 (br s, 1H, exchange), 9.55 (br s, 1H, exchang.), 8.16 (d, J=8.6 Hz, 1H), 8.06 (s, 1H), 7.45 (d, J=8.6 Hz, 1H), 7.07 (d, J=8.4 Hz, 1H), 6.70 (s, 1H), 6.6 (d, J=8.4 Hz, 1H), 2.00 (s, 3H).

Example 56

7-Chloro-2-(4-chloro-2-methylphenyl)-4-hydroxy-1,2,5,10-tetrahydropyridazino[4,5-b]quinoline-1,10-dione.

This is an alternate synthesis of this compound previously described in Example 42.

3-Benzyl-7-chloro-2-(4-chloro-2-methylphenyl)-1,2,3,4,5,10-hexahydropyridazino[4,5-b]quinoline-1,4,10-trione, 0.61 g, 1.28 mM) was stirred in methanesulfonic acid (12 mL) to give a viscous amber solution. This solution was warmed to 45° C. for 6.5 hours to give a pea green suspension which was cooled to room temperature. Ice (50 mL) was added with stirring to give a light green suspension which was filtered. The collected solids were washed with water and ether to give a grey powder (0.49 g). A portion of this powder (0.36 g) was stirred in methanol and choline hydroxide solution (2 mL, 1M) was added. Most of the solids dissolved and the mixture was filtered to remove the insoluble material. The filtered solution was acidified to pH=1 with 1N HCl to give a tan suspension. Methanol (2 mL) was removed under a N2 (g) stream and the suspension filtered. The collected solids were washed with water and ether to give the title compound as an off-white powder (0.30 g, 82%), identical to the material previously prepared in Example 42.

The starting material, 3-benzyl-7-chloro-2-(4-chloro-2-methylphenyl)-1,2,3,4,5,10-hexahydropyridazino[4,5-b]quinoline-1,4,10-trione, was prepared according to the following procedures:

a) 2-Benzylidene-1-(4-chloro-2-methylphenyl)hydrazine.

To a stirred suspension of 4-chloro-2-methylphenylhydrazine hydrochloride (1.00 g, 5.18 mM) in ethanol (15 mL) was added benzaldehyde (0.66 g, 6.22 mM) and sodium acetate (0.51 g, 6.2 mM). After stirring the resulting mixture for 3 hr at room temperature, an additional quantity of benzaldehyde (0.11 g, 1.3 mM) was added and stirring continued for 30 min. The reaction mixture was poured into water and the resulting mixture extracted with ether. The combined ether extracts were dried (MgSO₄), filtered and concentrated to leave a yellow oil (1.71 g) which contained the title compound contaminated with the diethyl acetal of benzaldehyde. The acetal was distilled off by warming (70° C.) the mixture under high vacuum. The residue consisted of the pure title compound (1.23 g, 97%) as an orange solid which was used as is in the next step.

300 MHz 1H NMR (CDCl3): 7.79 (s, 1H), 7.68 (s, 1H), 7.65 (s, 1H), 7.49 (d, J=6.3, 1H), 7.42–7.26 (m, 4H), 7.16 (dd, J=2.5, 6.0 Hz, 1H), 7.06 (d, J=2.5 Hz, 1H), 2.21 (s, 3H).

b) 1-Benzyl-2-(4-chloro-2-methylphenyl)hydrazine.

To a stirred solution of 2-benzylidene-1-(4-chloro-2-methylphenyl) hydrazine (2.40 g, 9.81 mM) in anhydrous tetrahydrofuran (43 mL) was added dropwise a solution of borane in tetrahydrofuran (4.6 mL of a 1M solution, 4.6 mM). A gas evolution occurred during and after the addition. After the addition was completed, the reaction mixture was stirred for 20 min at room temperature and then saturated carefully with hydrogen chloride gas at room temperature. A white precipitate gradually formed as the HCl gas was added to the reaction mixture. The reaction mixture was stirred for 20 min after the addition of the HCl and then quenched by the careful dropwise successive addition of water (150 mL) and 10% hydrochloric acid (5 mL). The resulting solution was concentrated to remove most of the tetrahydrofuran. The residual mixture was made basic by adding solid potassium carbonate and then extracted with ether. The combined extracts were dried (MgSO4), filtered and concentrated to leave a pale yellow oil (2.38 g). This material was flash chromatographed over silica gel using hexane/ether (3:1) as the eluant. The fractions containing the desired material were combined and concentrated to leave the title compound as a yellow oil (1.30 g, 53.7%); MS(CI): 247 (M+H). 300 MHz 1H NMR (CDCl3): 7.22–7.41 (m, 6H), 7.14 (d, J=2.4 Hz, 1H), 7.01 (d, J=2.4 Hz), 4.90 (br s, 1H, exchangeable), 3.95 (s, 2H), 3.77 (br s, 1H, exchangeable), 1.98 (s, 3H).

c) 7-Chloro-3-methoxycarbonyl-4-oxo-1,4-dihydroquinoline-2-carboxylic acid N-1-benzyl-N-2-(4-chloro-2-methylphenyl)hydrazide.

7-Chloro-3-methoxycarbonyl-4-oxo-1,4-dihydroquinoline-2-carbonyl chloride (0.58 g, 1.93 mM) was dissolved in tetrahydrofuran (50 mL) and added dropwise over 15 minutes to a solution of 1-benzyl-2-(4-chloro-2-methyl)phenylhydrazine (1.00 g, 4.05 mM) in tetrahydrofuran (100 mL) at 0° C. The resulting amber solution was stirred for 45 minutes at 0° C. and diluted with water (75 mL) maintaining 0° C. with cooling. The resulting solution was further diluted at 0° C. with 1N HCl (180 mL) to give a white suspension. The suspension was stirred at 0° C. for 1 hour and filtered. The collected solids were washed with 1N HCl, water, and ether to give, after air drying, the title compound as a white powder (0.83 g, 84%), mp 172–175° C.

Analysis for C26H21Cl2N3O4.0. 6 H2O. 0.4 C4H10O: Calculated: C, 60.18; H, 4.79N, 7.63 Found: C, 60.21; H, 4.44; N, 7.70 300 MHz 1H NMR (d6-DMSO): 12.44 (s, 1H, exchang.), 8.04 (d, J=8.6 Hz, 1H), 7.52 (d, J=1.4 Hz, 1H), 7.43–7.31 (m, 6H), 7.11–6.85 (m, 3H), 4.85 (br s, 2H), 3.69 (s, 3H), 1.76 (s, 3H).

d) 3-Benzyl-7-chloro-2-(4-chloro-2-methylphenyl)-1,2,3,4,5,10-hexahydropyridazino[4,5-b]quinoline-1,4,10-trione.

7-Chloro-3-methoxycarbonyl-4-oxo-1,4-dihydroquinoline-2-carboxylic acid N-1-benzyl-N-2-(4-chloro-2-methyl)phenylhydrazide (0.92 g, 1.80 mM) was stirred in methanol (37 mL) and choline hydroxide solution (1.03 mL, 45 weight % in methanol) was added to give a slightly brown solution. This solution was heated to reflux for 12 hours and cooled to room temperature. The methanol was removed under a N2 (g) stream to give an amber residue. Choline hydroxide solution (1 mL, 45 weight % in methanol) was added and the resulting thick solution was stirred for 1 hour. Methanol (40 mL) was added and the solution was cooled to −15° C. 1N HCl (10 mL) was added dropwise at −15° C. with stirring to give a white suspension. Methanol (15 mL) was removed under a N2 (g) stream and the suspension was filtered. The collected solids were washed with water and ether to give the title compound as an off-white powder (0.76 g, 89%), mp 279–281° C.; MS(CI):478.

Analysis for $C_{25}H_{17}Cl_2N_3O_3$. $H_2O$. 0.3 $CH_3OH$: Calculated: C, 60.06; H, 4.02; N, 8.31 Found: C, 60.14; H, 3.90; N, 8.34 300 MHz 1H NMR (d6-DMSO): 12.68 (s, 1H, exchang.), 8.19 (d, J=1.9 Hz, 1H), 8.16 (d, J=8.6 Hz, 1H), 7.50 (dd, J=1.9, 8.6 Hz, 1H), 7.35–7.24 (m, 6H), 6.94–6.91 (m, 2H), 5.28 (d, J=16.3 Hz, 1H), 4.60 (d, J=16.3 Hz, 1H), 1.69 (s, 3H).

Example 57

7,9-Dichloro-2-(2,4-dimethylphenyl)-4-hydroxy-1,2,5,10-tetrahydropyridazino[4,5-b]quinoline-1,10-dione sodium salt. This is the sodium salt of the compound prepared in Example 47.

7,9-Dichloro-2-(2,4-dimethylphenyl)-4-hydroxy-1,2,5,10-tetrahydropyridazino[4,5-b]quinoline-1,10-dione (prepared as described in Example 47, 375.6 mg, 0.925 mM) was dissolved in water (20 mL) containing 0.1N sodium hydroxide (9.25 mL, 0.925 mM) and methanol (4 mL) by swirling and sonication. The resulting solution was filtered through a Gelman Glass Acrodisc filter (0.45 microns) and the filtrate concentrated to dryness. The residue was triturated with isopropanol (10 mL) and the resulting mixture was filtered. The collected solids were washed with isopropanol (5 mL) and then dried under high vacuum at 100° C. overnight to provide the title compound as a yellow solid (310.4 mg, 79%), mp 369–370° C.

Analysis for $C_{19}H_{12}Cl_2N_3O_3$. 1.0 Na. 1.70 $H_2O$. 0.02 $(CH_3)_2CHOH$ Calculated: C, 50.32; H, 3.12; N, 9.08 Found: C, 50.20; H, 3.44; N, 9.21 1H NMR (DMSO-d6): 8.01 (d, J=2.2 Hz, 1H), 7.28 (d, J=2.0 Hz, 1H), 7.01–7.08 (m, 3H), 2.30 (s, 3H), 2.04 (s, 3H).

Examples 58–81 are presented in Table 1 adjacent to the formula and scheme pages before the claims.

Example 82

7-Chloro-4-hydroxy-2-(2-fluorobenzyl)-1,2,5,10-tetrahydropyridazino [4,5-b]quinoline-1,10-dione.

To a stirred suspension of 2-pyrrolidinocarbamide-7-chloro-4-hydroxyquinoline-3-carboxylic acid (1.068 g, 3.3 mM) in tetrahydrofuran (60 mL) at ambient temperature was added dicyclohexylcarbodiimide (0.795 g, 3.85 mM). A tetrahydrofuran solution (20 mL) of N-t-butoxycarbonyl-N'-2-fluorobenzylhydrazine (1.10 g, 4.59 mM, prepared as described in 82c) was immediately added to the above suspension. The reaction mixture was stirred at room temperature for four hours. Upon completion of the coupling, the byproduct urea was removed via vacuum filtration. Partial purification by flash column chromatography employing 5% methanol in methylene chloride yielded the desired hydrazide (1.67 g, 3.0 mM, 92%). To the hydrazide suspended in tetrahydrofuran (80 nL) was added methanesulfonic acid (9.0 mL, 139 mM). The reaction was stirred at room temperature for 24 hours then poured into ice water (600 mL). The resulting precipitate was isolated, dried, and triturated/sonicated with methanol (20 mL) and isolated to yield after drying under vacuum at 50° C. 0.733 g (65.9%) of the title compound as an off-white solid, mp>300° C.; MS (CI): 372 (M+H).

Analysis for $C_{18}H_{11}N_3O_3FCl$: Calculated: C, 58.16; H, 2.98; N, 11.30 Found: C, 57.81; H, 3.20; N, 11.08 300 MHz 1H NMR (DMSO-d6): 12.68 (s,1H, exchangeable), 11.96 (s, 1H, exchangeable), 8.15 (d, J=8.7 Hz, 1H), 8.03 (s, 1H), 7.43 (d, 1H, J=8.6 H2), 7.15–7.32 (m, 4H), 5.17 (s, 2H).

a) The starting material, 2-pyrrolidinocarbamide-7-chloro-4-hydroxyquinoline-3-carboxylic acid, was prepared in the following manner:

To a suspension of 3-carbomethoxy-2-pyrrolidinocarbamide-7-chloro-4-hydroxyquinoline (2.52 g, 7.5 mM) in de-ionized water (40 mL) was added dropwise a solution (20 mL) of an aqueous potassium hydroxide (882 mg, 15.75 mM). Upon complete addition, the reaction was warmed to 60° C. After 3 hours, the reaction was filtered to remove a small amount of insoluble material. The filtrate was then acidified to pH=1 which yielded a white precipitate. The solid was isolated by vacuum filtration, washed with water, and dried at 30° C. under vacuum for 16 hours. This provided the desired title compound (1.5 g, 64%) as a white solid, mp 225–8° C.; MS (CI): 321 (M+H). 300 MHz 1H NMR (DMSO-d6): 8.28 (d, J=8.8 Hz, 1H), 7.77 (s, 1H), 7.64 (d, 1H, J=8.7), 3.52–3.57 (m, 23H), 3.17–3.19 (m, 2H), 1.83–1.98 (m, 4H).

b) The starting material, 3-carbomethoxy-2-pyrrolidinocarbamide-7-chloro-4-hydroxyquinoline, was prepared in the following manner:

To a suspension of 3-carbomethoxy-7-chloro-4-hydroxy quinoline-2-carboxylic acid (2.25 g, 8.0 mM) in tetrahydrofuran (20 mL) at ambient temperature under a N2 atmosphere was added dicyclohexylcarbodiimide (1.65 g, 8.0 mM) and pyrrolidine (0.596 g, 8.4 mM). The reaction was stirred room temperature for 15 hours after which time the byproduct urea was removed via filtration. The desired product was purified via flash column chromatography employing 5% methanol in chloroform to provide the title compound (2.52 g, 94.3%) as a tan solid, mp 215° C.; MS (CI): 335 (M+H). 300 MHz 1H NMR (DMSO-d6): 8.12 (d, J=8.7 Hz, 1H), 7.60 (d, 1H, J=1.8 Hz), 7.47 (dd, 1H, J=8.8,2.0 Hz), 3.69 (s, 3H), 3.40–3.49 (m, 2H), 3.27–3.33 (m, 2H), 1.80–1.96 (m, 4H).

The starting material, N-t-butoxycarbonyl-N'-2-fluorobenzylhydrazine, was prepared in the following manner:

c) To a mixture of t-butylcarbazate (17.84 g, 135 mM) and 2-fluorobenzylbromide (3.2 mL, 26.5 mM) in dimethylformamide (30 mL) warmed to 50° C. was added triethylamine (7.4 mL, 53.1 mM). After stirring at 50° C. for 30 minutes, the reaction mixture was diluted with water and extracted with methylene chloride. The combined organic extracts were washed with water and brine, dried over $MgSO_4$, and concentrated in vacuo. The crude product was purified by flash column chromatography employing 1:1 diethylether:hexane as eluant. This provided the title compound (5.13 g, 80%) as a white solid; MS (CI): 241 (M+H). 300 MHz 1H NMR (DMSO-d6): 8.27 (br s, 1H), 7.40–7.50 (m, 1H), 7.25–7.36 (m, 1H), 7.09–7.20(m, 2H), 4.48 (br s, 1H), 3.87–3.94 (m, 2H), 1.37 (s, 9H).

Example 83

7-Chloro-1-hydroxy-3-(3-nitrophenyl)-3,4,5,10-tetrahydropyridazino[4,5-b]quinoline-4,10-dione.

The title compound was made generally as set forth in Example 14 using appropriate corresponding precursors to make the title compound using butanol in the place of ethanol. Also, the product was isolated prior to treatment in methanol with methanesulfonic acid.

Analysis for C17H9N4O5Cl1 Calculated: 53.07; H, 2.36; N, 11.02 Found: 53.55; H, 2.54; N, 10.94 NMR (DMSO-d6): 7.63 (d, J=8.9 Hz, 1H), 7.80–7.91 (m, 1H), 8.18–8.36 (m, 4H), 8.64 (s, 1H), 12.71 (br s, 1H), 13.36 (br s, 1H) MS(Cl): 385 (M+H) m.p. (0° C.):>250

Example 84

7-Chloro-2-(3-fluorophenyl)-4-hydroxy-1,2,5,10-tetrahydropyridazino[4,5-b]quinoline-1,10-dione.

The title compound was made general as set forth in Example 15, using appropriate corresponding precursors to make the compounds listed.

Analysis for C17H9N3O3ClF Calculated: C, 53.57; H, 3.07; N, 14.56 Found: C, 53.55; H, 2.94; N, 14.44 NMR (DMSO-d6) 7.18–7.32 (m, 1H), 7.46–7.60 (m, 4H), 8.06 (s, 1H), 8.17 (d, J=8.7 Hz, 1H), 12.09 (br s, 1H), 12.92 (br s, 1H) MS(C1): 358 (M+H) m.p. (0° C.): >250

Examples 85–94

Compounds were made generally as set forth in Example 35 using the appropriate corresponding precursors. The physical data and yields from the precursor acyl hydrazide are presented in Table 2 in the pages prior to the claims.

Examples 95–103

Compounds were made as generally set forth in Example 80 using the appropriate corresponding precursors with physical data and yields from the 2-pyrrolidinoquinoline precursors presented in Table 3 before the claims.

Example 104

7-Chloro-4-hydroxy-2-(2,6-dihydroxyphenyl)-1,2,5,10-tetrahydropyridazino [4,5-b]quinoline-1,10-dione.

A suspension of 7-chloro-4-hydroxy-2-(2,6-dimethoxyphenyl)-1,2,5,10-tetrahydropyridazino[4,5-b]quinoline-1,10-dione (0.5618 g, 1.4 mM) was allowed to reflux in 50 mL of 48% hydrobromic acid. After approximately 45 minutes the suspension became an orange solution. After 2 hours at reflux HPLC analysis indicated that the reaction was complete. Upon cooling, the solution afforded a precipitate that was removed via filtration and washed with water until the aqueous washing were no longer acidic. The solid was then dissolved in 4 mL of 45% choline hydroxide in methanol and filtered through a fine fritted Buchner funnel to remove any particulate matter. Acidification with concentrated HCl afforded a tan precipitate that was removed via filtration. The wet solid was dissolved in methanol and the solvent was evaporated to afford the desired product (0.230 g, 44.3%) as a tan solid.

Analysis for C17H11N3O5Cl. 0.7 HBr Calculated: C, 47.55H, 2.75 N, 9.78 Found: C, 47.85 H, 3.85 N, 9.70 Chemical Ionization: m+1: 372 300 MHz Proton NMR (DMSO-d6/TFA-d): 12.65 (br s, 1H, exchangeable), 8.2 (d,1H, J=9.0 Hz), 8.12 (s, 1H), 7.47 (d, 1H, J=9.0 Hz), 6.80 (d, 1H, J=6.0 Hz) 6.74 (d, 1H), 6.70 (s, 1H).

Example 105

7-Chloro-4-hydroxy-2-(4-carboxyphenyl)-1,2,5,10-tetrahydropyridazino [4,5-b]quinoline-1,10-dione.

A suspension of 7-chloro-4-hydroxy-2-(4-cyanophenyl)-1,2,5,10-tetrahydropyridazino[4,5-b]quinoline-1,10-dione (0.400 g, 1.04 mM) in 50 mL of 1N KOH was allowed to reflux over a 5 hour period as the reaction was monitored via HPLC. The initial suspension slowly became a yellow solution. Total conversion to a new material was accomplished after 5 hours of reflux as judged via HPLC. The solution was cooled to 0° C. and acidified with concentrated HCl. Upon acidification a precipitate formed immediately and was removed via suction filtration. The yellow filter cake was washed with water and then suspended in a 1:1 solution of ethanol:methanol and the solvent was removed under vacuum at 50° C. This was repeated until the yellow powder was a free flowing solid affording (0.400 g, 100%) of the desired product.

Analysis for C18H10N3O5Cl. 2.7 HCl Calculated: C, 44.38 H, 2.87 N, 9.15 Found: C, 44.83 H, 2.65 N, 8.71 Chemical Ionization: m+1: 384 300 MHz Proton NMR (DMSO-d6/TFA-d): 13.04 (br s, 1H, exchangeable), 12.20 (br s, 1H exchangeable), 8.1 (d,1H, J=9.0 Hz), 8.08 (s, 1H), 8.03 (d, 2H J=9.0 Hz), 7.70 (d, 2H, J=9.0 Hz) 7.465 (d, 1H).

Example 106

7-Chloro-4-hydroxy-2-(4-hydroxyphenyl)-1,2,5,10-tetrahydropyridazino[4,5-b]quinoline-1,10-dione.

To a 50 mL solution of 5:1 48% HBr:methanesulfonic acid was added 7-chloro-4-hydroxy-2-(4-methoxyphenyl)-1,2,5,10-tetrahydropyridazino[4,5-b]quinoline-1,10-dione (1.0328 g, 27.9 mM). The resulting suspension was heated to 110° C. over 3.5 hours. HPLC analysis afforded a total conversion to a new material. The suspension was cooled to room temperature and filtered through a Buchner funnel. The yellow solid was washed 2x with 100 mL portions of distilled water followed by 200 mL of a 1:1 solution of THF:ether. The material was then washed with hexanes until the yellow solid was free flowing. This solid was allowed to air dry for 72 hours prior to submission for analysis. No percent yield was recorded for this reaction.

Analysis for C17H9N3O4Cl2. 2.3HBr Calculated: C, 35.43 H, 1.97 N, 7.29 Found: C, 35.40 H, 1.95 N, 6.85 Chemical Ionization: m+1: 390 300 MHz Proton NMR (DMSO-d6/TFA-d): 8.08 (s,1H), 7.49 (s, 1H), 7.30 (d, 2H J=8.73 Hz), 6.8 (d, 2H, J=8.73).

Example 107

7-Chloro-4-hydroxy-2-(4-carboxamidophenyl)-1,2,5,10-tetrahydropyridazino[4,5-b]quinoline-1,10-dione.

Into a 50 mL round bottom flask was placed 7-chloro-4-hydroxy-2-(4-cyanophenyl)-1,2,5,10-tetrahydropyridazino [4,5-b]quinoline-1,10-dione (0.2040 g, 0.558 mM). This was dissolved in 6 mL of H2SO4 and warmed to 50° C. The warm solution was then poured onto 10.0 g of crushed ice affording a yellow solid. The solid was removed from the aqueous solution via suction filtration and washed with 60 mL of distilled water followed by 30 mL of 1N NaHCO3. The resulting yellow paste was suspended in 1:1 ethanol:methanol and the solvent was removed under vacuum until the solid was free flowing. Additional washing with 60 mL of methanol followed by 200 mL of THF afforded a yellow solid that was free flowing. After additional air drying (0.187 g, 87.7%) of desired product was recovered as a yellow solid.

Analysis for C18H11N4O4Cl. 1.3 H2SO4 Calculated: C, 42.37 H, 2.68 N, 10.98 Found: C, 42.75 H, 3.10 N, 10.61 FAB: m+1: 277.2, 257.1, 299.1, 383.1 300 MHz Proton NMR (DMSO-d6/TFA-d): 8.23 (s, 1H), 8.10 (s, 1H), 8.05 (d, 2H J=8.49 Hz), 7.70 (d, 2H, J=8.49), 7.465 (d, J=8.49 Hz).

Example 108
7-Chloro-4-hydroxy-2-(4-tetrazolephenyl)-1,2,5,10-tetrahydropyridazino[4,5-b]quinoline-1,10-dione.

To 10 mL of NMP was added 7-chloro-4-hydroxy-2-(4-cyanophenyl)-1,2,5,10-tetrahydropyridazino[4,5-b]quinoline-1,10-dione (0.5 g, 1.37 mM) followed by triethylamine (0.206 g, 1.57 mM) and sodium azide (0.534 g, 8.22 mM). This suspension was vigorously stirred and heated to 170° C. over a period of 6 hours . At this time HPLC analysis indicated that the reaction was completed. The solution was allowed to cool and a precipitate began to form. To the cooled suspension was added diethyl ether until no further precipitation was observed. The solid was removed via suction filtration and washed with ether until the solid was a free flowing tan powder. This was then suspended in 100 mL of 1N HCl to remove any excess sodium azide and triethylamine hydrochloride. The solid was removed via filtration and washed with a 1:1 methanol:ether solution until the tan solid was a free flowing powder. After additional air drying (0.552 g, 99.1%) of the desired product was recovered.

Analysis for C18H11N4O4Cl. 2.4 H2O Calculated: C, 47.93 H, 3.30 N, 21.73 Found: C, 47.36 H, 3.32 N, 10.57 FAB: m+1: 277.2, 257.1 300 MHz Proton NMR (DMSO-d6): 12.10 (br s, 1H exchangeable) 8.19–8.12 (m, 4H), 8.065 (s, 1H), 7.85 (d, 3H J=9.00 Hz).

Example 109
7-Chloro-4-hydroxy-2-(4-N,N-diethylcarboxamidophenyl)-1,2,5,10-tetrahydropyridazino[4,5-b]quinoline-1,10-dione.

To 20 mL of anhydrous THF was suspended 7-chloro-4-hydroxy-2-(4-carboxyphenyl)-1,2,5,10-tetrahydropyridazino[4,5-b]quinoline-1,10-dione (0.3436 g, 0.897 mM) under an atmosphere of nitrogen. To this suspension was added $SOCl_2$ (0.13 mL, 1.79 mM). This was then heated to reflux over a 60 minute period at which point 1 mL of DMF was then added. Upon the addition of the DMF the suspension instantaneously became a light yellow solution which eventually reverted back to a yellow suspension after 5 minutes. The THF was removed under reduced pressure and 10 mL of DMF was added at room temperature. The resulting dark orange solution was cooled to –10° C. To this was added diethylamine, (0.27 mL, 2.69 mM). Immediately upon addition of the diethylamine a dark red precipitate formed. This suspension was kept cold while 50 mL of 1N HCl was slowly added along with 50 mL of saturated NaCl affording a yellow precipitate. The precipitate was removed via filtration and washed with 200 mL of water followed by 1000 mL of ether. Additional washing with 4:1 ether:methanol afforded a free flowing solid. After additional air drying the desired product (0.1485 g, 38.1 %) was obtained as a yellow solid.

Analysis for C22H19N4O4Cl. 1.7 HCl Calculated: C, 52.75 H, 4.16 N, 11.18 Found: C, 52.63 H, 4.45 N, 10.85 Chemical Ionization: m+1: 439 300 MHz Proton NMR (DMSO-d6/TFA-d): 12.90 (br s, 1H exchangeable), 12.08 (br s, 1H exchangeable), 8.21 (s,1H J=9.00), 8.11 (s, 1H), 87.67 (d, 2H J=9.00 Hz), 7.48–7.46 (m, 3H J=6.15), 3.47–3.25 (br m, 4H), 1.15 (br s, 6H).

Example 110
7-Chloro-4-hydroxy-2-(4-carboxymethylphenyl)-1,2,5,10-tetrahydropyridazino [4,5-b]quinoline-1,10-dione.

To 50 mL of absolute methanol was added 7-chloro-4-hydroxy-2-(4-carboxyphenyl)-1,2,5,10-tetrahydropyridazino[4,5-b]quinoline-1,10-dione (0.30 g, 0.785 mM). To this white suspension was added two drops of concentrated $H_2SO_4$ and the suspension was allowed to reflux as the reaction was monitored via HPLC over a 26 hour period. The suspension was allowed to cool to room temperature upon which the suspension was diluted 100 mL of ether affording additional precipitate. The precipitate was removed via suction filtration and washed with 50 mL of 7:1 ether:methanol. After air drying the desired product (0.327 g, 100%) was obtained as a white solid.

Analysis for C19H12N3O5Cl. 1.5 HCl Calculated: C, 50.43 H, 3.01 N, 9.21 Found: C, 50.91 H, 3.60 N, 9.36 Chemical Ionization: m+1: 398 300 MHz Proton NMR (DMSO-d6 FFA-d): 8.15 (d,1H J=9.00), 8.05 (d, 3H), 7.75 (d, 2H J=9.00 Hz), 7.47 (d, 1H, J=9.00), 3.87 (s, 3H).

Example 111
7-Chloro-4-hydroxy-2-(4,4-dimethyl-2,5-dioxooxaxolidin-1-ylethyl)-1,2,5,10-tetrahydropyridazino[4,5-b]quinoline-1,10-dione.

Sodium hydride, 60% in mineral oil (150 mg, 3.75 mM) was washed with dry hexane and suspended in dimethylformamide (20 mL). 4,4-dimethyl-oxazoline-2,5-dione (580 mg, 4.5 mM) was added portionwise over 15 minutes at room temperature. The resulting mixture was stirred 15–20 minutes at room temperature. At this point the starting material 7-chloro-4-hydroxy-2-(2-bromoethyl)-1,2,5,10-tetrahydropyridazino[4,5-b]quinoline-1,10-dione was added and the reaction mixture was warmed quickly to 150° C. After about three hours at this temperature, the heat was removed and the reaction mixture was poured into ice-cold 1N HCl (100 mL). This mixture was stirred about 5–10 minutes and suction filtered. The filter cake was washed with water and ether, then vacuum dried to yield the desired product as a white solid (280 mg=67%).

Example 112
7-Chloro-4-hydroxy-2-(2-methyl-2-hydroxypropionamidoethyl)-1,2,5,10-tetrahydropyridazino [4,5-b]quinoline-1,10-dione.

The starting material, 7-chloro-4-hydroxy-2-(4,4-dimethyl-2,5-dioxooxaxolidin-1-ylethyl)-1,2,5,10-tetrahydropyridazino[4,5-b]quinoline-1,10-dione, (400 mg, 0.95 mM) was suspended in water (30 mL) at room temperature. To this was added 1N NaOH (2.0 mL). A clear solution resulted, which was warmed to 50° C. for 2 hours. At this time 1.2N HCl (5 mL) was added. The mixture was stirred another 30 minutes at 50° C., then cooled to room temperature. A white precipitate was recovered by filtration and dried to yield the desired compound as a white solid (330 mg=89%).

Example 113
7-Chloro-4-hydroxy-2-(2-methylthioethyl)-1,2,5,10-tetrahydropyridazino[4,5-b]quinoline-1,10-dione.

To a suspension of $NaSCH_3$ (230 mg, 3.2 mM) in dimethylformamide (20 mL), was added in one portion 7-chloro-4-hydroxy-2-(2-bromoethyl)-1,2,5,10-tetrahydropyridazino[4,5-b]quinoline-1,10-dione as a dry powder. This mixture was warmed to gentle reflux for about three hours. At this point the heat was removed and the reaction mixture was poured into ice cold 1.2N HCl (100 mL) and stirred about one hour. The resulting precipitate was vacuum filtered and washed with water and ether, then vacuum dried at 50° C. to yield 330 mg (91%) of an off white powder. mp 275–277° C.; MS: 338(M+1). NMR: 2.11(s, 3H), 2.79(t, 2H, j=7.13), 4.09(t, 2H, j=7.08), 7.42(dd, 1H, J1=8.59, J2=1.6), 8.57(d, 1H, J=1.77), 8.13(d, 1H, J=8.64), 11.8 (brs, 1H), 12.64(brs, 1H).

Example 114
7-Chloro-4-hydroxy-2-(2-methylsulfonylethyl)-1,2,5,10-tetrahydropyridazino[4,5-b]quinoline-1,10-dione.

To a solution of 7-chloro-4-hydroxy-2-(2-methylthioethyl)-1,2,5,10-tetrahydropyridazino[4,5-b]quinoline-1,10-dione (0.11 g, 0.33 mM) in methanol (5 mL) stirred at room temperature, was added OXONE, a monopersulfate compound (250 mg, 1.0 mM) dissolved in water (1 mL). The resulting mixture was stirred at room temperature for 17 hours. Water (10 mL) was added and the reaction mixture was filtered. The crude product was again stirred with warm water to completely remove the oxidant. Filtration and vacuum drying yielded the product analytically pure as a white solid. Isolated 95 mg, 75%.

Example 115
7-Chloro-4-hydroxy-2-(thiophen-2-ylmethyl)-1,2,5,10-tetrahydropyridazino[4,5-b]quinoline-1,10-dione.

To a solution of 2-(thiophen-2-ylmethyl)-t-butylcarbazate (1.0 g, 4.4 mM) and 2-pyrrolamido-3-carboxy-7-chloroquinoline-4-one (1.2 g, 3.6 mM) in tetrahydrofuran (75 mL) stirred at room temperature, was added diisopropylcarbodiimide (0.84 mL, 5.4 mM). This mixture was stirred at room temperature for 2.5 hours, then suction filtered into a second reaction flask. To the filtrate (stirred at room temperature) was added methanesulfonic acid (12 mL, 185 mM). The resulting solution was stirred 17 hours at room temperature. TLC analyses at this time indicated complete reaction. The reaction mixture was poured into ice water (200 mL). This suspension was stirred about 15 minutes and filtered. The filter cake was washed with water and ether, then vacuum dried to yield the desired compound analytically pure (1.1 g, 84%).

The physical data for examples 111–144 are presented in Tables 4–8 before the claims.

Examples 144a–1
Following procedures similar to those described in Examples 1–144 the following compounds, which are useful as starting materials to prepare the compounds of the instant invention, were prepared:

(a) 7,9-Dichloro-2,3,5,10-tetrahydropyridazino[4,5-b]quinoline-1,4,10-trione.

(b) 7-chloro-2,3,5,10-tetrahydropyridazino[4,5-b]quinoline-1,4,10-trione.

(c) 7,9-dichloro-4-hydroxy-2-(4'-methylphenyl)-1,2,5,10-tetrahydropyridazino[4,5-b]quinoline-1,10-dione.

(d) 7,9-dichloro-4-hydroxy-2-(4'-methoxyphenyl)-1,2,5,10-tetrahydropyridazino[4,5-b]quinoline-1,10-dione.

(e) 7-chloro-4-hydroxy-2-(2'-methyl-4'-bromophenyl)-1,2,5,10-tetrahydropyridazino [4,5-b]quinoline-1,10-dione.

(f) 7-chloro-4-hydroxy-2-(3'-phenoxyphenyl)-1,2,5,10-tetrahydropyridazino[4,5-b]quinoline-1,10-dione.

(g) 7-chloro-4-hydroxy-2-(hexyl)-1,2,5,10-tetrahydropyridazino[4,5-b]quinoline-1,10-dione.

(h) 7-chloro-4-hydroxy-2-(2'-methylbenzyl)-1,2,5,10-tetrahydropyridazino [4,5-b]quinoline-1,10-dione.

(i) 7-chloro-4-hydroxy-2-(3'-methoxybenzyl)-1,2,5,10-tetrahydropyridazino[4,5-b]quinoline-1,10-dione. (j) 7-chloro-4-hydroxy-2-(butyl)-1,2,5,10-tetrahydropyridazino[$^{4,5,6}$-b]quinoline-1,10-dione.

(k) 7-chloro-4-hydroxy-2-(2'-methoxybenzyl)-1,2,5,10-tetrahydropyridazino[4,5-b]quinoline-1,10-dione.

(l) 7-chloro-4-hydroxy-2-(1-methylbutyl)-1,2,5,10-tetrahydropyridazino[4,5-b]quinoline-1,10-dione.

Alkyl(C1–6)amino compounds are readily reacted with benzoylchlorides to form the alkylbenzamide PQDs. For example, $R^1$ as the 2-ethylbenzamide derivative was prepared and found to be active as a glycine receptor antagonist.

Example 145
7-Chloro-4-hydroxy-5,10-dihydro-2-(4'-methylphenyl)pyridazino[4,5-b]quinoline-1-one.

To a suspension of 7-chloro-4-hydroxy-2-(4'-methylphenyl)-1,2,5,10-tetrahydropyridazino[4,5-b]quinoline-1,10-dione (495 mg, 1.4 mmol) in tetrahydrofuran (25 mL) was added trifluoroacetic acid (4.5 ml, 58 mmol). The mixture was cooled to 0° C. with an ice bath and sodium borohydride (290 mg, 7.7 mmol) was added. The resulting solution was stirred at 0° C. for 15 minutes, the cooling bath removed, and the reaction mixture was allowed to warm to room temperature. This was then stirred at room temperature for 3 hours after which the reaction was diluted with cold water (65 mL) and stirred for an additional 10 minutes. After this time, the resulting white mixture was extracted with ethyl acetate (120 mL). The organic phase was washed with water (25 mL), brine (25 mL), dried over $Na_2SO_4$ and evaporated to dryness. The resulting residue was triturated and filtered twice from warm ethyl acetate/hexane (2:1, 15 mL) and ethyl acetate (6 mL). After drying, this afforded the title compound as a white solid (462 mg, 97%). MP=208–210° C. (d) MS(CI)340(m/e+1) NMR(d6-DMSO): 2.33(s,3H),3.79(s,2H), 6.92(dd,1H,J1=8.1Hz,J2=1.9Hz), 7.11(d,1H,J=8.2 Hz),7.24(app d, 3H), 7.43(d,2H,J=8.2Hz), 9.05(s,1H),11.99(s, 1H);

Analysis for C18H14ClN3O2. 0.95 CF3CO2H. 1.3 H2O: Calculated C50.69, H3.75, N8.91 Found C50.43, H4.06, N9.38

Examples 146–177
See Table 9 hereinbelow.

Example 178
7-Chloro-4-hydroxy-2-(4'-hydroxyphenyl)-5,10-dihydro-2H-pyridazino[4,5-b]quinoline-1-one.

To a mixture of the 7-chloro-4-hydroxy-2-(4'-methoxyphenyl)-5,10-dihydro-2H-pyridazino[4,5-b]quinoline-1-one (521 mg) in methylene chloride (50 mL), cooled in an ice/water bath, was added $BBr_3$ dropwise (0.300 mL). The mixture was stirred with cooling for 15 minutes. The cooling bath was removed and the reaction was stirred at room temperature for 3 hours. The resulting solution was cooled to 0° C. and saturated $NaHCO_3$ (55 mL) was added. The resulting mixture was stirred for 20 minutes, then the pH was adjusted with 6N HCl to pH=2. This was stirred for 15 minutes and the mixture was neutralized with saturated $NaHCO_3$. The mixture was filtered and the paste residue was washed twice with ethyl acetate. The crude solid was taken in water (25 mL) and extracted three times with ethyl acetate/THF (4:1). The organic phase was dried over $Na_2SO_4$, filtered and concentrated in vacuo to dryness. The residue was triturated in ethyl acetate to afford the title compound as a yellow solid (48%). mp 210–212° C. (decomp.); MS 342(m+H); NMR 3.78(s,2H), 7.69(d,2H,J=8.8 Hz), 6.92(dd,1H,J1=8 Hz,J2=2 Hz), 7.10(d,1H,J=8 Hz), 7.20(d,1H,J=2 Hz), 7.26(d,2H,J=8.8 Hz), 9.0 (s,1H), 9.59 (bs,1H), 1.95(bs,1H).

Example 179
7-Chloro-4-benzoyloxy-2-(4'-methylphenyl)-5,10-dihydro-2H-pyridazino[4,5-b]quinoline-1-one.

To a suspension of the 7-chloro-4-hydroxy-2-(4'-methylphenyl)-5,10-dihydro-2H-pyridazino[4,5-b]

quinoline-1-one (303 mg) in DMF (1.5 mL), was added tert-butoxy-bis(dimethylamino)methane (0.275 mL). The resulting red mixture was refluxed for 3 hours. The reaction was placed under high vacuum for 30 minutes to remove all solvents. The residue was suspended in toluene (12 mL), then 2,6-lutidine (0.135 mL) was added followed by benzoyl chloride (0.135 mL). This mixture was refluxed for 18 hours, then the reaction was cooled to room temperature and the solvents were removed in vacuo. The crude product was refluxed in ethyl acetate/ water (1:1, 20 mL) for 3 hours, cooled to room temperature and filtered in vacuo. The solids were washed with water, ethyl acetate and ether. After drying this afforded the title compound as a yellow solid (287 mg, 72%). mp 248–250° C.; MS 444 (m+H); NMR 2.34 (s,3H), 3.89(s,2H), 6.99 (dd,1H,J1=8.1 Hz, J2=2 Hz), 7.06(d,1H,J=2 Hz), 7.19(d,1H,J=8.2 Hz), 7.27(d,2H,J=8.3 Hz), 7.42(d,2H,J=8.3 Hz), 7.66(m,2H), 7.82(m,1H), 8.18(d, 2H,J=7.3 Hz), 9.23(s,1H).

Analysis C25H18ClN2O3 expected/theoretical C 67.62/ 67.65 H 4.03/4.09 N 9.44/9.47.

Example 180
7-Chloro-4-propionyloxy-2-(4'-methylphenyl)-5,10-dihydro-2H-pyridazino[4,5-b]quinoline-1-one.

The title compound was prepared by a procedure similar to that described in Example 179 but substituting propionyl chloride for benzoyl chloride. The title compound was obtained as a yellow solid (137 mg, 39%). mp 210–212° C.; MS 396 (m+H); NMR 1.14(t,3H,J=7.4 Hz), 2.34(s,3H), 2.79(q,2H, J1=14.8 Hz,J2=7.4 Hz), 3.84(s,2H), 6.98(dd,1H, J1=8.1 Hz,J2=2 Hz), 7.09(d,1H,J=2 Hz), 7.19(d,2H,J=8.1 Hz), 7.28(d,2H,J=8.4 Hz), 7.38(d,2H,J=8.4 Hz), 8.99(s,1H); Analysis C21H18ClN3O5. 1.0 H2O expected/theoretical C 60.83/60.95H 4.72/4.87 N 10.08/10.15.

Example 181
7-Chloro-4-acetyloxy-2-(4'-methylphenyl)-5,10-dihydro-2H-pyridazino[4,5-b]quinoline-1-one.

A suspension of the 7-chloro-4-hydroxy-2-(4'-methylphenyl)-5,10-dihydro-2H-pyridazino[4,5-b] quinoline-1-one (755 mg), acetyl chloride (0.205 mL) and 2,6-lutidine (0.337 mL) was refluxed in toluene (6 mL) for 2 hours. The resulting mixture was cooled to room temperature. The resulting paste was diluted with ether (15 mL) and filtered in vacuo. The solids were washed with ether and ethyl acetate. The crude solids were triturated in warm ethyl acetate, then cooled to room temperature and filtered in vacuo. After drying this afforded the title compound as a light yellow solid (528 mg, 62%). mp 238–240° C.; MS 382 (m+H); NMR 2.34(s,3H), 2.41(s,3H), 3.85(s, 2H), 6.98(dd, 1H,J1=8.1,J2=1.9), 7.09(d,1H,J=1.9), 7.18(d,1H,J=8.1), 7.28(d,2H,J=8.3), 7.39(d,2H,J=8.3), 9.06(s,1H); Analysis C20H16ClN3O3. 0.03M H2O expected/theoretical C 62.09/ 62.04H 4.24/2.27 N 10.62/10.85.

Example 182
7-Chloro-4-carbomethoxypropionyloxy-2-(4'-methylphenyl)-5,10-dihydro-2H-pyridazino[4,5-b]quinoline-1-one.

The title compound was prepared by a procedure similar to that described in Example 181 but substituting carbomethoxypropionyl chloride for acetyl chloride. The title compound was obtained as an off white solid (755 mg, 76%). mp 220–222° C.; MS 454 (m+H); NMR 2.35(s,3H), 2.73(t,2H,J=6.6), 3.08(t,2H,J=6.6), 3.63(s,3H), 3.85(s,2H), 6.98(d,1H,J=8.1), 7.07(s,1H), 7.19(d,1H,J=8.1), 7.28(d,2H, J=8.2), 7.39(d,2H,J=8.2), 8.91(s,1H);

Analysis expected/theoretical C 60.85/60.80H 4.54/4.40 N 9.20/9.20.

Example 183
7-Chloro-4-hydroxy-2-(2'-methyl-4'-methoxyphenyl)-5,10-dihydro-2H-pyridazino[4,5-b]quinoline-1-one.

7-Chloro-4-hydroxy-2-(4-methoxy-2-methylphenyl)-1,2, 5,10-tetrahydropyridazino[4,5-b]quinoline-1,10-dione (5.0 mL, 13.1 mmol) was suspended in tetrahydrofuran (170 mL) under nitrogen cooled to 0° C. and treated with trifluoroacetic acid (18 mL, 235 mmol). Over a 10 minute period, the reaction mixture was then treated with NaBH$_4$ (1.973 g, 52.2 mmol). The reaction mixture was stirred at 0° C. for 6 hours and then was stored in a freezer overnight. The reaction mixture was then treated with additional NaBH$_4$ (approximately 1.0 g) and stirred at 0° C. for 2 hours. The reaction mixture was poured onto water (500 mL) and extracted with ethyl acetate (2×200 mL). The ethyl acetate extracts were combined and then concentrated in vacuo. The residue was poured onto ether (400 mL) and the solid which formed was collected by filtration to afford crude product. The crude was recrystallized from methanol to afford 1.91 g of the title compound as an off-white solid, mp 264–266° C.

Example 184

The following illustrate representative pharmaceutical dosage forms containing a compound of formula A or B, or a pharmaceutically acceptable salt thereof, for example as illustrated in Examples 145 etc., (hereinafter referred to as "compound X"), for therapeutic or prophylactic use in humans:

| (a) Tablet | mg/tablet |
| --- | --- |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |

| (b) Capsule | mg/capsule |
| --- | --- |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

Example 185

This is an example of a formulation suitable for parenteral use made with the compound of Example 145:

| Parenteral Formulation: | mg/mL |
| --- | --- |
| Compound | 10.0 |
| Meglumine | 19.5 |
| Dextrose, anhydrous | 39.5 |
| Sterile Water for Injection | qs ad 1 mL |

The solution was prepared by conventional measures well known in the pharmaceutical field. General formulations for this class of compounds and their salts, other than for acylated compounds, may be prepared by solubilizing the active compound in an aqueous meglumine (N-methylglucamine) solution containing an equimolar, or if solubilization is difficult, a molar excess of meglumine relative to Compound. Choline salts are preferred for use in making formulations. Excipients such has dextrose may be added to adjust the osmolality of the formulation. Water for Injection is added to bring the solution to final volume. Alternately, other amine bases such as tromethamine or 1-arginine may be used to solubilize the active compound.

Example 186

A formulation is made as in Example 185, except that the choline salt of Compound X is used in place of the compound of Example 145.

Example 187

A formulation is made comprising a 5% aqueous solution of dextrose made to 10 mg/mL in the choline salt of Compound X.

The previous examples are to be considered non-limiting and thus, the compounds of formula A, A', B, B', C or C' and pharmaceutical compositions containing the same may be used to treat and/or prevent stroke and other diseases as related herein. The following schemes and formulae are presented to clarify how to make the compounds of the invention.

Tables 1–8 relate to key precursors to compounds of the invention.

Table 9 shows compounds of the invention.

The formula pages describe the preparation of starting materials and key precursors to compounds of formula A and key intermediates which may be utilized to form compounds of formula A, B, C, A', B' or C'.

Schemes 1–7 describe how the starting materials were prepared while scheme 8 shows how compounds of the invention were or may be prepared.

TABLE 1

The following Examples were prepared according to previously described Examples (designated under Synthetic Procedures) using the corresponding acyl hydrazides as starting materials. The acyl hydrazides were prepared according to the proceddescribed in Example 41a) and Example 47c) for the 7-chloro- and 5,7-dichloro-substituted isomers, respectively. For the acyl hydrazide syntheses, the appropriate aryl hydrazines were employed in place of the 4-chloro-2-methylphenylhydrazine and 2,4-dimethylphenylhydrazine used in Examples 41a) and 47c, respectively.

| # | Name | Synthetic Procedures | Yield | m.p. | MS (CI) | NMR (DMSO-$d_6$) | Analysis (found/calculated) |
|---|---|---|---|---|---|---|---|
| 58 | 7-Chloro-1-hydroxy-3-(2-methylphenyl)-3,4,5,10-tetrahydropyridazino[4,5-b]quinoline-4,10-dione | Example 41 | 36 | 315–317 | 354(M+1) | 13.38(s, 1H, exchang.), 12.52(s, 1H, exchang.), 8.31(d, j=8.8Hz, 1H), 8.22(d, j=1.9HZ, 1H), 7.63(dd, j=1.9, 8.8Hz, 1H) 7.40(m, 4H), 2.16(s, 3H) | C=60.95/61.10 H=3.20/3.42 N=11.65/11.90 C18H12ClN3O3 |
| 59 | 7-Chloro-4-hydroxy-2-(2-methylphenyl)-1,2,5,10-tetrahydroxypyridazino[4,5-b]quinoline-1,10-dione | Example 42, using the filtrate obtained by filtration of the 3-aryl isomer via the procedure of Example 41. | 33 | 338–340 | 354(M+1) | 12.76(s, 1H, exchang.), 12.04(s, 1H, exchang.), 8.16(d, j=8.6Hz, 1H), 8.07(s, 1H), 7.45(d, j=8.6Hz, 1H), 7.33(m, 4H), 2.12(s, 3H) | C=60.86/61.10 H=3.20/3.42 N=11.55/11.90 C18H12ClN3O3 |
| 60 | 7-Chloro-3-(3,4-dimethoxyphenyl)-1-hydroxy-3,4,5,10-tetrahydropyridazino[4,5-b]-quinoline-4,10-dione | Example 41 | 16 | 367–369 | 400(M+1) | 13.34(s, 1H, exchang.), 12.46(br s, 1H, exchang.) 8.29(d, j=8.8Hz, 1H), 8.21(d, j=1.8Hz, 1H), 7.61(dd, j=1.8, 8.8Hz, 1H), 7.27(d, j=2.3Hz, 1H), 7.23(dd, j=2.3, 8.6Hz, 1H), 7.08(d, j=8.6Hz, 1H) 3.83(s, 3H), 3.78(s, 3H) | C=55.84/55.82 H=3.43/3.70 N=9.96/10.28 C19H14ClN3O5. 0.5H2O |
| 61 | 7-Chloro-2-(3,4-dimethylphenyl)-4-hydroxy-1,2,5,10-tetrahydropyridazino[4,5-b] quinoline-1,10-dione | Example 42, using the filtrate obtained by filtration of the 3-aryl isomer via the procedure of Example 41. | 75 | 344–347 | 368(M+1) | 12.73(s, 1H, exchang.), 12.00(s, 1H, exchang.), 8.16(d, j=8.7Hz, 1H), 8.05(d, j=1.5Hz, 1H), 7.45(dd, j=1.5, 8.7Hz, 1H), 7.30-7.20(m, 3H) 2.26(s, 6H) | C=61.53/61.45 H=3.99/3.91 N=11.20/11.31 C19H14ClN3O3. 0.2H2O |
| 62 | 7-Chloro-2-(2,4-dimethoxyphenyl)-4-hydroxy-1,2,5,10-tetrahydropyridazino[4,5-b]-quinoline-1,10-dione | Example 42, using the filtrate obtained by filtration of the 3-aryl | 56 | 307–309 | 400(M+1) | 12.63(br s, 1H, exchang.), 11.98(br s, 1H, exchang.), 8.15(d, j=8.7Hz, 1H), 8.06(s, 1H), 7.45(d, j=8.7Hz, 1H), 7.21(d, 8.6Hz, 1H), | C=52.39/52.36 H=3.78/4.16 N=9.53/9.64 C19H14ClN3O5. 2.0H2O |

TABLE 1-continued

The following Examples were prepared according to previously described Examples (designated under Synthetic Procedures) using the corresponding acyl hydrazides as starting materials. The acyl hydrazides were prepared according to the procedures described in Example 41a) and Example 47c) for the 7-chloro- and 5,7-dichloro-substituted isomers, respectively. For the acyl hydrazide syntheses, the appropriate aryl hydrazines were employed in place of the 4-chloro-2-methylphenylhydrazine and 2,4-dimethylphenylhydrazine used in Examples 41a) and 47c, respectively.

| # | Name | Synthetic Procedures | Yield | m.p. | MS (CI) | NMR (DMSO-$d_6$) | Analysis (found/calculated) |
|---|---|---|---|---|---|---|---|
| | | isomer via the procedure of Example 41. | | | | 6.69(d, j=2.4Hz, 1H), 6.59(dd, j=2.4, 8.6Hz, 1H), 3.82(s, 3H), 3.73(s, 3H) | |
| 63 | 7-Chloro-2-(2,5-dimethoxyphenyl)-4-hydroxy-1,2,5,10-tetrahydropyridazino[4,5-b]-quinoline-1,10-dione | Example 42, using the filtrate obtained by filtration of the 3-aryl isomer via the procedure of Example 41. | 53 | 237–239 | 400(M+1) | 12.60(br s, 1H, exchang.) 12.00(br s, 1H, exchang.) 8.16(d, j=8.7Hz, 1H), 8.06(d, j=2.0Hz, 1H), 7.46(dd, j=2.0, 8.7Hz, 1H), 7.09(d, j=9.0Hz, 1H), 6.99(dd, j=3.0, 9.0Hz, 1H) 6.96(d, j=3.0Hz, 1H), 3.73(s, 3H), 3.69(s, 3H) | C=51.38/51.08 H=3.76/4.00 N=9.07/9.26 C19H14ClN3O5. 1.4H2O. 0.3CH4SO3 |
| 64 | 7-Chloro-2-(2,5-dimethylphenyl)-4-hydroxy-1,2,5,10-tetrahydropyridazino[4,5-b]-quinoline-1,10-dione | Example 42, using the filtrate obtained by filtration of the 3-aryl isomer via the procedure of Example 41. | 47 | 330–332 | 368(M+1) | 12.71(s, 1H, exchang.), 12.02(s, 1H, exchang.), 8.15(d, j=8.6Hz, 1H), 8.06(s, 1H), 7.45(d, j=8.6Hz, 1H), 7.21(d, j=7.7Hz, 1H), 7.13(d, j=7.7Hz, 1H), 7.11(s, 1H), 2.30(s, 3H), 2.06(s, 3H) | C=61.89/62.05 H=3.95/3.84 N=11.35/11.43 C19H14ClN3O3 |
| 65 | 7-Chloro-2-(4-ethoxyphenyl)-4-hydroxy-1,2,5,10-tetrahydropyridazino[4,5-b]quinoline-1,10-dione | Example 42, using the filtrate obtained by filtration of the 3-aryl isomer via the procedure of Example 5. | 42 | 317–321 | 384(M+1) | 12.74(s, 1H, exchang.), 12.00(s, 1H, exchang.), 8.16(d, j=8.6Hz, 1H), 8.05(s, 1H), 7.45(d, j=8.6Hz 1H), 7.41(d, j=8.9Hz, 2H), 6.98(d, j=8.9Hz, 2H), 4.06(q, j=6.8Hz, 2H), 1.35(t, j=6.8Hz, 3H) | C=55.38/55.55 H=4.00/4.17 N=10.00/10.23 C19H14ClN3O4. 1.5H2O |
| 66 | 7-Chloro-2-(3-chlorophenyl)-4-hydroxy-1,2,5,10-tetrahydropyridazino[4,5-b]quinoline-1,10-dione | Example 42, using the filtrate obtained by filtration of the 3-aryl isomer via the procedure of Example 41 | 78 | 333 | 374(M+1) | 12.91(br s, 1H, exch.), 8.14(br m, 1H), 8.05(brs, 1H), 7.68-7.43(m, 5H) | C=48.40/48.53, H=2.88/2.95, N=9.79/9.76 $C_{17}H_9Cl_2O_3N_3$. 1.0 $H_2O$. 0.4 $CH_3SO_3H$ |
| 67 | 7-Chloro-4-hydroxy-2-(3-methylphenyl)-1,2,5,10-tetrahydropyridazino[4,5-b]quinoline-1,10-dione | Example 42, using the filtrate obtained by filtration of the 3-aryl isomer via the procedure of Example 41. | 77 | 343–346 | 354(M+1) | 12.77(br s, 1H, exch.), 8.16(d, J=8.61, 1H), 7.46(dd, J=1.95, 8.66, 1H), 7.35-7.33(m, 3H), 7.17(m, 1H), 2.36(s, 3H) | C=50.94/50.65, H=3.62/3.98, N=9.76/9.42 $C_{18}H_{12}ClN_3O_3$. 1.2 $H_2O$. 0.1 $CH_3OH$. 0.7 $CH_3SO_3H$ |
| 68 | 7-Chloro-4-hydroxy-2-(4-thiomethoxyphenyl)-1,2,5,10-tetrahydropyridazino[4,5-b]quinoline-1,10-dione | Example 42, using the filtrate obtained by filtration of the 3-aryl isomer via the procedure of Example 41. | 89 | 340–342 | 386(M+1) | 12.86(br s, 1H, exch.) 12.09(br s, 1H, exch.) 8.15(d, J=8.55, 1H) 8.05(s, 1H) 7.50-7.45(m, 3H) 7.31(d, J=8.34, 2H) | C=50.84/50.79 H=3.24/3.32 N=9.70/9.61 $C_{18}H_{12}ClN_3O_3S$. 0.2 $H_2O$. 0.5 $CH_3SO_3H$ |
| 69 | 7-Chloro-1-hydroxy-3-(4-thiomethoxyphenyl)-3,4,5,10-tetra- | Example 41 | 5 | 386 | 386(M+1) | 13.35(br s, 1H, exch.) 12.49(br s, 1H, exch.) | C=55.09/55.01 H=3.27/3.28 |

TABLE 1-continued

The following Examples were prepared according to previously described Examples (designated under Synthetic Procedures) using the corresponding acyl hydrazides as starting materials. The acyl hydrazides were prepared according to the procedures described in Example 41a) and Example 47c) for the 7-chloro- and 5,7-dichloro-substituted isomers, respectively. For the acyl hydrazide syntheses, the appropriate aryl hydrazines were employed in place of the 4-chloro-2-methylphenylhydrazine and 2,4-dimethylphenylhydrazine used in Examples 41a) and 47c, respectively.

| # | Name | Synthetic Procedures | Yield | m.p. | MS (CI) | NMR (DMSO-$d_6$) | Analysis (found/calculated) |
|---|---|---|---|---|---|---|---|
| | hydropyridazino[4,5-b]quinoline-4,10-dione | | | | | 8.28(d, J=8.76, 1H)<br>8.21(s, 1H)<br>7.65-7.59(m, 3H)<br>7.39(d, J=8.46, 2H)<br>2.53(s, 3H) | N=10.46/10.69<br>$C_{18}H_{12}ClN_3O_3S$.<br>0.4 $H_2O$ |
| 70 | 7-Chloro-2-(3-chloro-4-methylphenyl)-4-hydroxy-1,2,5,10-tetrahydropyridazino-[4,5-b]quinoline-1,10-dione | Example 42, using the filtrate obtained by filtration of the 3-aryl isomer via the procedure of Example 41. | 83 | 360–364 | 388(M+1) | 12.89(br s, 1H, exch.)<br>12.09(br s, 1H, exch.)<br>8.16(d, J=8.88, 1H)<br>8.06(s, 1H)<br>7.66(s, 1H)<br>7.47-7.43(m, 3H)<br>2.37(s, 3H) | C=50.91/50.73<br>H=3.25/3.13<br>N=9.62/9.65<br>$C_{18}H_{11}Cl_2N_3O_3$.<br>0.5 $H_2O$.<br>0.4 $CH_3SO_3H$ |
| 71 | 7-Chloro-3-(3-chloro-4-methylphenyl)-1-hydroxy-3,4,5,10-tetrahydropyridazino-[4,5-b]quinoline-4,10-dione | Example 41 | 6 | decomp. 398 | 388(M+1) | 12.48(br s, 1H, exch.)<br>8.32(d, J=8.61, 1H)<br>8.25(d, J=1.77, 1H)<br>7.80(d, J=2.04, 1H)<br>7.65-7.59(m, 2H)<br>7.49(d, J=8.34, 1H)<br>2.41(s, 3H) | C=54.92/54.68<br>H=3.04/3.01<br>N=10.52/10.63<br>$C_{18}H_{11}Cl_2N_3O_3$.<br>0.4 $H_2O$ |
| 72 | 7-Chloro-2-(2,3-dimethylphenyl)-4-hydroxy-1,2,5,10-tetrahydropyridazino[4,5-b]quinoline-1,10-dione | Example 42, using the filtrate obtained by filtration of the 3-aryl isomer via the procedure of Example 41. | 37[1] | 335–336 | 368(M+1) | 8.15(d, J=8.67, 1H)<br>8.09(d, J=1.93, 1H)<br>7.44(dd, J=2.0, 8.66, 1H)<br>7.17-7.07(m, 3H)<br>2.27(s, 3H)<br>1.95(s, 3H) | C=57.99/58.33<br>H=3.87/4.27<br>N=10.5/10.74<br>$C_{19}H_{14}ClN_3O_3$.<br>1.3 $H_2O$ |
| 73 | 7-Chloro-2-(4-ethylphenyl)-4-hydroxy-1,2,5,10-tetrahydropyridazino[4,5-b]quinoline-1,10-dione | Example 42, using the filtrate obtained by filtration of the 3-aryl isomer via the procedure of Example 41. | 65 | 319–320 | 369(M+1) | 12.76(br s, 1H, exch.)<br>12.02(br s, 1H, exch.)<br>8.16(d, J=8.67, 1H)<br>8.05(s, 1H)<br>7.46-7.42(m, 3H)<br>7.30(d, J=8.34, 2H)<br>2.69-2.62(m, 2H)<br>1.24-1.19(m, 3H) | C=58.79/58.60<br>H=3.94/4.24<br>N=10.81/10.79<br>$C_{19}H_{14}ClN_3O_3$.<br>1.2 $H_2O$ |
| 74 | 7-Chloro-2-(4-fluoro-2-methylphenyl)-4-hydroxy-1,2,5,10-tetrahydropyridazino[4,5-b]-quinoline-1,10-dione | Example 42, using the filtrate obtained by filtration of the 3-aryl isomer via the procedure of Example 41. | 45[2] | 361–363 | 372(M+1) | 12.80(br s, 1H, exch.)<br>12.05(br s, 1H, exch.)<br>8.16(d, J=8.67, 1H)<br>8.06(s, 1H)<br>7.46(d, J=8.58, 1H)<br>7.38-7.34(m, 1H)<br>7.23(dd, J=2.42, 9.58, 1H)<br>7.17-7.11(m, 1H)<br>2.12(s, 3H) | C=57.78/58.16<br>H=2.82/2.98<br>N=11.32/11.30<br>$C_{18}H_{11}ClN_3O_3F$ |
| 75 | 7-Chloro-2-(3,5-dimethoxyphenyl)-4-hydroxy-1,2,5,10-tetrahydropyridazino[4,5-b]-quinoline-1,10-dione | Example 42, using the filtrate obtained by filtration of the 3-aryl isomer via the procedure of Example 41. | 11[3] | 299–300 | 400(M+1) | 12.77(br s, 1H, exch,)<br>8.16(d, J=8.67, 1H)<br>8.05(d, J=1.86, 1H)<br>7.46(dd, J=1.97, 8.66, 1H)<br>6.73(d, J=2.19, 2H)<br>6.51(m, 1H)<br>3.76(s, 6H) | C=53.79/53.92<br>H=3.86/3.95<br>N=9.97/9.93<br>$C_{19}H_{14}ClN_3O_5$.<br>1.3 $H_2O$ |
| 76 | 7-Chloro-4-hydroxy-2-(2-isopropylphenyl)-1,2,5,10-tetrahydropyridazino[4,5-b]quinoline-1,10-dione | Example 42, using the filtrate obtained by filtration of the 3-aryl isomer via the proced- | 34[4] | 345–346 | 382(M+1) | 12.74(br s, 1H, exch.)<br>12.03(br s, 1H, exch.)<br>8.16(d, J=8.67, 1H)<br>8.07(d, J=1.59, 1H)<br>7.47-7.39(m, 3H)<br>7.33-7.23(m, 2H)<br>2.86-2.82(m, 1H)<br>1.53-1.09(m, 6H) | C=62.57/62.62<br>H=4.33/4.26<br>N=11.05/10.95<br>$C_{20}H_{16}ClN_3O_3$.<br>0.10 $H_2O$ |

TABLE 1-continued

The following Examples were prepared according to previously described Examples (designated under Synthetic Procedures) using the corresponding acyl hydrazides as starting materials. The acyl hydrazides were prepared according to the procedure described in Example 41a) and Example 47c) for the 7-chloro- and 5,7-dichloro-substituted isomers, respectively. For the acyl hydrazide syntheses, the appropriate aryl hydrazines were employed in place of the 4-chloro-2-methylphenylhydrazine and 2,4-dimethylphenylhydrazine used in Examples 41a) and 47c, respectively.

| # | Name | Synthetic Procedures | Yield | m.p. | MS (CI) | NMR (DMSO-$d_6$) | Analysis (found/calculated) |
|---|------|----------------------|-------|------|---------|-------------------|----------------------------|
| 80 | 7-Chloro-4-hydroxy-2-(4-iodophenyl)-1,2,5,10-tetrahydropyridazino[4,5-b]quinoline-1,10-dione | ure of Example 41. Example 42, using the filtrate obtained by filtration of the 3-aryl isomer via the procedure of Example 41. | 40 | >250 | 466(M+1) | 7.38(dd, J=8.6, 1.9Hz, 1H), 7.45(d, J=8.6Hz, 2H), 7.70(d, J=8.5Hz, 2H), 8.14(d, J=8.8Hz, 2H) | C17H9ClIN3O3. 1.0 HCl<br>C 40.58/40.67<br>H 2.01/2.01<br>N 8.09/8.37 |
| 81 | 7-chloro-2-(4-bromo-2-methoxyphenyl)-4-hydroxy-1,2,5,10-tetrahydropyridazino-[4,5-b]quinoline-1,10-dione | Example 42, using the filtrate obtained by filtration of the 3-aryl isomer via the procedure of Example 41. | 74 | >260 | 450(M+1) | 3.77(s, 3H), 7.23(m, 2H), 7.38(d, J=1.6Hz, 1H), 7.44(dd, J=8.7, 1.6Hz, 1H), 8.05(s, 1H), 8.13(d, J=8.7Hz, 1H), 12.03(bs, 1H), 12.77(bs, 1H) | C18H11ClBrN3O4. 0.6 CH3SO3H<br>C 44.04/44.12<br>H 2.48/2.67<br>N 8.47/8.30 |

[1] This compound was purified using flash chromatography over silica gel using 15% methanol in methylene chloride as the eluant.
[2] a) The cyclization of the appropriate acyl hydrazide was carried out as in Example 41 except at twice the stated concentration of acyl hydrazide.
b) This compound was purified using preperative HPLC according to the following procedure: Approximately 1 g of the crude N-2 and N-3 aryl isomeric mixture obtained from the cyclization of the appropriate acyl hydrazide according to the procedure outlined in Example 41 was dissolved in 1M aqueous choline hydroxide(4 mL) and the resulting solution diluted with methanol(4 mL). This solution was injected(10 mL injection loop) onto a Dynamax C# 60A column(41.4 mm × 25 cm) with a guard column(41.4 mm × 5 cm). The flow rate was 50 mL/min and the initial mobile phase was 40% methanol/buffer(buffer is 0.1% trifluoroacetic acid adjusted to pH 3 with triethylamine). Gradients of 40 to 60% methanol/buffer over 25 min and 60 to 100% over the next 10 min followed by a methanol (100%) flush(15 min) were used. The flow rate was increased to 70 mL/min during the methanol flush. Detection was done at 230 nm and the desired product eluted at 5 to 10 min in one large peak. The fraction containing the desired product was diluted with hydrochloric acid(1N) to pH 1 to give a suspension. This suspension was concentrated on a rotary evaporator to remove the methanol and the resulting suspension was filtered and the collected solids washed with water and air-dried to provide the desired 2-aryl isomer.
[3] This compound was purified using preperative HPLC according to the procedure in footnote 2 b).
[4] a) The cyclization of the appropriate acyl hydrazide was carried out as in Example 41 except at twice the stated concentration of acyl hydrazide.
b) This compound was purified using preperative HPLC according to the procedure in footnote 2 b).

TABLE 2

The following Examples were made generally as set forth in Example 35 using appropriate corresponding precursors to make the compounds listed.(Yield is from the acyl hydrazide)

| Ex. # | Name | Yield | m.p. (° C.) | MS (CI) | NMR (DMSO-$d_6$) | Analysis (cal'd/found) |
|-------|------|-------|-------------|---------|-------------------|------------------------|
| 85 | 7-chloro-2-(2-fluorophenyl)-4-hydroxy-1,2,5,10-tetrahydropyridazino[4,5-b]quinoline-1,10-dione | 13 | >250 | 358 (M+H) | 7.26–7.64(m, 5H), 8.07(s, 1H), 8.16(d, J=8.6Hz, 1H), 12.09(br s, 1H), 12.93(br s, 1H) | for $C_{17}H_9N_3O_3FCl.0.45H_2O$<br>C=55.81/55.84,<br>H=2.73/2.38,<br>N=11.49/11.23 |
| 86 | 7-chloro-2-(3,5-ditrifluoromethylphenyl)-4-hydroxy-1,2,5,10-tetrahydropyridazino-[4,5-b]quinoline-1,10-dione | 12 | >250 | 476 (M+H) | 7.48(dd, J=8.7, 2.0Hz, 1H), 8.02–8.13(m, 2H), 8.18(d, J=8.6Hz, 1H) 8.40(s, 2H), 12.20(br s, 1H), 13.13(br s, 1H) | for $C_{19}H_8N_3O_3F_6Cl$<br>C=47.25/47.35,<br>H=1.84/1.83,<br>N=8.70/8.70 |
| 87 | 7-chloro-2-(2,4-difluorophenyl)-4-hydroxy-1,2,5,10-tetrahydropyridazino[4,5-b]quinoline-1,10-dione | 32 | >250 | 376 (M+H) | 7.20–7.30(m, 1H), 7.45–7.56 (m, 2H), 7.58–7.70(m, 1H), 8.07 (s, 1H), 8.16(d, J=8.7Hz, 1H), | for $C_{17}H_8N_3O_3F_2Cl.0.50\ H_2O$<br>C=53.07/53.08,<br>H=2.36/2.37,<br>N=10.92/10.72 |
| 88 | 7-chloro-2-(2,5-difluorophenyl)-4-hydroxy-1,2,5,10-tetrahydropyridazino[4,5-b]quinoline-1,10-dione | 13 | >250 | 376 (M+H) | 7.31–7.56(m, 4H), 8.06(s, 1H), 8.16(d, J=8.7Hz, 1H), 12.12(br s, 1H), 13.00(br s, 1H) | for $C_{17}H_8N_3O_3F_2Cl$<br>C=54.35/54.14,<br>H=2.15/2.34,<br>N=11.18/11.19 |
| 89 | 7-chloro-4-hydroxy-2-(4-nitrophenyl)-1,2,5,10-tetrahydropyridazino[4,5-b]quinoline-1,10-dione | 25 | >250 | 385 (M+H) | 7.48(dd, J=8.7, 1.7Hz, 1H), 7.95–8.00(m, 2H), 8.06(d, J=1.8Hz, 1H), 8.17(d, J=8.7Hz, 1H), 8.32–8.41 (m, 2H), 12.16(br s, 1H), 13.15 (br s, 1H) | for $C_{17}H_9N_3O_3F_2Cl.0.085$ $CH_3SO_3H$<br>C=51.06/51.18,<br>H=2.59/2.58,<br>N=13.94/13.90 |

TABLE 2-continued

The following Examples were made generally as set forth in Example 35 using appropriate corresponding precursors to make the compounds listed.(Yield is from the acyl hydrazide)

| Ex. # | Name | Yield | m.p. (° C.) | MS (CI) | NMR (DMSO-$d_6$) | Analysis (cal'd/found) |
|---|---|---|---|---|---|---|
| 90 | 7-chloro-1-hydroxy-3-(4-trifluoromethylphenyl)-3,4,5,10-tetrahydropyridazino-[4,5-b]quinoline-4,10-dione | 12 | >250 | 408 (M+H) | 7.64(dd, J=8.8, 2.0Hz, 1H), 7.91–8.04(m, 4H), 8.24(d, J=1.9Hz, 1H), 8.32(d, J=8.8Hz, 1H), 12.61(br s, 1H), 13.45(br s, 1H) | for $C_{18}H_9N_3O_3F_3Cl.0.30\ H_2O$ C=52.33/52.39, H=2.34/2.36, N=10.17/9.91 |
| 91 | 7-chloro-4-hydroxy-2-(4-trifluoromethylphenyl)-1,2,5,10-tetrahydropyridazino-[4,5-b]quinoline-1,10-dione | 49 | >250 | 408 (M+H) | 7.48(dd, J=8.6, 2.0Hz, 1H), 7.86 (s, 4H), 8.07(d, J=2.0Hz, 1H), 8.17 (d, J=2.0Hz, 1H), 12.09(br s, 1H), 13.04(br s, 1H) | for $C_{18}H_9N_3O_3F_3Cl.0.35H_2O$ C=52.22/52.19, H=2.36/2.01, N=10.15/9.82 |
| 92 | 7-chloro-4-hydroxy-2-(3-nitrophenyl)-1,2,5,10-tetrahydropyridazino[4,5-b]quinoline-1,10-dione | 15 | >250 | 385 (M+H) | 7.46(dd, J=8.6, 1.8Hz, 1H), 7.70–7.79(m, 1H), 8.05(d, J=1.6Hz, 1H), 8.07–8.25(m, 3H), 8.49(s, 1H), 12.15(br s, 1H), 13.07(br s, 1H) | for $C_{18}H_9N_3O_3F_3Cl.0.40\ H_2O$ .0.30 $CH_3SO_3H$ C=49.38/49.54, H=2.63/2.35, N=13.31/12.98 |
| 93 | 7-chloro-1-hydroxy-3-(4-sulfonylmethylphenyl)-3,4,5,10-tetrahydropyridazino-[4,5-b]quinoline-4,10-dione | 12 | >250 | 418 (M+H) | 3.31(s, 3H), 7.64(dd, J=8.8, 1.9Hz, 1H), 8.01–8.1 1(m, 4H), 8.24 (d, J=1.7Hz, 1H), 8.31(d, J=8.8Hz, 1H), 12.61(br s, 1H), 13.47 (br s, 1H) | for $C_{18}H_{12}N_3O_5ClS.0.25\ H_2O$ C=51.19/51.20, H=2.98/2.75, N=9.95/10.01 |
| 94 | 7-chloro-4-hydroxy-2-(4-sulfonylmethylphenyl)-1,2,5,10-tetrahydropyridazino-[4,5-b]quinoline-1,10-dione | 48 | >250 | 418 (M+H) | 3.28(s, 3H), 7.47(dd, J=8.6, 2.0Hz, 1H), 7.90–7.93(m, 2H), 8.01–8.06 (m, 3H), 8.17(d, J=8.7Hz, 1H), 13.07(br s, 1H) | |

TABLE 3

The following Examples were made generally as set forth in Example 82, using appropriate corresponding precursors to make the compounds listed. (Yields are overall from the 3-carbomethoxy-2-pyrrolidinocarbamide-7-chloro-4-hydroxy quinoline)

| Ex. # | Name | Yield | m.p. (° C.) | MS (CI) | NMR (DMSO-$d_6$) | Analysis (cal'd/found) |
|---|---|---|---|---|---|---|
| 95 | 7-chloro-4-hydroxy-2-(pentafluorobenzyl)-1,2,5,10-tetrahydropyridazino[4,5-b]-quinoline-1,10-dione | 54% | >300 | 444(M+H) | 5.21(s, 2H), 7.43(dd, J=8.6, 1.6Hz, 1H), 8.01(d, J=1.6Hz, 1H), 8.13(d, J=8.6Hz, 1H) | for $C_{18}H_7N_3O_3F_5Cl$ C=48.72/48.40, H=1.59/1.82, N=9.47/9.28 |
| 96 | 7-chloro-2-(2-cyanobenzyl)-4-hydroxy-1,2,5,10-tetrahydro-pyridazino[4,5-b]quinoline-1,10-dione | 61 | >250 | 379(M+H) | 5.27(s, 2H), 7.36–7.52(m, 3H), 7.62–7.70(m, 1H), 7.87(dd, J=7.7, 1.0Hz, 1H), 8.04(d, J=1.8Hz, 1H), 8.15(d, J=8.7Hz, 1H), 12.00(br s, 1H), 12.75(br s, 1H) | for $C_{19}H_{11}N_4O_3Cl.0.30\ H_2O$ C=59.40/59.44, H=3.04/3.10, N=14.58/14.36 |
| 97 | 7-chloro-2-(3-chlorobenzyl)-4-hydroxy-1,2,5,10-tetrahydro-pyridazino[4,5-b]quinoline-1,10-dione | 77 | >250 | 388(M+H) | 5.11(s, 2H), 7.24–7.46(m, 5H), 8.03(s, 1H), 8.15(d, J=8.7Hz, 1H), 11.95(br s, 1H), 12.68(br s, 1H) | for $C_{18}H_{11}N_3O_3Cl$ C=55.69/55.68, H=2.86/3.03, N=10.82/10.59 |
| 98 | 7-chloro-2-(3,5-ditrifluoro-methylbenzyl)-4-hydroxy-1,2,4,10-tetrahydropyridazino-[4,5-b]quinoline-1,10-dione | 52 | >250 | 490(M+H) | 5.29(s, 2H), 7.43(dd, J=8.7, 1.9Hz, 1H), 8.00–8.08(m, 4H), 8.15(d, J=8.7Hz, 1H), 11.94(br s, 1H), 12.67(br s, 1H) | for $C_{20}H_{10}N_3O_3F_3Cl$ C=59.05/58.71, H=4.66/4.74, N=12.15/11.85 |
| 99 | 7-chloro-4-hydroxy-2-(3-phenylpropyl)-1,2,5,10-tetrahydropyridazino[4,5-b]-quinoline-1,10-dione | 57 | >250 | 382(M+H) | 1.92–2.06(m, 2H), 2.58–2.68(m, 2H), 3.88–3.98(m, 2H), 7.12–7.32 (m, 5H), 7.41(d, J=8.2Hz, 1H), 8.01 (s, 1H), 8.13(d, J=8.5Hz, 1H), 11.87 (br s, 1H), 12.53(br s, 1H) | for $C_{20}H_{16}N_3O_3Cl$ C=62.91/62.75, H=4.22/4.38, N=11.00/10.92 |
| 100 | 7-chloro-4-hydroxy-2-(4-methylbenzyl)-1,2,5,10-tetrahydropyridazino[4,5-b]-quinoline-1,10-dione | 72 | >250 | 368(M+H) | 2.27(s, 3H), 5.05(s, 2H), 7.08–7.22 (m, 4H), 7.43(d, J=8.7Hz, 1H), 8.02 (s, 1H), 8.14(d, J=8.7Hz, 1H), 11.92 (br s, 1H), 12.62(br s, 1H) | for $C_{19}H_{14}N_3O_3Cl$ C=62.05/61.86, H=3.84/4.00, N=11.42/11.34 |
| 101 | 7-chloro-4-hydroxy-2-(4-trifluoromethylbenzyl)-1,2,5,10-tetrahydropyridazino-[4,5-b]quinoline-1,10-dione | 60 | >250 | 422(M+H) | 5.19(s, 2H), 7.40–7.56(m, 3H), 7.70(d, J=8.1Hz, 2H), 8.03(s, 1H), 8.14(d, J=8.6Hz, 1H), 11.96(br s, 1H), 12.71(br s, 1H) | for $C_{19}H_{11}N_3O_3F_3Cl$ C=54.11/54.01, H=2.63/2.82, N=9.96/9.62 |
| 102 | 7-chloro-2-(4-cyanobenzyl)-4-hydroxy-1,2,5,10-tetrahydro-pyridazino[4,5-b]quinoline-1,10-dione | 43 | >250 | 379(M+H) | 5.18(s, 2H), 7.40–7.50(m, 3H), 7.80(d, J=8.2Hz, 2H), 8.03(s, 1H), 8.14(d, J=8.7Hz, 1H), 11.96(br s, 1H), 12.72(br s, 1H) | for $C_{19}H_{11}N_4O_3Cl.0.23\ H_2O$ C=59.60/59.57, H=3.02/3.10, N=14.63/14.85 |
| 103 | 7-chloro-2-(2-fluorobenzyl)-4-hydroxy-1,2,5,10-tetrahydro-pyridazino[4,5-b]quinoline-1,10-dione | 59 | >250 | 372(M+H) | 5.16(s, 2H), 7.12–7.40(m, 4H), 7.43(dd, J=8.6, 1.3Hz, 1H), 8.03 (s, 1H), 8.15(d, J=8.6Hz, 1H), 11.94 (br s, 1H), 12.66(br s, 1H) | for $C_{18}H_{11}N_3O_3FCl.0.50\ H_2O$ C=56.78/56.84, H=3.18/3.13, N=11.03/10.98 |

TABLE 4

The following Examples were made generally as set forth in Example 111, using appropriate corresponding precursors to make the compounds listed.

| Ex. # | Name | Yield | m.p. | MS (CI) | NMR (DMSO-$d_6$) | Analysis (calculated/found) |
|---|---|---|---|---|---|---|
| 116 | 7-Chloro-4-hydroxy-2-(succinimid-1-yl-ethyl)-1,2,5,10-tetrahydropyridazino[4,5-b]quinoline-1,10-dione | 77% | 359–363d | 389(M+1) | 2.57(s, 4H), 3.30(m, 2H), 4.02(m, 2H), 7.43(d, 1H, J=8.6Hz), 8.02(s, 1H), 8.13(d, 1H, J=8.7Hz), 11.91 (brs, 1H), 12.61(brs, 1H) | C=51.80/51.91, H=3.48/3.56, N=14.21/14.08 $C_{17}H_{13}N_4O_5Cl$ - 0.30$H_2O$ |
| 111 | 7-Chloro-4-hydroxy-2-(4,4-dimethyl-2,5-dioxooxazolidin-1-ylethyl)-1,2,5,10-tetrahydropyridazino[4,5-b]quinoline-1,10-dione | 67% | 350–351d | 419(M+1) | 1.42(s, 6H), 3.76(m, 2H), 4.13(m, 2H), 7.43(m, 2H, J=8.7Hz), 8.02(s, 1H), 8.13(d, 1H, J=8.8Hz), 11.9 (brs, 1H), 12.7(brs, 1H) | C=51.18/51.23, H=3.67/3.80, N=13.26/13.04 $C_{18}H_{15}N_4O_6Cl$ - 0.2$H_2O$ |
| 117 | 7-Chloro-4-hydroxy-2-(5-methyl-5-phenyl-2,4-dioxoimidazol-1-ylethyl)-1,2,5,10-tetrahydropyridazino[4,5-b]quinoline-1,10-dione | 54% | 165–170 | 480(M+1) | 1.61(s, 3H), 3.71(m, 2H), 4.13(m, 2H), 7.37(m, 5H), 7.44(dd, 1H, J1=8.7Hz, J2=1.95Hz), 8.02(d, 1H, J=2.0Hz), 8.15(d, 1H, J=8.7Hz), 8.84(s, 1H), 11.9(brs, 1H), 12.64(brs, 1H) | C=55.09/55.00, H=4.10/3.98 N=13.96/13.81 $C_{23}H_{18}N_5O_5Cl$ - 1.2$H_2O$ |
| 118 | 7-Chloro-4-hydroxy-2-(1-methyl-2,4-dioxoimidazo-3-ylethyl)-1,2,5,10-tetrahydropyridazino[4,5-b]quinoline-1,10-dione | 97% | >250C | 404(M+1) | 2.78(s, 3H), 3.69(t, 2H, J=5.6Hz), 3.89(s, 2H), 4.03(t, 2H, J=5.6Hz), 7.44(dd, 1H, J1=8.7Hz, J2=2.0Hz), 8.02(d, 1H, J=2.0Hz), 8.13(d, 1H, J=8.7Hz), 11.9(brs, 1H), 12.61(brs, 1H) | C=48.62/48.94, H=3.79/3.63, N=16.67/16.33 $C_{17}H_{14}N_5O_5Cl$ - 0.9$H_2O$ |
| 119 | 7-Chloro-4-hydroxy-2-(5,5-dimethyl-2,4-dioxoimidazo-3-ylethyl)-1,2,5,10-tetrahydropyridazino[4,5-b]quinoline-1,10-dione | 91% | >250C | 418(M+1) | 1.41(s, 6H), 3.76(m, 2H), 4.11(m, 2H), 7.43(d, 1H, J=8.6Hz), 8.02(s, 1H), 8.13(d, 1H, J=8.6Hz), 11.94 (brs, 1H), 12.71(brs, 1H) | C=50.87/50.97, H=3.98/4.05, N=16.48/16.14 $C_{18}H_{16}N_5O_5Cl$ - 0.4$H_2O$ |
| 120 | 7-Chloro-4-hydroxy-2-(imidazo-3-ylethyl) tetrahydropyridazino[4,5-b]quinoline-1,10-dione | 59% | >250C | 358(M+1) | 4.3(m, 2H), 4.60(m, 2H), 7.41(d, 1H, J=7.1Hz), 7.52(s, 1H), 7.75(s, 1H), 7.93(s, 1H), 8.06(d, 1H, J=8.7Hz), 9.18(s, 1H), 3.35(brs) | C=44.72/44.95, H=3.52/3.41, N=16.29/16.24 $C_{16}H_{12}N_5O_3Cl$ - 1.0 HCl - 1.0 $H_2O$ - 0.5 NaCl |
| 121 | 7-Chloro-4-hydroxy-2-(5,5-diphenyl-2,4-dioxoimidazo-3-ylethyl)-1,2,5,10-tetrahydropyridazino[4,5-b]quinoline-1,10-dione | 64% | 272–276 | 542(M+1) | 3.82(m, 2H), 4.16(m, 2H), 7.23(m, 10H), 7.44(d, 1H, J=8.7Hz), 8.03(s, 1H), 8.17(d, 1H, J=8.7Hz), 9.54(s, 1H), 11.89(s, 1H), 12.63(s, 1H) | C=59.87/59.90, H=3.98/3.81, 12.47/11.75 $C_{16}H_{11}ClN_4O_5S$ - 1.0$H_2O$ |
| 122 | 7-Chloro-4-hydroxy-2-(2,5-dioxothiazolidin-1-ylethyl)-1,2,5,10-tetrahydropyridazino[4,5-b]quinoline-1,10-dione | 77% | 323–326d | 407(M+1) | 3.82(m, 2H), 4.06(m, 2H), 4.12(s, 2H), 7.44(dd, 1H, J1=8.6Hz, J2=1.9Hz), 8.02(d, 1H, J=1.9Hz), 8.14(d, 1H, J=8.7Hz), 11.9(brs, 1H), 12.7(brs, 1H) | C=45.24/45.23, H=3.08/3.01, N=13.16/12.21 $C_{28}H_{20}N_5O_5Cl$ - 1.1$H_2O$ |
| 123 | 7-Chloro-4-hydroxy-2-(1,3-dioxopyridino[2,3-c]pyrrolidin-2-ylethyl-1,2,5,10-tetrahydropyridazino[4,5-b]quinoline-1,10-dione | 61% | 311–314 | 438(M+1) | 3.94(t, 2H, J=5.4Hz), 4.14(t, 2H, J=5.4Hz), 7.42(dd, 1H, J1=8.7Hz, J2=1.7Hz), 7.87(dd, 1H, J1=4.8Hz, J2=1.1Hz), 7.99(d, 1H, J=1.9Hz), 8.11(d, 2H, J=8.7Hz), 9.10(m, 2H), 11.89(brs, 1H), 12.53(brs, 1H) | C=52.70/52.75, H=3.10/2.82, N=15.36/15.43 $C_{10}H_{12}ClN_5O_5$ - 1.0$H_2O$ |
| 124 | 7-Chloro-4-hydroxy-2-(o-benzoicsulfimid-2-ylethyl)-1,2,5,10-tetrahydropyridazino[4,5-b]quinoline-1,10-dione | 59% | >250C | 473(M+1) | 4.04(t, 2H, J=5.46Hz), 4.27(t, 2H, J=5.43Hz), 7.18(dd, 1H, J1=8.7Hz, J2=1.56Hz), 8.03(m, 2H), 8.12(dd, 2H, J1=6.7Hz, J2=1.2Hz), 8.24(dd, 1H, J1=6.7Hz, J2=1.53Hz), 11.90 (brs, 1H), 12.59(brs, 1H) | C=48–94/49.27, H=3.08/3.48, N=11.41/11.09 $C_{20}H_{13}N_4O_6S_1Cl_1$ - 1.0$H_2O$ |
| 125 | 7-Chloro-4-hydroxy-2-(5,5-hexamethylene-2,5-dioxooxazolidin-1-ylethyl)-1,2-5,10-tetrahydropyridazino[4,5-b]quinoline-1,10-dione | 80% | >250C | 459(M+1) | 1.45(m, 10H), 3.76(m, 2H), 4.12(m, 2H), 7.44(d, 1H, J=8.6Hz), 8.02(s, 1H), 8.15(d, 1H, J=8.6Hz), 11.95(brs, 1H), 12.70(brs, 1H) | C=52.89/52.81, H=4.44/4.20, N=11.75/11.51 $C_{21}H_{19}N_4O_6Cl$ - 1.0$H_2O$ |
| 126 | 7-Chloro-hydroxy-2-(benzo[e][1,3]oxazinyl-2,4-dioneethyl)-1,2,5,10-tetrahydropyridazino[4,5-b]quinoline-1,10-dione | 92% | >250C | 453(M+1) | 4.23(m, 4H), 7.41(m, 3H), 7.78(m, 1H), 7.85(m, 1H), 7.99(m, 1H), 8.10(d, 1H, J=8.7Hz), 11.90(brs, 1H), 12.6(brs, 1H) | C=55.24/55.26, H=3.16/2.96, N=12.22/12.28 $C_{21}H_{13}ClN_4O_6$ - 0.2$H_2O$ |
| 127 | 7-Chloro-4-hydroxy-2-(1,2,4-triazol-2-yl ethyl)-1,2,5,10-tetrahydropyridazino[4,5-b]quinoline-1,10-dione | 70% | >250C | 359(M+1) | 4.23(t, 2H, J=5.65Hz), 4.54(t, 2H, J=5.66Hz), 7.40(dd, 1H, J1=8.7Hz, J2=1.9Hz), 7.93(s, 1H), 7.98(d, 1H, J=1.9Hz), 8.09(d, 1H, J=8.7Hz), 8.48(s, 1H), 11.9(brs, 1H), 12.6(brs, 1H) | C=49.31/49.58, H=3.12/3.35, N=22.40/22.38 $C_{15}H_{11}ClN_6O_3$ - 0.2NaCl |
| 128 | 7-Chloro-4-hydroxy-2-(1,2,3-triazol-2-yl ethyl)-1,2,5,10-tetrahydropyridazino[4,5-b]quinoline-1,10-dione | 75% | >250C | 359(M+1) | 4.32(m, 2H), 4.77(m, 2H), 7.45(m, 1H), 7.75(s, 1H), 8.01(m, 1H), 8.13(m,2H), 11.9(brs, 1H), 12.6(brs, 1H) | C=48.80/48.82, H=3.57/3.33, N=20.69/20.42 $C_{15}H_{11}ClN_6O_3$ - 0.7$H_2O$ |
| 129 | 7-Chloro-4-hydroxy-2-(1,2,3,4-tetrazol-1-ylethyl)-1,2,5,10-tetrahydropyridazino[4,5-b]quinoline-1,10-dione 7-Chloro-4-hydroxy-2-(1,2,3,4-tetrazol-2-ylethyl)-1,2,5,10-tetrahydropyridazino[4,5-b]quinoline-1,10-dione | 83% 1:1 mix of 2 isomers | >250C | 360(M+1) | 4.32(t, 1.5H, J=5.57Hz), 4.39(t, 1.5H, J=5.55Hz), 4.87(t, 1.5H, J=5.31Hz), 5.08(t, 1.5H, J=5.60Hz) 7.45(m, 1H), 8.01(m, 1H), 8.94(s, 0.5H), 9.47(s, 0.5H), 11.92(brs, 1H), 12.59(brs, 0.5H), 12.63(brs, 0.5H) | C=46.74/46.70, H=2.86/3.16, N=27.26/26.09 $C_{14}H_{10}ClN_7O_3$ - 0.5$H_2O$ |

TABLE 4-continued

The following Examples were made generally as set forth in Example 111, using appropriate corresponding precursors to make the compounds listed.

| Ex. # | Name | Yield | m.p. | MS (CI) | NMR (DMSO-d$_6$) | Analysis (calculated/found) |
|---|---|---|---|---|---|---|
| 130 | 7-Chloro-4-hydroxy-2-(5-phenyl-2,5-dioxooxazolidin-1-ylethyl)-1,2,5,10-tetrahydropyridazino[4,5-b]quinoline-1,10-dione | 74% | >250C | 467(M+1) | 3.80(m, 1.5H), 3.92(m, 1.5H), 4.00 (m, 1.5H), 4.38(m, 1.5H), 7.40(m, 6H), 8.00(s, 1H), 8.18(d, 1H, J=8.6Hz), 11.95(brs, 1H), 12.75(brs, 1H) | C=55.12/54.91, H=3.50/3.48, N=11.65/11.64 C$_{22}$H$_{15}$ClN$_4$O$_6$ - 0.2H$_2$O |

TABLE 5

The following Examples were made generally as set forth in Example 112, using appropriate corresponding precursors to make the compounds listed.

| Ex. # | Name | Yield | m.p. | MS (CI) | NMR (dmso-d6) | Analysis (calc./found) |
|---|---|---|---|---|---|---|
| 112 | 7-Chloro-4-hydroxy-2-(2-methyl-2-hydroxypropionamidoethyl)-1,2,5,10-tetrahydropyridazino[4,5-b]quinoline-1,10-dione | 84% | 300–303 | 392(M+1) | 1.18(s, 3H), 1.38(s, 3H), 3.4(m, 2H) 3.95(m, 2H), 7.26(m, 0.5H), 7.42(d, 1H, J=8.7Hz), 7.83(m, 0.5H), 8.01 (s, 1H), 8.13(d, 1H, J=8.6Hz), 11.9 (brs, 1H), 12.6(brs, 1H) | C=50.48/50.58, H=4.24/4.25, N=13.85/13.84 C$_{17}$H$_{17}$N$_4$O$_5$Cl - 0.2NaCl |
| 131 | 7-Chloro-hydroxy-2-(1-hydroxycyclo hexylcarboxamidoethyl)-1,2,5,10-tetrahydropyridazino[4,5-b]quinoline-1,10-dione | 81% | >250C | 433(M+1) | 1.50(m, 10H), 3.43(m, 2H), 3.98(m, 2H), 7.43(d, 1H, J=8.3Hz), 7.88(bt, 1H, J=5.8Hz), 8.01(s, 1H), 8.13(d, 1H, J=8.7Hz), 11.9(brs, 1H), 12.6(brs, 1H) | C=53.28/53.17, H=5.14/5.00, N=12.43/12.08 C$_{20}$H$_{21}$ClN$_4$O$_4$ - 1.0H$_2$O |
| 132 | 7-Chloro-4-hydroxy-2-(2-hydroxybenz amidoethyl)-1,2,5,10-tetrahydro pyridazino[4,5-b]quinoline-1,10-dione | 84% | >250C | 427(M+1) | 3.71(m, 2H), 4.11(m, 2H), 6.88(m, 2H), 7.39(m, 2H), 7.86(d, 1H, J=8.0Hz), 7.94(d, 1H, J=1.5Hz), 8.04(d, 1H, J=8.7Hz), 8.09(bt, 1H, J=5.6Hz) | C=54.44/54.37, H=3.79/3.73, N=12.70/12.63 C$_{20}$H$_{15}$ClN$_4$O$_5$ - 0.8H$_2$O |
| 133 | 7-Chloro-4-hydroxy-2-(2-hydroxy-2,2-diphenylacetamidoethyl)-1,2,5,10-tetrahydropyridazino[4,5-b]quinoline-1,10-dione | 66% | >250C | 517(M+1) | 3.50(m, 2H), 4.05(t, 2H, J=6.0Hz), 7.22(m, 6H), 7.36(m, 4H), 7.43(m, 1H), 8.05(d, 1H, J=1.42Hz), 8.15(d, 1H, J=8.6Hz), 8.26(bt, 1H), 11.90(brs, 1H), 12.68(brs, 1H) | C=62.73/59.69, H=4.09/3.95, N=10.84/11.11 C$_{27}$H$_{21}$ClN$_4$O$_5$ |
| 134 | 7-Chloro-4-hydroxy-2-(2-methyl-2-hydroxybutyramidoethyl)-1,2,5,10-tetrahydropyridazino[4,5-b]quinoline-1,10-dione | 76% | >250C | 407(M+1) | 0.70(t, 3H, J=7.35Hz), 1.17(s, 3H), 1.38(m, 1H), 1.56(m, 1H), 3.46(m, 2H), 3.98(m, 2H), 7.42(d, 1H, J=7.95Hz), 7.82(bt, 1H, J=5.6Hz), 8.00(d, 1H, J=8.6Hz), 11.87(brs, 1H), 12.57(brs, 1H) | C=51.66/51.89, H=4.57/4.62, N=13.39/13.31 C$_{18}$H$_{19}$ClN$_4$O$_5$ - 0.2NaCl |

TABLE 6

The following Examples were made generally as set forth in Example 113, using appropriate corresponding precursors to make the compounds listed.

| Ex. # | Name | Yield | m.p. | MS (CI) | NMR (DMSO-d$_6$) | Analysis (calculated/found) |
|---|---|---|---|---|---|---|
| 113 | 7-Chloro-4-hydroxy-2-(2-methylthio ethyl)-1,2,5,10-tetrahydropyridazino [4,5-b]quinoline-1,10-dione | 85% | 282–284 | 338(M+1) | 2.11(s, 3H), 2.79(t, 2H, J=7.1Hz), 4.08(t, 2H, J=7.1Hz), 7.42(d, 1H, J=7.8Hz), 8.01(s, 1H), 8.13(d, 1H, J=8.6Hz), 11.91(brs, 1H), 12.64(brs, 1H) | C=49.78/49.73, H=3.58/3.73, N=12.44/12.30 C$_{14}$H$_{12}$ClN$_3$O$_3$S$_1$ |
| 135 | 7-Chloro-4-hydroxy-2-(2-ethylthio ethyl)-1,2,5,10-tetrahydropyridazino [4,5-b]quinoline-1,10-dione | 53% | 264–266 | 352(M+1) | 1.20(t, 3H, J=7.35Hz), 2.56(q, 2H, J=7.38Hz), 2.82(t, 2H, J=7.26Hz), 4.06(t, 2H, J=7.31Hz), 7.43(dd, 1H, J1=8.64Hz, J2=1.95Hz), 8.02(d, 1H, J=1.98Hz), 8.13(d, 1H, J=8.61Hz), 11.9(brs, 1H), 12.6(brs, 1H) | C=51.07/51.21, H=4.04/4.01, N=11.99/11.94 C$_{15}$H$_{14}$ClN$_3$O$_3$S |
| 136 | 7-Chloro-4-hydroxy-2-(2-n-butylthio ethyl)-1,2,5,10-tetrahydropyridazino [4,5-b]quinoline-1,10-dione | 75% | 248–250 | 380(M+1) | 0.88(t, 3H, J=7.3Hz), 1.36(m, 2H), 2.52(m, 2H), 2.80(t, 2H, J=7.2Hz), 4.06(t, 2H, J=7.2Hz), 7.42(m, 1H), 8.02(s, 1H), 8.13(d, 1H, J=8.6Hz), 11.92(brs, 1H), 12.63(brs, 1H) | C=53.45/53.43, H=4.78/4.95, N=11.06/11.21 C$_{17}$H$_{18}$ClN$_3$O$_3$S |
| 137 | 7-Chloro-hydroxy-2-(2-n-propylthio ethyl)-1,2,5,10-tetrahydropyridazino [4,5-b]quinoline-1,10-dione | 78% | 265–268 | 366(M+1) | 0.94(t, 3H, J=7.3Hz), 1.55(sx, 2H, J=7.3Hz), 2.53(m, 2H), 2.80(t, 2H, J=7.3Hz), 4.05(t, 2H, J=7.3Hz), | C=52.21/52.53, H=4.53/4.41, N=11.80/11.49 C$_{16}$H$_{10}$ClN$_3$O$_4$ - 0.2H$_2$O |

TABLE 6-continued

The following Examples were made generally as set forth in Example 113, using appropriate corresponding precursors to make the compounds listed.

| Ex. # | Name | Yield | m.p. | MS (CI) | NMR (DMSO-$d_6$) | Analysis (calculated/found) |
|---|---|---|---|---|---|---|
| | | | | | 7.42(dd, 1H, J1=8.6Hz, J2=1.8Hz), 8.02(d, 1H, J=1.9Hz), 8.13(d, 1H, J=8.7Hz), 11.9(brs, 1H) | |

TABLE 7

The following Examples were made generally as set forth in Example 114, using appropriate corresponding precursors to make the compounds listed.

| Ex. # | Name | Yield | m.p. | MS (CI) | NMR (DMSO-$d_6$) | Analysis (calculated/found) |
|---|---|---|---|---|---|---|
| 114 | 7-Chloro-4-hydroxy-2-(2-methylsulfonyl ethyl)-1,2,5,10-tetrahydropyridazino [4,5-b]quinoline-1,10-dione | 75% | >250C | 370(M+1) | 2.51(s, 3H), 3.53(t, 2H, J=6.9Hz), 4.31(m, 2H), 7.43(dd, 1H, J1=8.6Hz, J2=1.2Hz), 8.02(d, 1H, J=1.5Hz), 8.14(d, 1H, J=8.6Hz), 12.5(brs, 2H) | C=43.36/43.33, H=3.64/3.64, N=10.84/10.57 $C_{14}H_{12}ClN_3O_5S_1$ - 1.0$H_2O$ |
| 138 | 7-Chloro-4-hydroxy-2-(2-ethylsulfonyl ethyl)-1,2,5,10-tetrahydropyridazino [4,5-b]quinoline-1,10-dione | 89% | 270–274 | 384(M+1) | 1.22(m, 3H), 3.18(m, 2H), 3.49(t, 2H, J=7.13Hz), 4.30(t, 2H, J=7.16Hz), 7.44(dd, 1H, J1=8.7Hz, J2=1.9Hz), 8.02(d, 1H, J=1.9Hz), 8.13(d, 1H, J=8.7Hz), 11.9(brs, 1H), 12.7(brs, 1H) | C=44.84/44.71, H=4.01/4.02, N=10.46/10.44 $C_{15}H_{14}ClN_3O_5S_1$ - 1.0$H_2O$ |
| 139 | 7-Chloro-4-hydroxy-2-n-butylsulfonyl ethyl)-1,2,5,10-tetrahydropyridazino [4,5-b]quinoline-1,10-dione | 100% | 288–290 | 412(M+1) | 0.89(t, 3H, J=7.26Hz), 1.39(m, 2H), 1.63(m, 2H), 3.17(m, 2H), 3.50(t, 2H, J=6.96Hz), 4.30(t, 2H, J=6.99Hz), 7.44(d, 1H, J=8.8Hz), 8.02(s, 1H), 8.13(d, 1H, J=8.6Hz), 11.97(brs, 1H), 12.79(brs, 1H) | C=47.50/47.14, H=4.69/4.68, N=9.77/9.71 $C_{17}H_{18}ClN_3O_5S$ - 1.0$H_2O$ |

TABLE 8

The following Examples were made generally as set forth in Example 115, using appropriate corresponding precursors to make the compounds listed.

| Ex. # | Name | Yield | m.p. | MS (CI) | NMR (DMSO-$d_6$) | Analysis (calc./found) |
|---|---|---|---|---|---|---|
| 115 | 7-Chloro-4-hydroxy-2-(thiophen-2-yl methyl)-1,2,5,10-tetrahydropyridazino [4,5-b]quinoline-1,10-dione | 84% | >250 C. | 360 (M + 1) | 5.23(s, 2H), 6.98(m, 1H), 7.10(m, 1H), 7.43(m, 2H), 8.02(d, 1H, J=1.95Hz), 8.14(d, 1H, J=8.7Hz), 11.92(brs, 1H), 12.7(brs, 1H) | C = 52.11/52.10, H = 3.01/3.32, N = 11.39/11.10 $C_{16}H_{10}ClN_3O_2S$-0.5$H_2O$ |
| 140 | 7-Chloro-4-hydroxy-2-(furan-2-yl methyl)-1,2,5,10-tetrahydropyridazino [4,5-b]quinoline-1,10-dione | 51% | >250 C. | 344 (M + 1) | 5.09(s, 2H), 6.36(d, 1H, J=3.1Hz), 6.42(m, 1H), 7.42(m, 1H), 7.59(d, 1H, J=1.0Hz), 8.02(d, 1H, J=1.9Hz), 8.14(d, 1H, J=8.7Hz), 11.9 (brs, 1H), 12.7(brs, 1H) | C = 55.46/55.33, H = 3.12/3.02, N = 11.39/11.10 $C_{16}H_{10}ClN_3O_4$-0.2$H_2O$ |
| 141 | 7-Chloro-4-hydroxy-2-(thiophene-3-yl methyl)-1,2,5,10-tetrahydropyridazino [4,5-b]quinoline-1,10-dione | 65% | >250 C. | 360 (M + 1) | 5.08(s, 1H), 7.08(d, 1H, J=4.86Hz), 7.37(s, 1H), 7.43(d, 1H, J=8.6Hz), 7.50(m, 1H), 8.02(s, 1H), 8.14(d, 1H, J=8.6Hz), 11.92(brs, 1H), 12.65(brs, 1H) | C = 52.88/52.91, H = 2.88/3.12, N = 11.56/11.35 $C_{16}H_{10}ClN_3O_3S$-0.2$H_2O$ |
| 142 | 7-Chloro-4-hydroxy-2-(furan-3-yl methyl)-1,2,5,10-tetrahydropyridazino [4,5-b]quinoline-1,10-dione | 59% | >250 C. | 344 (M + 1) | 4.92(s, 1H), 6.46(s, 1H), 7.43(d, 1H, J=8.46Hz), 7.63(m, 1H), 8.02(d, 1H, J=1.6), 8.14(d, 1H, J=8.61Hz), 11.92(brs, 1H), 12.67(brs, 1H) | C = 55.91/55.58, H = 4.01/4.03, N = 12.22/11.89 $C_{16}H_{14}ClN_3O_4$ |
| 143 | 7-Chloro-4-hydroxy-2-(3-methylthio propyl)-1,2,5,10-tetrahydropyridazino [4,5-b]quinoline-1,10-dione | 64% | 263–265 C. (decomp) | 352 (M + 1) | 1.93(p, 2H, J=5.37Hz), 3.33(m, 1H, [superimposed on water peak]), 7.41(d, 1H, J=8.64Hz), 8.01(s, 1H), 8.12(d, 1H, J=8.73Hz), 11.88(brs, 1H), 12.58(brs, 1H) | C = 51.21/50.98, H = 4.01/4.13, N = 11.94/11.89 $C_{15}H_{14}ClN_3O_3S$ |

TABLE 8-continued

The following Examples were made generally as set forth in Example 115, using appropriate corresponding precursors to make the compounds listed.

| Ex. # | Name | Yield | m.p. | MS (CI) | NMR (DMSO-d$_6$) | Analysis (calc./found) |
|---|---|---|---|---|---|---|
| 144 | 7-Chloro-4-hydroxy-2-(2-cyanoethyl)-1,2,5,10-tetrahydropyridazino[4,5-b]quinoline-1,10-dione | 55% | >250 C. | 317 (M + 1) | 2.96(t, 2H, J=6.4Hz), 4.14(t, 2H, 6.42Hz), 7.43(dd, 1H, J1=8.69Hz, J2= 1.18Hz), 8.03(d, 1H, J=1.68Hz), 8.13(d, 1H, J=8.64Hz), 11.98(brs, 1H), 12.81(brs, 1H) | C = 51.91/52.16, H = 3.05/3.03, N = 17.30/17.18 C$_{14}$H$_9$ClN$_4$O$_3$-0.4H$_2$O |

TABLE 9

The following examples were prepared according to the procedure described in Example 145 using similar reagents and conditions from the appropriate precursor, the preparation of which is described in Examples 1–144.

| Ex | Name | yld | m.p. (° C.) | NMR (d6-DMSO) | MS (CI) | Analysis (exp.theory) |
|---|---|---|---|---|---|---|
| 146 | 7,9-dichloro-2,3,5,10-tetrahydropyridazino[4,5-b]quinoline-1,4-dione | 74% | >260 | 3.72(s, 2H), 7.04(d, 1H, JH=1.9Hz), 7.17 (d, 1H, J=1.9Hz), 9.15(s, 1H) | 284 | C11H7Cl2N3O2.0.25H2O. 2CF3CO2H C 43.95/43.97 H 2.55/2.59 N 13.76/13.50 |
| 147 | 7-chloro-4-hydroxy-2-phenyl-5,10-dihydro-2H-pyridazino [4,5-b]quinolin-1-one | 17% | 234–236 (dec) | 3.81(s, 2H), 6.94(s, 1H, J=8.2Hz), 7.14 (d, 1H, J=8.2Hz), 7.22(s, 1H), 7.31 (m, 1H), 7.43(m, 2H), 7.54 (d, 2H, J=7.9Hz) | 326 | C17H12ClN3O2 C 62.68/62.37 H 3.71/3.86 N 12.89/12.66 |
| 148 | 7-chloro-4-hydroxy-2-(4'-methoxyphenyl)-5,10-dihydro-2H-pyridazino[4,5-b]quinoline-1-one | 70% | 244–245 (dec) | 3.78(app s, 5H), 6.93(m, 3H), 7.14 (d, 1H, J=8.3Hz), 7.21(s, 1H), 7.45 (dd, 2H, J1=8.8, J2=0.9), 9.04(s, 1H), 11.97(s, 1H) | 356 | C18H14ClN3O3.0.5H2O. 0.3C4H8O2 C 58.89/58.95 H 4.33/4.48 N 12.89/12.66 |
| 149 | 7-chloro-2,3,5,10-tetrahydropyridazino[4,5-b]quinoline-1,4-dione | 17% | >265 | 3.77(s, 2H), 6.88(dd, 1H, J1=8.1, J2=1.9), 7.09(d, 1H, J=8.1), 7.19D, 1H, J=1.9), 9.06(s, 1H) | 248 | C11H8ClN3O2.0.45H2O C 51.30/51.26 H 3.32/3.48 N 16.16/16.30 |
| 150 | 7,9-dichloro-4-hydroxy-2-(4'-methylphenyl)-5,10-dihydro-2H-pyridazino[4,5-b]quinoline-1-one | 74% | 248–250 (dec) | 2.34(s, 3H), 3.75(s, 2H), 7.10 (d, 1H, J=2.0), 7.18(d, 1H, J=2.0), 7.24 (d, 2H, J=8.3), 7.43(d, 2H J=8.3), 9.24 (s, 1H), 12.09(s, 1H) | 374 | C18H13Cl2N3O2.0.2CF3CO2H .3H2O C 54.92/54.83 H 3.46/3.54 N 10.44/10.37 |
| 151 | 7-chloro-4-hydroxy-2-hydoxyethyl-5,10-dihydro-2H-pyridazino[4,5-b]quinoline-1-one | 16% | 214–216 (dec) | 3.61(t, 2H, J=6.2), 3.74(s, 2H), 3.87 (t, 2H, J=6.2), 4.77(s, 1H), 6.88 (d, 1H, J=7.9), 7.09(d, 1H, J=7.9), 8.84 (s, 1H), 11.74(s, 1H) | 294 | C13H12ClN3O3.0.36CF3CO2H.0.2H2O C 48.48/48.70 H 3.86/3.80 N 12.65/12.42 |
| 152 | 7-chloro-4-hydroxy-2-(N-ethyl-4'-methoxyaniline)-5,10-dihydro-2H-pyridazino[4,5-b]quinoine-1-one | 9% | 200–202 (dec) | 3.26(m, 2H), 3.62(s, 3H), 3.76(s, 2H), 3.96(m, 2H), 6.60(d, 2H, J=8.8), 6.73 (d, 2H, J=8.8), 6.90 (dd, 1H, J1=8.2, J2=1.9), 7.10 (d, 1H, J=8.2), 7.17(d, 1H, J=1.9), 8.91 (s, 1H), 11.79(s, 1H) | 399 | C20H19ClN4O3. 1CF3CO2H.0.7H2O C 50.11/50.29 H 3.92/4.10 N 10.56/10.66 |
| 153 | 7-chloro-4-hydroxy-2-(4'-fluorophenyl)-5,10-dihydro-2H-pyrdiazino[4,5-b]quinoline-1-one | 32% | 260–262 (dec) | 3.80(s, 2H), 6.94(d, 1H, J=8.2), 7.14 (d, 1H, J=7.6), 7.23(m, 3H), 7.58(m, 2H), 9.10(s, 1H), 12.09(bs, 1H) | 343 | C17H11ClFN3O2.0.3 CF3CO2H C 55.89/55.93 H 3.36/3.01 N 11.21/11.12 |
| 154 | 7-chloro-4-hydroxy-2-(4'-methoxy-dimethoxyphenyl)-5,10-dihydro-2H-pyridazino[4,5-b]quinoline-1-one | 16% | 205–207 (dec) | 3.80(s, 2H), 3.88(s, 3H), 6.91(m, 2H), 7.14(d, 1H, J=8.2), 7.22(s, 1H), 7.86 (dd, 1H, J1=8.6, J2=2.6)8.34 (d, 1H, J=2.6), 9.11(s, 1H), 2.13(bs, 1H) | 357 | C17H13ClN4O3.1H2O. 0.9CF3CO2 C 47.22/47.29 H 3.17/3.36 N 11.90/11.74 |
| 155 | 7-chloro-4-hydroxy-2-(3',4'-dimethoxyphenyl)-5,10-dihydro-2H-pyridazino[4,5-b]quinoline-1-one | 27% | 248–250 (dec) | 3.74(s, 2H), 3.79(app s, 6H), 6.99 (m, 3H), 7.11(d, 2H, J=6.7), 7.21(s, 1H), 9.05(s, 1H), 11.99(bs, 1H) | 386 | C19H16ClN3O4.07H2O. 0.2CF3CO2H C 55.36/55.32 H 4.42/4.21 N 9.70/9.97 |
| 156 | 7-chloro-4-hydroxy-2-(2',4'-dimethylphenyl)-5,10-dihydro-2H-pyridazino[4,5-b]quinoline-1-one | 72% | 212–214 (dec) | 2.03(s, 3H), 2.31(s, 3H), 3.79(s, 2H), 6.93(dd, 1H, J1=7.0, J2=2.0), 7.10 (m, 4H), 7.22(d, 1H, J=2.0), 9.03(s, 1H), 11.93(s, 1H) | 354 | C19H16ClN3O2.03H2O C 63.46/63.53 H 4.44/4.65 N 11.88/11.69 |

TABLE 9-continued

The following examples were prepared according to the procedure described in Example 145 using similar reagents and conditions from the appropriate precursor, the preparation of which is described in Examples 1–144.

| Ex | Name | yld | m.p. (° C.) | NMR (d6-DMSO) | MS (CI) | Analysis (exp.theory) |
|---|---|---|---|---|---|---|
| 157 | 7-chloro-4-hydroxy-2-(3'-methoxyphenyl)-5,10-dihydro-2H-pyridazino[4,5-bp9 quinoline-1-one | 36% | 235–237 (dec) | 3.84(s, 3H), 3.88(s, 2H), 6.99(m, 2H), 7.22(m, 3H), 7.29(d, 1H, J=2.0), 7.40 (m, 1H), 9.16(s, 1H), 12.12(bs, 1H) | 356 | C18H13ClN3O3.0.25H2O C 60.16/60.01 H 4.14/4.06 N 11.43/11.66 |
| 158 | 7-chloro-4-hydroxy-2-(4'-bromo-2'-methoxyphenyl)-5,10-dihydro-2H-pyridazino[4,5-b]quinoline-1-one | 73% | 230–232 (dec) | 3.76(app s, 5H), 6.91(dd, 1H, J1=8.2, J2=2.1), 7.10(d, 1H, J=8.2), 7.22 (m, 3H), 7.35(d, 1H, J=1.4), 9.03(s, 1H), 11.96(s, 1H) | 434 | C18H13ClBrN3O3.2H2O. 0.5CF3CO2H C 43.23/43.24 H 3.47/3.34 N 8.05/7.96 |
| 159 | 7-chloro-4-hydroxy-2-(ethyl thioethyl)-5,10-dihydro-2H-pyridazino[4,5-b]quinoline-1-one | 90% | 221–223 (dec) | 1.18(app t, 3H), 2.53(m, 2H), 2.77 (t, 2H, J=7.3), 3.75(s, 2H), 3.98 (t, 2H, J=7.3), 6.89(dd, 1H, J1=8.2, J2= 2.0), 7.10(d, 1H, J=8.2), 7.18(d, 1H, J= 2.0), 8.92(s, 1H), 11.82(s, 1H) | 338 | C15H16ClN3O2S.03H2O C 52.40/52.49 H 4.69/4.87 N 12.15/12.24 |
| 160 | 7-chloro-4-hydroxy-2-(2',5'-dimethylphenyl)-5,10-dihydro-2H-pyridazino[4,5-b]quinoline-1-one | 90% | 236–238 (dec) | 2.02(s, 3H), 2.28(s, 3H), 3.80(s, 2H), 6.93 (dd, 1H, J1=8.1, J2=2.1) 7.05(s, 1H), 7.11(d, 2H, J=7.7), 7.20(m, 2H), 9.04(s, 1H), 11.92(s, 1H) | 354 | C19H16ClN3O2.0.2H2O C 63.86/63.85 H 4.64/4.62 N 11.62/11.76 |
| 161 | 7,9-dichloro-4-hydroxy-2-(4'-methoxyphenyl)-5,10-dihydro-2H-pyridazino[4,5-b]quinoline-1-one | 49% | 226–228 (dec) | 3.78(app d, 5H), 6.99(d, 2H, J=8.9), 7.10 (d, 1H, J=1.9), 7.18(d, 1H, J=1.9), 7.45 (d, 2H, J=8.9), 9.22(s, 1H) | 390 | C18H13ClN3O3. 0.7CF3CO2H.1.3H2O H 3.29/3.21 N 8.52/8.85 |
| 162 | 7-chloro-4-hydroxy-2-(4'-methylbenzyl)-5,10-dihydro-2H-pyridazino[4,5-b]quinoline-1-one | 67% | >260 | 2.26(s, 3H), 3.78(s, 2H), 4.98(s, 2H), 6.91 (dd, 1H, J1=8.1, J2=2.0) 7.12(m, 5H), 7.18(d, 1H, J=2.0), 8..93(s, 1H), 11.80 (bs, 1H) | 354 | C19H16ClN3O2.0.2H2O C 63.83/63.85 H 4.65/4.62 N 11.79/11.76 |
| 163 | 7,9-dichloro-4-hydroxy-2-(2',4'-dimethylphenyl)-5,10-dihydro-2H-pyridazino[4,5-b]quinoline-1-one | 42% | 247–249 (dec) | 2.03(s, 3H), 2.30(s, 3H), 3.75(s, 2H), 7.10 (m, 4H), 7.19(d, 1H, J=1.9), 9.21(s, 1H). 12.03(bs, 1H) | 388 | C19H15Cl2N3O2. 0.6CF3CO2H C 53.18/53.13 H 3.76/3.44 N 9.48/9.20 |
| 164 | 7-chloro-4-hydroxy-2-(4'-bromo-2'-methylphenyl)-5,10-dihydro-2H-pyridazino[4,5-b]quinoline-1-one | 76% | 237–239 (dec) | 2.08(s, 3H), 4.80(s, 2H), 6.91 (d, 1H, J=8.2), 7.13(d, 1H, J=8.2), 7.23(app d, 2H), 7.45(d, 1H, J=8.4), 7.57s, 1H), .07(s, 1H), 12.03 (s, 1H) | 420 | C18H13ClBrN2O2. 0.8C4H10O.0.5H2O C 52.20/52.29 H 4.32/4.55 N 8.70/8.63 |
| 165 | 7-chloro-4-hydroxy-2-(2'-fluorobenzyl)-5,10-dihydro-2H-pyridazino[4,5-b]quinoline-1-one | 90% | 233–235 (dec) | 3.79(s, 2H), 5.10(s, 2H), 6.92 (dd, 1H, J1=8.1, J2=2.0), 7.16(m, 5H), 7.31(m, 1H), 8.98(s, 1H), 11.89 (bs, 1H) | 358 | C18H13ClFN3O2. 0.3CF3CO2H0.3H2O C 56.18/56.22 H 3.63/3.53 N 10.72/10.57 |
| 166 | 7-chloro-4-hydroxy-2-(3'-benzyl)-5,10-dihydro-2H-pyridazino[4,5-b]quinoline-1-one | 69% | 218–220 (dec) | 3.79(s, 2H), 5.04(s, 2H), 6.91 (dd, 1H, J1=8.1, J2=2.0), 7.11 (d, 1H, J=8.1), 7.21(m, 2H), 7.34 (m, 3H), 8.97(s, 1H), 11.85(bs, 1H) | 374 | C18H13Cl2N3O2.0.5H2O C 56.54/56.41 H 3.59/3.68 N 10.95/10.96 |
| 167 | 7-chloro-4-hydroxy-2-(2'-cyano benzyl)-5,10-dihydro-2H-pyridazino[4,5-b]quinoline-1-one | 60% | 258–260 (dec) | 3.79(s, 2H), 5.23(s, 2H), 6.90 (dd, 1H, J1=8.1, J2=1.1), 7.12 (d, 1H, J=8.1), 7.20(d, 1H, J=1.1), 7.27(d, 1H, J=7.8), 7.48(m, 1H), 7.66 (m, 1H), 7.86(d, 1H, J=7.7), 9.02 (s, 1H), 11.94(s, 1H) | 365 | C19H13ClN4O2.0.15H2O C 62.07/62.09 H 3.75/3.65 N 15.06/15.24 |
| 168 | 7-chloro-4-hydroxy-2-(3'-phenoxyphenyl)-5,10-dihydro-2H-pyridazino[4,5-b]quinoline-1-one | 94% | ND | 3.78(s, 1H), 6.90–7.21(m, 9H), 7.38–7.47(m, 3H), 9.10(s, 1H), 12.06(s, 1H) | ND | C23H16ClN3O3.0.5H2O C 64.57/64.71 H 3.94/4.01 N 9.79/9.84 |
| 169 | 7-chloro-4-hydroxy-2-(3'-methylphenyl)-5,10-dihydro-2H-pyridazino[4,5-b]quinoline-1-one | 37% | >260 (dec) | 2.33(s, 3H), 3.80(s, 2H), 6.93 (dd, 1H, J1=8.13, J2=2.0), 7.13 (d, 2H, J=8.16), 7.22(d, 1H, J=2.0), 7.31(m, 3H), 9.07(s, 1H), 12.01 (bs, 1H) | 340 | C18H14ClN3O2.0.25H2O C 62.70/62.79 H 4.31/4.24 N 12.13/12.20 |
| 170 | 7-chloro-4-hydroxy-2-hexyl-5,10-dihydro-2H-pyridazino[4,5-b]quinoline-1-one | 62% | 208–210 | 0.85(t, 3H, J=6.4), 1.25(bs, 6H), 1.61 (bs, 2H), 3.74(s, 2H), 3.80(t, 2H, J=7.2), 6.87(dd, 1H, J1=8.1, J2=2.1), 7.10(d, 1H, J=8.1), 7.17(d, 1h, J=1.1), 8.88(s, 1H), 11.73(bs, 1H) | 334 | C17H20C1N3O2.0.25H2O C 60.35/60.22 H 6.11/5.94 N 12.42/12.44 |
| 171 | 7-chloro-4-hydroxy-2-(3'-5'-bis-trifluoromethylbenzyl)-5,10-dihydro-2H-pyridazino[4,5-b]quinoline-1-one | 65% | 204–206 | 3.79(s, 2H), 5.23(s, 2H), 6.92(d, 1H, J= 8.1), 7.12(d, 1H, J=8.1), 7.19(s, 1H), 7.95 (s, 2H), 8.05(s, 1H), 9.00(s, 1H), 11.97 (bs, 1H) | 476 | C20H12ClF6N3O2. 0.6CH3OH H 3.20/3.23 N 8.15/8.20 |
| 172 | 7-chloro-4-hydroxy-2-(3'-methoxybenzyl)-5,10-dihydro-2H-pyridazino[4,5-b]quinoline-1-one | 40% | 238–240 | 3.72(s, 3H), 3.79(s, 2H), 5.09(s, 2H), 6.81 (m, 3H), 6.91(dd, 1H, J1=8.1, J2=1.8), 7.11(d, 1H, J=8.1), 7.21(m, 2H), 8.95 (s, 1H), 11.84(bs, 1H) | 370 | C19H16ClN3O3 C 61.40/61.70 H 4.45/4.40 N 11.26/11.40 |

TABLE 9-continued

The following examples were prepared according to the procedure described in Example 145 using similar reagents and conditions from the appropriate precursor, the preparation of which is described in Examples 1–144.

| Ex | Name | yld | m.p. (° C.) | NMR (d6-DMSO) | MS (CI) | Analysis (exp.theory) |
|---|---|---|---|---|---|---|
| 173 | 7-chloro-4-hydroxy-2-(2'-methylbenzyl)-5,10-dihydro-2H-pyridazino[4,5-b]quinoline-1-one | 80% | 244–246 (dec) | 2.31(s, 3H), 3.79(s, 2H), 5.03(s, 2H), 6.91 (m, 2H), 7.15(m, 5H), 8.98(s, 1H), 11.78 (bs, 1H) | 354 | C19H16ClN3O2.0.10H2O C 64.10/64.17 H 4.64/4.59 N 11.64/11.82 |
| 174 | 7-chloro-4-hydroxy-2-(ethyl thiomethyl)-5,10-dihydro-2H-pyridazino[4,5-b]quinoline-1-one | 85% | 235–237 | 2.08(s, 3H), 2.74(t, 2H, J=7.0), 3.75(s, 2H), 4.01(t, 2H, J=7.0), 6.90(dd, 1H, J1=8.1, J2=1.9), 7.10(d, 1H, J=8.1), 7.18(s, 1H), 8.93(s, 1H), 11.83(s, 1H) | 324 | C14H14ClN3O2S.0.4H2O 0.4CF3CO2H C 47.04/47.20 H 4.03/4.07 N 11.48/11.16 |
| 175 | 7-chloro-4-hydroxy-2-(2'methoxybenzyl)-5,10-dihydro-2H-pyridazino[4,5-b]quinoline-1-one | 49% | >250 | 3.82(appd, 5H), 5.01(s, 2H0, 6.79(d, 1H, J=7.2), 6.86(m, 2H), 7.01(d, 1H, J=8.2), 7.12(d, 1H, J=8.2), 7.23(m, 2H), 8.95(s, 1H), 11.72(bs, 1H) | 370 | C19H16ClN3O3.0.8H2O 0.5CF3CO2H C 54.39/54.44 H 4.27/4.13 N 9.49/9.52 |
| 176 | 7-chloro-4-hydroxy-2-butyl-5,10-dihydro-2H-pyridazino[4,5-b]quinoline-1-one | 73% | 198–200 | 0.89(t, 3H, J=7.3), 1.29(m, 2H), 3.74(s, 2H), 3.84(t, 2H, J=7.2), 6.89 (dd, 1H, J1=8.1, J2=2.1), 7.10(d, 1H, J=8.1), 7.18(d, 1H, J=2.1), 8.88(s, 1H), 11.73(bs, 1H) | 306 | C15H16ClN3O2.0.3H2O. 0.3CF3CO2H C 54.27/54.25 H 4.97/4.93 N 12.36/12.17 |
| 177 | 7-chloro-4-hydroxy-2-(1'-methylbutyl)-5,10-dihydro-2H-pyridazino[4,5-b]quinoline-1-one | 72% | 140–142 | 0.83(t, 3H, J=7.3), 1.15(m, 5H), 1.47(m, 1H), 1.69(m, 1H), 3.73(s, 2H), 4.93(m, 1H), 6.88(dd, 1H, J1=8.1, J2=2.0), 7.09(d, 1H, J=8.1), 7.17d, 1H, J=2.0), 8.87(s, 1H), 11.62(bs, 1H) | 320 | C16H18ClN3O2.0.25H2O C 59.32/59.26 H 5.66/5.75 N 12.89/12.96 |

FORMULAE

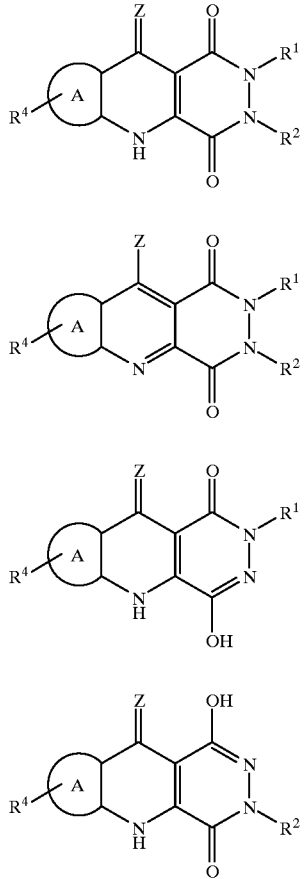

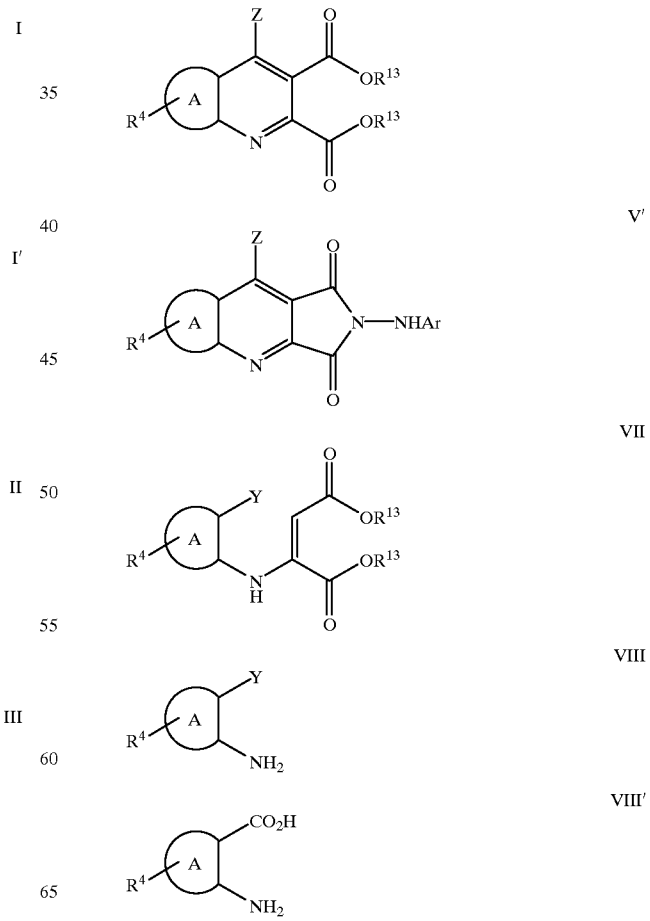

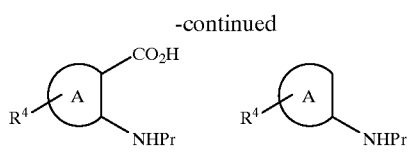
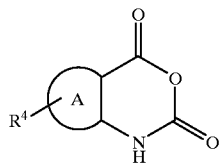
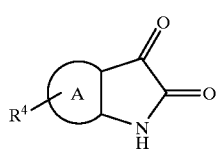
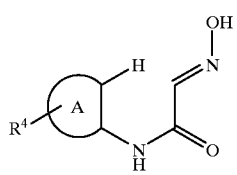
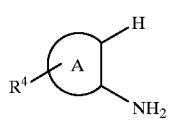
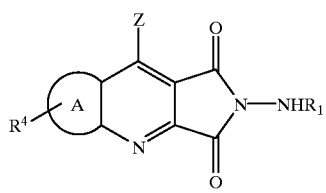
XI
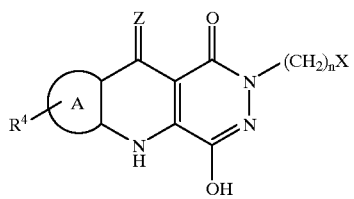
XII
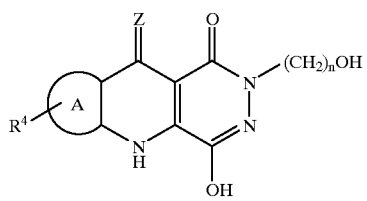
XIII
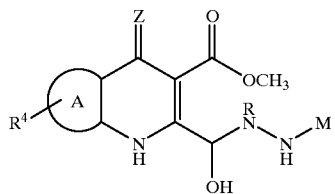
XIV
R = H, Bn
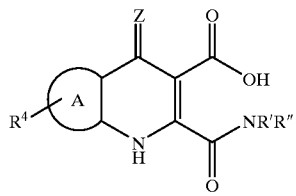
XVIII
R', R'' together form
a cyclic ring with N.
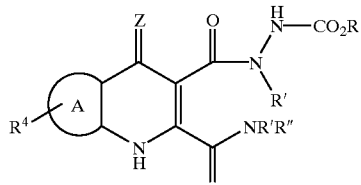
XIX
R', R'' together form a cyclic ring with N,
R is t-butyl or a bulky alkyl substituent
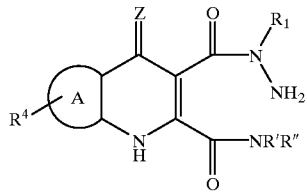
XX
R', R'' together form
a cyclic ring with N.
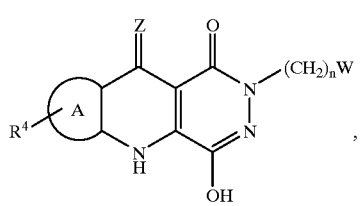
XXI
n > 0
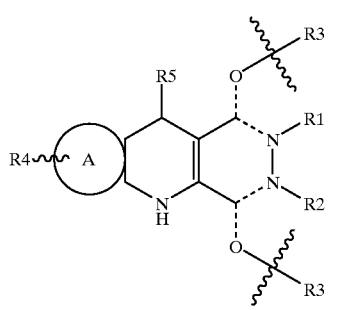
A
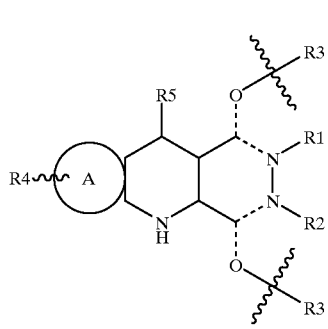
A'

B
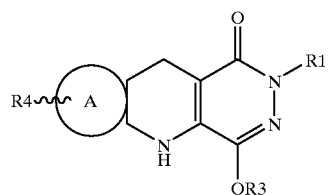
B'
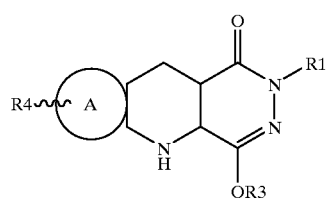
C
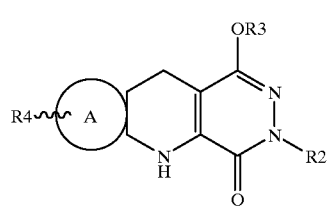
C'
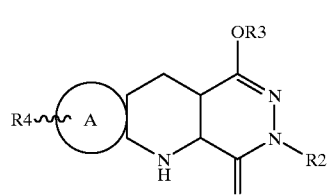
D
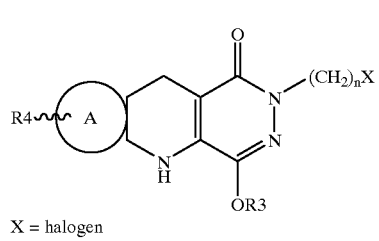
X = halogen
D'
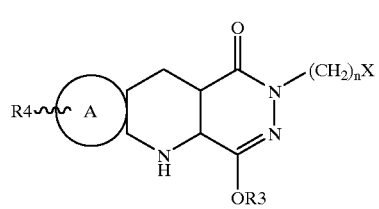
E
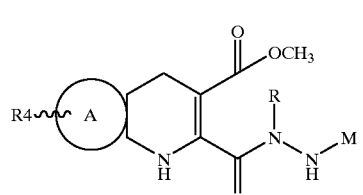
R = H, Bn
E'
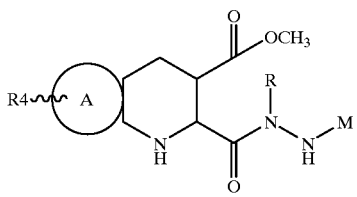
F
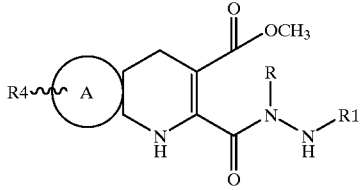
R = H, Bn
F'
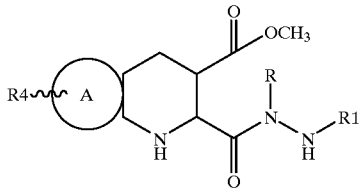
G
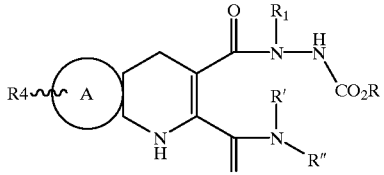
R', R" together form a cyclic ring with N,
R is t-butyl or a bulky alkyl substituent
G'
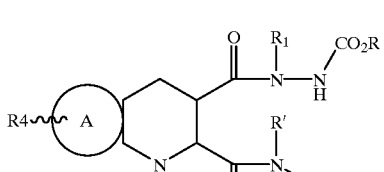
H
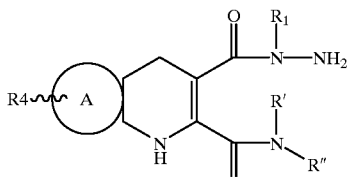
R', R" together form a cyclic ring with N,
R is t-butyl or a bulky alkyl substituent
H'
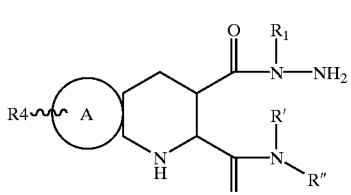

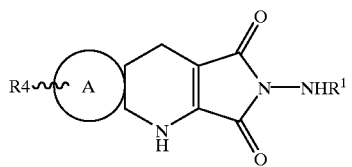
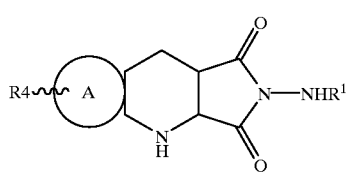
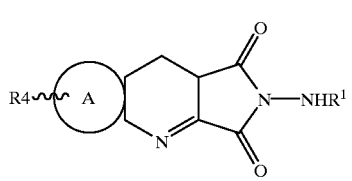
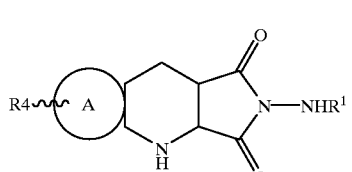
K
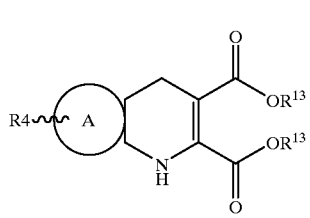
K'
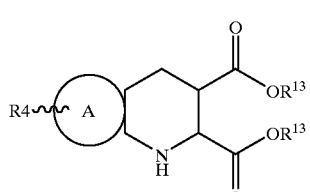
L
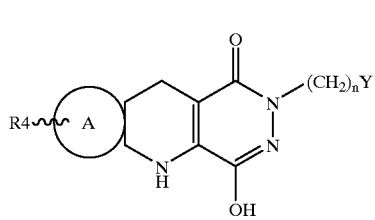
i
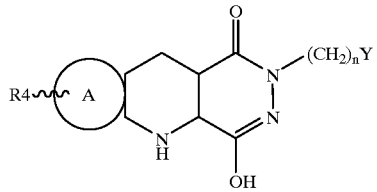
i''
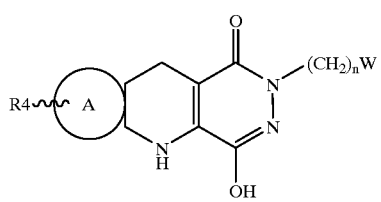
J
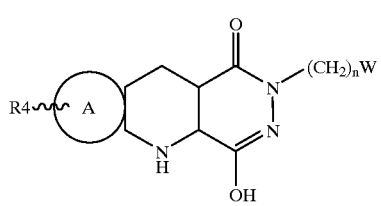
i'''
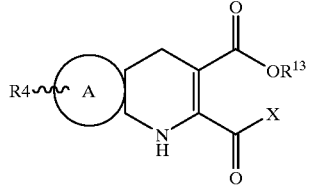
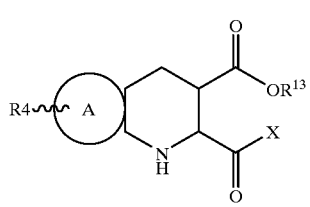
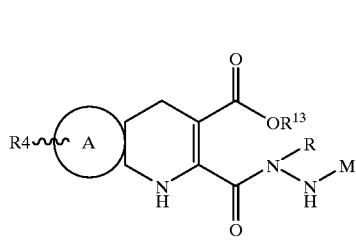
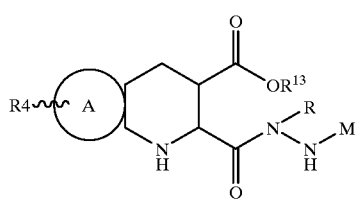
L'
M
M'
N
N'
O
O'

99
-continued
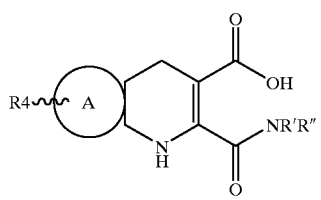
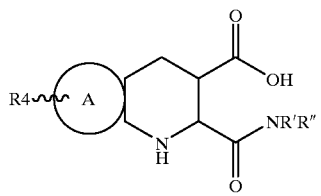
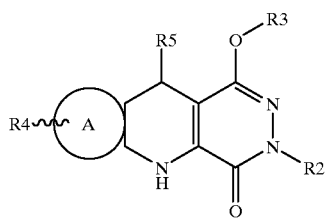 Q
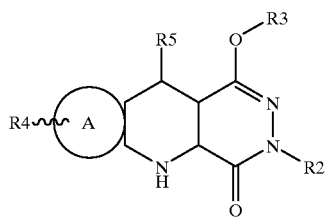 Q'
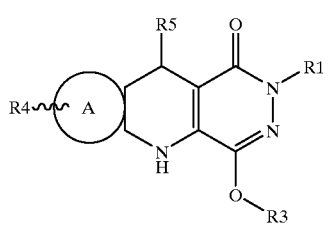 R
100
-continued
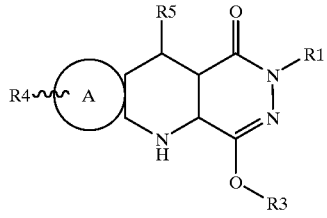 P
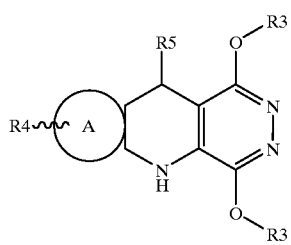 P'
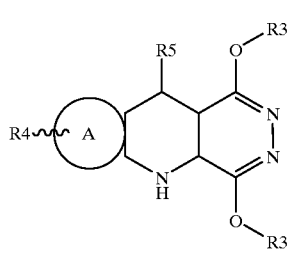
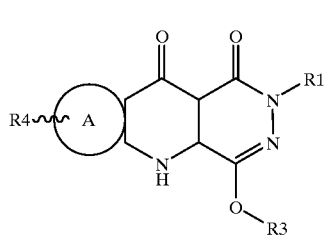
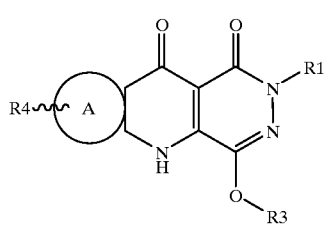
R'
S
S'
T
T'

SCHEME 1 & 2
SCHEME 1
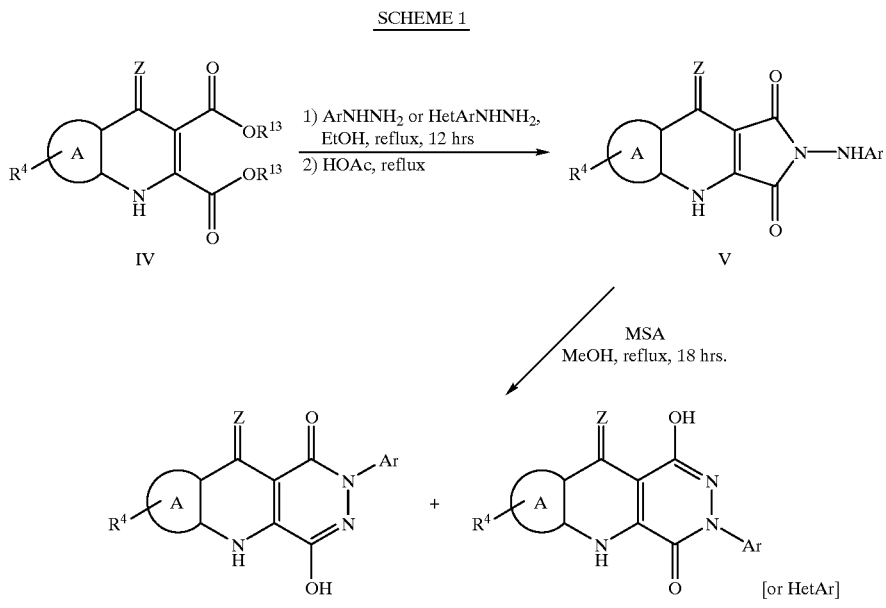
The isomers may be separated by fractional acidification of meglumine/choline solutions.
SCHEME 3 & 4
SCHEME 3

-continued
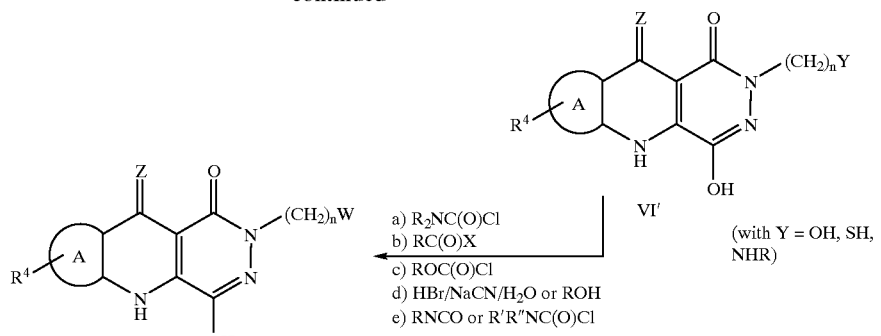
SCHEME 4
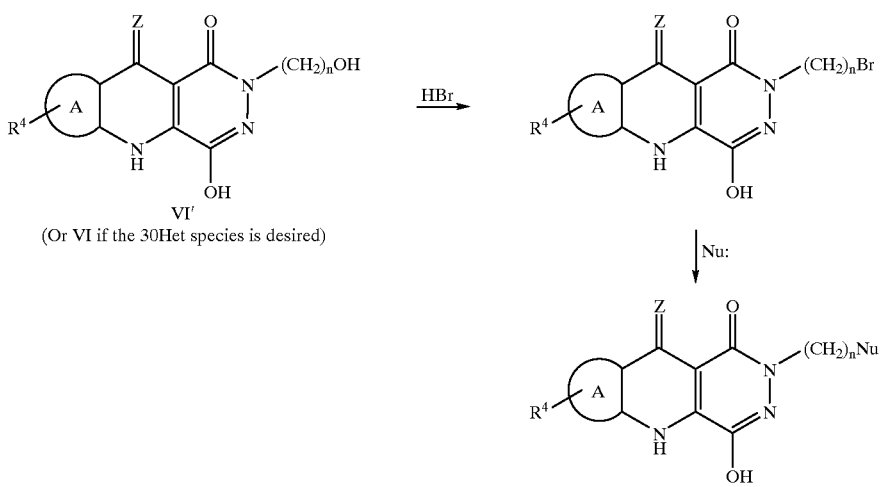
Nu: = heterocycle, i.e.,
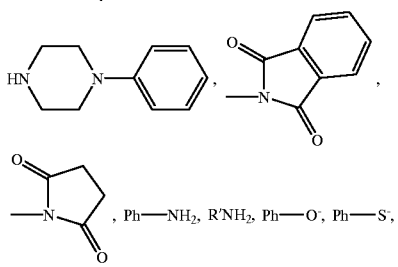
, Ph—NH₂, R'NH₂, Ph—O⁻, Ph—S⁻,
SCHEME 5
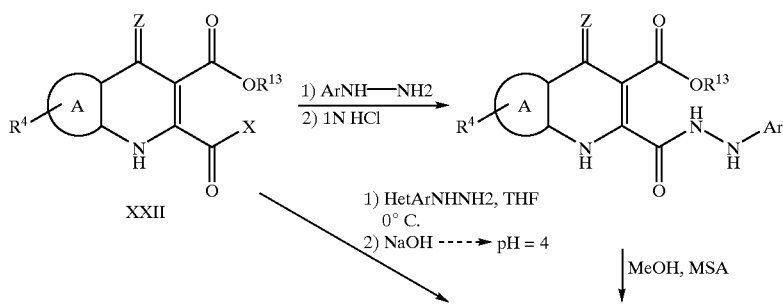

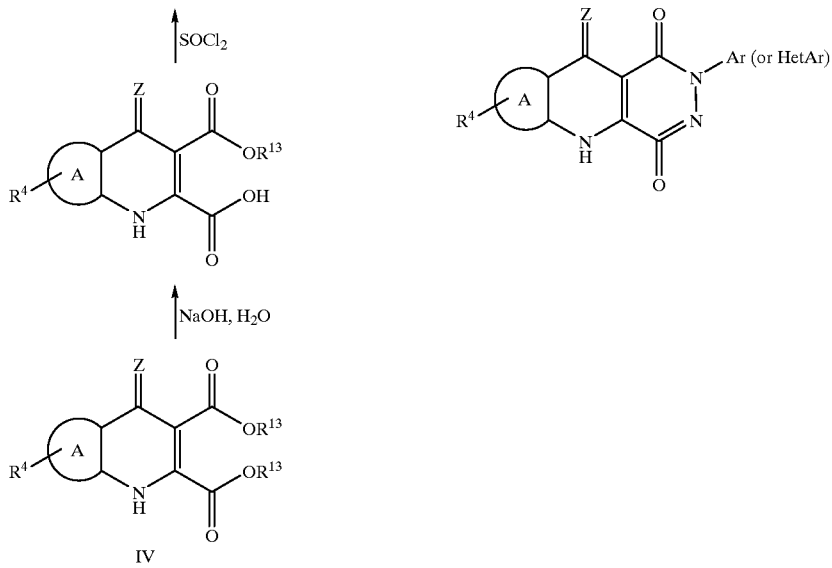
SCHEME 6
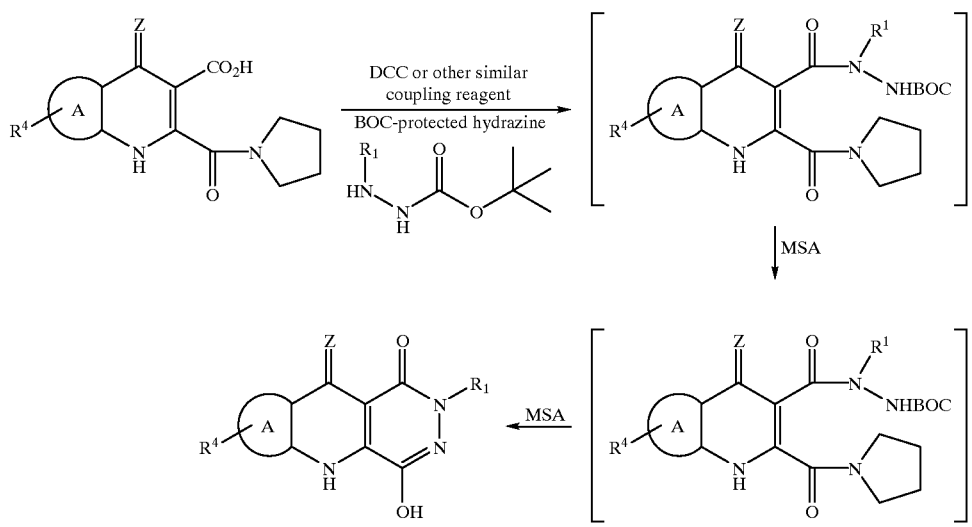

SCHEME 7

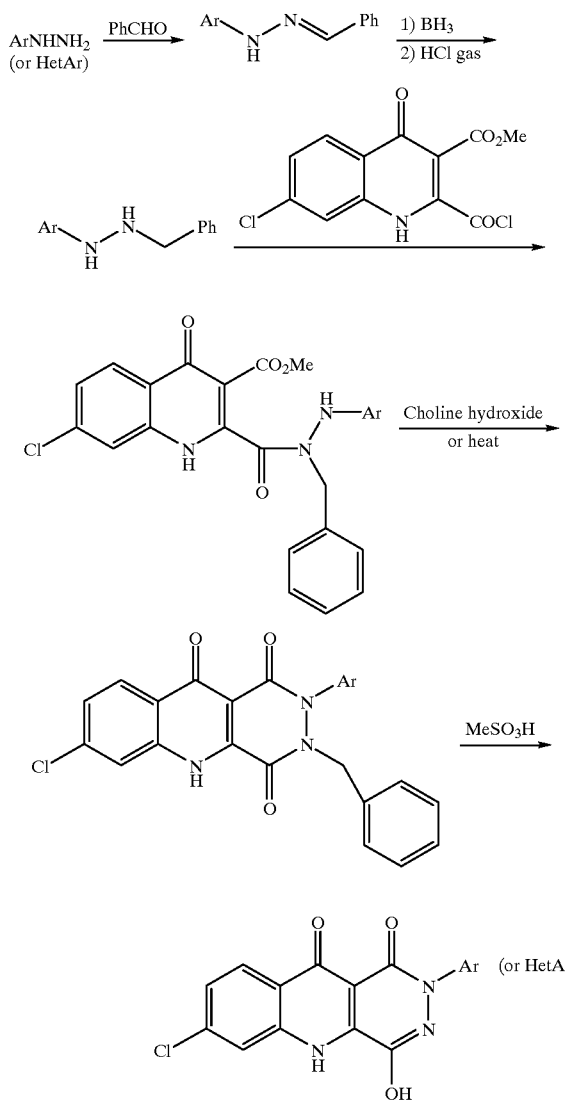

SCHEME 8

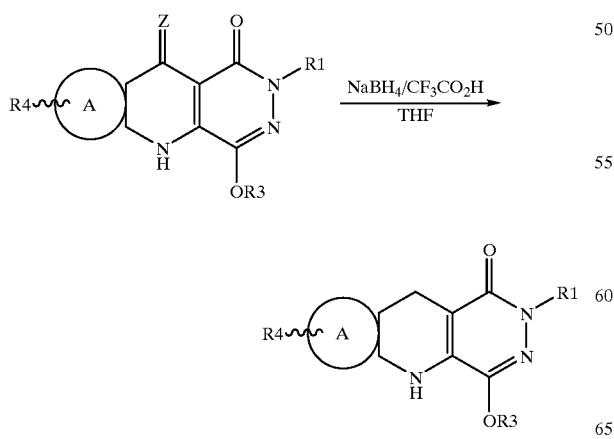

What is claimed is:
1. A compound of formula (B) or (B'):

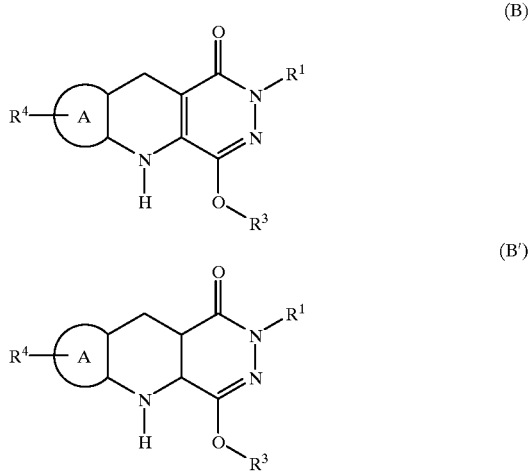

tautomers thereof, and pharmaceutically-acceptable salts thereof, wherein:
A is phenyl substituted at 1 or 2 positions with $R^4$ where $R^4$ is halo;
$R^1$ is selected from H and $(CH_2)_nM$ wherein:
  n is selected from 0, 1, 2, 3, 4, 5 and 6;
  M is a moiety selected from hydroxy, $(C_1–C_4)$alkyl, thio$(C_1–C_4)$alkyl, anilino, and N-ethyl-4'-methoxyanilino, or,
  M is phenyl substituted at 0, 1 or 2 positions with a moiety selected independently at each occurrence from hydroxy, methoxy, phenoxy, fluoro, chloro, bromo, cyano, methyl and trifluoromethyl, or,
  M is pyridyl or methoxypyridyl; and
$R^3$ is selected from H, or —(CO)$R^6$ wherein $R^6$ is selected from methyl, ethyl, methoxycarbonylethyl, and phenyl.

2. A compound according to claim 1, wherein:
$R^4$ is chloro.

3. A compound according to claim 1, selected from the group consisting of
7-chloro-4-hydroxy-5,10-dihydro-2-(4'-methylphenyl)pyridazino[4,5-b]quinolin-1-one,
7,9-dichloro-4-hydroxy-5,10-dihydropyridazino[4,5-b]quinolin-1-one,
7-chloro-4-hydroxy-2-phenyl-5,10-dihydro-2H-pyridazino[4,5-b]quinolin-1-one,
7-chloro-4-hydroxy-2-(4'-methoxyphenyl)-5,10-dihydro-2H-pyridazino[4,5-b]quinolin-1-one,
7-chloro-4-hydroxy-5,10-dihydropyridazino[4,5-b]quinolin-1-one,
7,9-dichloro-4-hydroxy-2-(4'-methylphenyl)-5,10-dihydro-2H-pyridazino[4,5-b]quinolin-1-one,
7-chloro-4-hydroxy-2-hydroxyethyl-5,10-dihydro-2H-pyridazino [4,5-b]quinolin-1-one,
7-chloro-4-hydroxy-2-(N-ethyl-4'-methoxyanilino)-5,10-dihydro-2H-pyridazino[4,5-b]quinolin-1-one,
7-chloro-4-hydroxy-2-(4'-fluorophenyl)-5,10-dihydro-2H-pyridazino[4,5-b]quinolin-1-one,
7-chloro-4-hydroxy-2-(4'-methoxy-3-pyridyl)-5,10-dihydro-2H-pyridazino[4,5-b]quinolin-1-one,
7-chloro-4-hydroxy-2-(3',4'-dimethoxyphenyl)-5,10-dihydro-2H-pyridazino [4,5-b]quinolin-1-one, 7-chloro-4-hydroxy-2-(2',4'-dimethylphenyl)-5,10-dihydro-2H-pyridazino[4,5-b]quinolin-1-one, 7-chloro-4-hydroxy-2-(3'-methoxyphenyl)-5,10-dihydro-2H-pyridazino[4,5-b]quinolin-1-one, 7-chloro-4-hydroxy-2-(4'-bromo-2'-methoxyphenyl)-5,10-dihydro-2H-pyridazino[4,5-b]quinolin-1-one, 7-chloro-4-hydroxy-2-(ethylthioethyl)-5,10-dihydro-2H-pyridazino[4,5-b]quinolin-1-one, 7-chloro-4-hydroxy-2-(2',5'-dimethylphenyl)-5,10-dihydro-2H-pyridazino[4,5-b]quinolin-1-one, 7,9-dichloro-4-hydroxy-2-(4'-methoxyphenyl)-5,10-dihydro-2H-pyridazino[4,5-b]quinolin-1-one, 7-chloro-4-hydroxy-2-(4'-methylphenyl)-5,10-dihydro-2H-pyridazino[4,5-b]quinolin-1-one, 7,9-dichloro-4-hydroxy-2-(2',4'-dimethylphenyl)-5,10-dihydro-2H-pyridazino[4,5-b]quinolin-1-one, 7-chloro-4-hydroxy-2-(4'-bromo-2'-methylphenyl)-5,10-dihydro-2H-pyridazino[4,5-b]quinolin-1-one, 7-chloro-4-hydroxy-2-(2'-fluorophenyl)-5,10-dihydro-2H-pyridazino[4,5-b]quinolin-1-one, 7-chloro-4-hydroxy-2-(3'-chlorophenyl)-5,10-dihydro-2H-pyridazino [4-5-b]quinolin-1-one, 7-chloro-4-hydroxy-2-(2'-cyanophenyl)-5,10-dihydro-2H-pyridazino[4,5-b]quinolin-1-one, 7-chloro-4-hydroxy-2-(3'-methylphenyl)-5,10-dihydro-2H-pyridazino [4,5-b]quinolin-1-one and 7-chloro-4-hydroxy-2-(3'-phenoxyphenyl)-5,10-dihydro-2H pyridazino[4,5-b]quinolin-1-one.

4. A compound according to 1, selected from the group consisting of:

7-chloro-4-hydroxy-2-(hexyl)-5,10-dihydro-2H-pyridazino[4,5-b]quinolin-1-one, 7-chloro-4-hydroxy-2-(3',5'-bistrifluoromethylbenzyl)-5,10-dihydro-2H-pyridazino[4,5-b]quinolin-1-one, 7-chloro-4-hydroxy-2-(3'-methoxybenzyl)-5,10-dihydro-2H-pyridazino[4,5-b]quinolin-1-one, 7-chloro-4-hydroxy-2-(2'-methylbenzyl)-5,10-dihydro-2H-pyridazino[4,5-b]quinolin-1-one, 7-chloro-4-hydroxy-2-(2-(ethylthiomethyl)-5,10-dihydro-2H-pyridazino[4,5-b]quinolin-1-one, 7-chloro-4-hydroxy-2-(2'-methoxybenzyl)-5,10-dihydro-2H-pyridazino[4,5-b]quinolin-1-one, 7-chloro-4-hydroxy-2-butyl-5,10-dihydro-2H-pyridazino[4,5-b]quinolin-1-one, 7-chloro-4-hydroxy-2-(1'-methylbutyl)-5,10-dihydro-2H-pyridazino[4,5-b]quinolin-1-one, 7-chloro-4-hydroxy-2-(4'-hydroxyphenyl)-5,10-dihydro-2H-pyridazino[4,5-b]quinolin-1-one, 7-chloro-4-benzoyloxy-2-(4'-methylphenyl)-5,10-dihydro-2H-pyridazino[4,5-b]quinolin-1-one, 7-chloro-4-propionyloxy-2-(4'-methylphenyl)-5,10-dihydro-2H-pyridazino[4,5-b]quinolin-1-one, 7-chloro-4-acetyloxy-2-(4'-methylphenyl)-5,10-dihydro-2H-pyridazino[4,5-b]quinolin-1-one, 7-chloro-4-carbomethoxypropionyloxy-2-(4'-methylphenyl)-5,10-dihydro-2H-pyridazino[4,5-b]quinolin-1-one, and 7-chloro-4-hydroxy-2-(4'-methoxy-2'-methylphenyl)-5,10-dihydro-2H-pyridazino[4,5-b]quinolin-1-one.

5. A pharmaceutical composition comprising a pharmaceutically-acceptable excipient or diluent and a compound according to claim 1.

6. A method for the treatment of transient cerebral ischemic attack, perinatal asphyxia, epilepsy, drowning anoxia, spinal cord trauma, and brain trauma, comprising administering to a mammal in need of treatment therefor an effective amount of a compound according to claim 1.

7. A process for producing a compound according to claim 1, said process comprising:

reducing a compound of formula T or T'

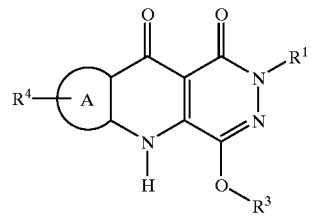

(T)

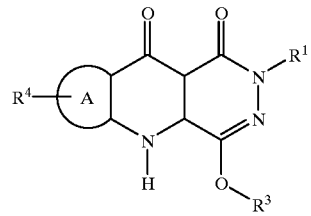

(T')

in tetrahydrofuran with sodium borohydride in the presence of trifluoroacetic acid, wherein:

said $R^1$, $R^3$ and $R^4$ moieties have the values described therefor in claim 1;

any $R^1$, $R^3$ or $R^4$ substituent of compound T or T' susceptible to reduction is protected with a conventional protective group before said reduction, and said protective groups, if present, are removed after said reduction.

8. The process according to claim 7, additionally comprising:

forming a pharmaceutically-acceptable salt by reacting said compound made by the process of claim 7 with a pharmaceutically-acceptable acid.

* * * * *